(12) United States Patent
Eaton et al.

(10) Patent No.: US 7,179,907 B2
(45) Date of Patent: Feb. 20, 2007

(54) ANTIBIOTIC COMPOUNDS

(76) Inventors: Bruce Eaton, 105 Greyfriars La., Cary, NC (US) 27511; Theodore M. Tarasow, 1242 Reserve Dr., Longmont, CO (US) 80501; Dan Nieuwlandt, 1340 Sommerset Cir., Longmont, CO (US) 80501; Torin Dewey, 2269 Watersong Cir., Longmont, CO (US) 80504

( * ) Notice: Subject to any disclaimer, the term of this patent is extended or adjusted under 35 U.S.C. 154(b) by 0 days.

(21) Appl. No.: 10/497,764

(22) PCT Filed: Dec. 18, 2002

(86) PCT No.: PCT/US02/40739

§ 371 (c)(1),
(2), (4) Date: Feb. 15, 2005

(87) PCT Pub. No.: WO03/051314

PCT Pub. Date: Jun. 26, 2003

(65) Prior Publication Data

US 2005/0124598 A1    Jun. 9, 2005

Related U.S. Application Data

(60) Provisional application No. 60/340,255, filed on Dec. 18, 2001.

(51) Int. Cl.
*C07D 205/085* (2006.01)
*C07D 227/087* (2006.01)
*C07D 403/12* (2006.01)
*C07D 405/12* (2006.01)
*C07D 403/04* (2006.01)

(52) U.S. Cl. .............. 540/363; 540/360; 540/362; 435/DIG. 34; 544/216

(58) Field of Classification Search ............... 540/360, 540/362, 363
See application file for complete search history.

(56) References Cited

U.S. PATENT DOCUMENTS 4,448,782 A    5/1984    Afonso (Continued)

FOREIGN PATENT DOCUMENTS

GB    2 183 661 A    6/1987

(Continued)

OTHER PUBLICATIONS

Dictionary.com definition of "Carbamoyl" <http://dictionary.reference.com/search?q=carbamoyl&r=66> downloaded from the internet Sep. 12, 2006.*

(Continued)

*Primary Examiner*—Mark L. Berch
(74) *Attorney, Agent, or Firm*—Swanson & Bratschun, L.L.C.

(57) ABSTRACT

The present invention provides methods for identifying (3-amino-2-oxo-azetidin-1-yl) acetic acid derivatives with anti-PBP2a activity. The method involves the selection of RNA biocatalysts that promote the formation of (3-amino-2-oxo-azetidin-1-yl) acetic acid derivatives with anti-PBP2a activity from component reactants. The invention also provides novel (3-amino-2-oxo-azetidin-1-yl) acetic acid derivatives with anti-PBP2a activity identified by these methods. The invention also provides RNA biocatalysts that are capable of catalyzing the formation of (3-amino-2-oxo-azetidin-1-yl) acetic acid derivatives from component reactants.

4 Claims, 9 Drawing Sheets

U.S. PATENT DOCUMENTS

| | | | |
|---|---|---|---|
| 4,605,735 | A | 8/1986 | Miyoshi et al. |
| 4,794,073 | A | 12/1988 | Dattagupta et al. |
| 4,968,602 | A | 11/1990 | Dattagupta |
| 5,270,163 | A | 12/1993 | Gold et al. |
| 5,281,627 | A | 1/1994 | Griffith |
| 5,288,514 | A | 2/1994 | Ellman |
| 5,306,619 | A | 4/1994 | Edwards |
| 5,506,337 | A | 4/1996 | Summerton et al. |
| 5,541,061 | A | 7/1996 | Fodor et al. |
| 5,565,324 | A | 10/1996 | Still et al. |
| 5,571,681 | A | 11/1996 | Janda |
| 5,573,905 | A | 11/1996 | Lerner et al. |
| 5,593,853 | A | 1/1997 | Chen et al. |
| 5,659,069 | A | 8/1997 | Eaton et al. |
| 5,723,289 | A | 3/1998 | Eaton et al. |
| 5,723,592 | A | 3/1998 | Eaton et al. |
| 5,731,432 | A | 3/1998 | Erion |
| 5,760,266 | A | 6/1998 | Eaton et al. |
| 5,789,160 | A | 8/1998 | Eaton et al. |
| 5,858,660 | A | 1/1999 | Eaton |
| 6,030,776 | A | 2/2000 | Eaton |
| 6,048,698 | A | 4/2000 | Eaton |
| 6,204,260 | B1 | 3/2001 | Bruns |
| 6,225,500 | B1 | 5/2001 | Eaton et al. |

FOREIGN PATENT DOCUMENTS

| | | |
|---|---|---|
| WO | WO 89/06694 | 7/1989 |
| WO | WO 90/11364 | 10/1990 |
| WO | WO 97/19787 | 6/1991 |
| WO | WO 91/14696 | 10/1991 |
| WO | WO 91/14699 | 10/1991 |
| WO | WO 91/19789 | 12/1991 |
| WO | WO 91/19813 | 12/1991 |
| WO | WO 92/14843 | 9/1992 |
| WO | WO 94/13688 | 6/1994 |
| WO | WO 95/16788 | 6/1995 |
| WO | WO 96/06944 | 3/1996 |
| WO | WO 96/17086 | 6/1996 |
| WO | WO 89/05852 | 6/1999 |

OTHER PUBLICATIONS

NNIS (1999) Am. J. Infect. Control 27:520-532.
Allinger et al. (1971) Organic Chemistry, Worth Publ., Inc. New York, NY p. 330.
Alper (1994) Science 264:1399.
Bartel & Szostak (1993) Science 261:1411.
Brenner & Lerner (1992) Pro. Natl. Acad. Sci. USA 89:5381.
Cech (1987) Science 236:1532.
Chambers et al. (2001) Emerging Infectious Diseases 7:178-182.
Chung et al. (1994) Proc. Natl. Acad. Sci. USA 91:2372.
Ellington & Szostak (1990) Abstract of papers presented at the 1990 meeting on RNA Processing, Cold Springs Harbor Laboratory, Cold Springs Harbor, N Y, p. 84.
Dewey et al. (1996) Nucleosides and Nucleotides 15:1611-7.
Fodor et al. (1991) Science 251;767.
Green (1991) Methods: A Companion to Methods in Enzymology 2(1):75-86.
Joyce (1989) Gene 82:83.
Joyce & Inoue (1989) Nucleic Acids Research 17:711.
Kinzler & Vogelstein (1989) Nucleic Acids Research 17:3645.
Kramer et al. (1974) J. Mol. Biol. 89:719.
Levisohn & Spiegelman (1969) Proc. Natl. Acad. Sci. USA 63:805.
Levisohn & Spiegelman (1968) Proc. Natl. Acad. Sci. USA 60:866.
Longman (1994) In Vivo 23-31.
Lorsch & Szostak (1994) Nature 371:31.
McCorkle & Altman (1987) J of Chem. Ed. 64:221.
Nagpal et al. (1990) Autoimmunity 8:59 (Abstract).
Needels et al. (1993) Proc. Natl. Acad. Sci. USA 90:10700.
Ohlmeyer et al. (1993) Proc. Natl. Acad. Sci. USA 90:10922.
Oliphant et al. (1989) Mol. Cell Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Piccirilli et al. (1992) Science 256:1420.
Prudent et al. (1994) Science 264:1924.
Robertson & Joyce (1990) Nature 344:467.
Szostak, (1988) "Structure and Activity of Ribozymes," in *Redesigning the Molecules of Life*, (S.A. Benner ed.) Springer-Verlag Berlin Heidelberg, pp. 87-113.
Thiesen & Bach (1990) Nucleic Acids Research 18:3203.
Watson J.D. et al., 1988 "Molecular Biology of the Gene," Benjamin /Cummings, Menlo Park California, pp. 382-430.
Streitwieser & Heathcock, Organic Chemistry, 2.ed, Macmillan Publishing Co, Inc., p. 616-617 (1981).

* cited by examiner

3H Biocatalyst Subpopulation Sequences

5'GGGAGAATCAAAGTAATGCTCA-(3H subclone)-TTCGACAGGAGGCTCACAACAGGC 3'

U = 5-(4-pyridylmethyl) uridine

FIGURE 2

8I Biocatalyst Subpopulation Random Region Sequence

U= 5-(4-pyridylmethyl)U

```
I41:-GUUGCACGCGCAAUUGGUGACUCCGUGAG--GGGCGGGGGCCUCCACCAAGUCUGA--CUGCGCGAU---UCA-----ACCGAG--GGGAUGUCUUAAGGUCGG---UUGC-----GCGUC
SEQ ID NO:86
I24:-GUUGGA--GCGUA---GGAGU-UCCCUGAGGGGACGGGCGGGAUACAAGGGCGGCAAACGUGACCGAAUA-UAACCCAAACCNANAAGCNAGGANNNAAACUCNAACUAGG AAAAANNNAA
SEQ ID NO:87
I42:-CUGGG------GCAA-----UU-UCCCGGUUG--GGAGGAUGGCUUAAGGAGGAGCUCCUGA-GUGAGCAAAGCCCUCGGUGGGGCCCGG--GGGUGUGCUGCAAC-CGAGGUGUGAU---GCGCA
SEQ ID NO:88
I40:AGGUGG------GGA-------GACUGCCAGAGCUGCCAUGCCGGCC---CAC CGUGUGGGCCCGAGCGAUCCGGCCGGCCUGUAGGUACGNAG--GACA----CUUGAAC--GA--UUCG-UAGUAUGGA
SEQ ID NO:89
I2 -GUUGGA--GCUUANGAGC-CCCUGAGCGGGACGGGAGUGGAGUGCAAACGU---GAAAAA--AAAAAAAAU---ANA--AAUAAAAGGAAA---AAAAAAAAAA---AAAAAAAAAAAG
SEQ ID NO:90
I21:-GUUGGA--GCUUAGGAGUUCCCUGAGGUGGAGUGGGACGGGAGUGGGAGAAUACAGGGG--UGGCAAACGU----GAAAAAA--AAAAAAAA---AAA--AAAAAAAAAAAA---AAAAA-----AAAAA----U
SEQ ID NO:91
I31: -GUUGGA---GCUUAGGAGUGCUCCCUGAGCAGGAGCGGGACGGGAGAAUACAANGG--UGGNAAACGU---GNAAAAA---AAAAAAA---AAA--AAAAAANNAAANA---NNAAANGGAA---AAAAANAA---U
SEQ ID NO:92
I16: -GUUGGA---GCUUAGGAGUCUCCCUGAGCGCGACGGGACGGGACGGGAAUACAGGG--UGGCAGACGU---UGGCAGACGCGU----GAAAAAAAAAAAAAAAAAAA---AGG--AAAAAAAAAAAAAA--AAAAAAAAU---
SEQ ID NO:93
I110: -GUUGGA---GCUUAGGAGUUCCCUCAGCGGGACGGGAAUACUAGGG--CGGCAAACGU----GAAAAAAAGAAAAAAAAAA---AAA--AAAAAAAAAAA----AAAAAAAAAA--AAAAAANCCUCC
SEQ ID NO:94
I23: -GUUGGG--GCCUAGGAGCUUCCCUGAGGAGCGGGAAUACAGGG--UGGCAAACGU---GRAAAAAGAAAAGAAAAGAAAAA---AAA--AAAAAAAAAAAAA-- AAAAAAAAAA---AAAAAAAU---
SEQ ID NO:95
I20: -GUUGGA---GCUUAGGAGCUCCUGAGCGGGACGGGAAUACAAGGG--UGGCAGAGCAGCGGUNAAAAAANANAAAGNAAAAAAAAAAAAA--AAAAAAAAAAAAAAA---AAAAAAAAAG----AAAAAAAAAAAA
SEQ ID NO:96
I29: -GUUGGA---GCCUANGAGUUCCCUGAGCGGGGCCCUGAGCGGGAAUACAGGG--UGGCAGACNACUGAAUACAGGG--UGGCAAACGUGAAAAAAAAAAAAAAGGAGGAAA---AAAAAAAAAAAAAAGGAAAANNNAAA----AANNNAAAAAAAA
SEQ ID NO:97
I5: -GUUGGA---GCUUAGGAGCUCCCUGAGCGGGACGGGAGCGGGAAUACAGGG--UGGCAAACGUGAAAAAAAA--GAAAAAAAA----AAA--AAAAAAAAAA---AAAANAAAA---AAAAAAAAAAAAAAN
SEQ ID NO:98
I44: -GUUGGA---GCCUAGNAGCUCCCUNAGCCGGGNUGAGGAAUNCAAGGG--UGGUAACCGU---GAAAAGA--AAAACCCCC---AA----AA---UAAAAAAAAAA---AAAAAAAAAA---NAAAAANNNUUUN
SEQ ID NO:99
I28: -GUUGGA---GCUUAGNAGCNCCNUNAACGNANGNGGAAANCAAGGG--NGGCNCNCNU---UUAAAAAA---AAAAAAAAA---AA---AAAAAAAAAAAA----AA-----AAAANAAAA----AAAAANRAAAA-A
SEQ ID NO:100
I22: -GUUANGGGCCUCCCUGUNCGGGACGGGAACNCNANGG---GGCNACCGUUUUNAAAAAA---AAAAAAAAA---AAG--NAAAAANNAAAAA---AAAAAAAAAA----AAAAAAAAAAAAG
SEQ ID NO:101
I16: -GUUGGA---GCUUAGGAGUUCCCUNANCGGGACGGGAANACAANGG--UGGCAAACGUN--NAAAAAAGAAAAAAAAAAAAAA-AAA--AAAAAAAAAAAAAAA---AAA--AAAAAAAAAAAAAAAAUAG
SEQ ID NO:102
I12: -GUUGGA---GCUUAGGAGUUCCCUGAGUGCGACACCGGGAAUAUAAGGG--GGCAAACGU---GGCAAACGU---GAAAAAA---AAAAAAAA----AAN--NAAAAAAAGGAA----AAAAAAAAAA----AAAAAAANN----
SEQ ID NO:103
```

FIGURE 4

8I Biocatalyst Subpopulation Random Region Sequence (cont)

```
I17: -GUUGGA---GCUUAGGAGCUCCCUGAGCGGGAUGGGGAUACAAGGG--CGGCAAACGU---GAAAAAA--AAAANGAAA---AAA--AAAAAAANAAAA---AAAAAAAAAA----AGGAAAAG---
SEQ ID NO:104

I27: -GUUGGA---GCUUANGAGUCCCUGAGCGGGACGGGGAUAUACAAGGG--GGCAGACGU---GAAAAAA---CNAAAAAA---AAA--AAAAAAAAAAAAA---ANNNNAAAAA----AAAAAAAAU---U
SEQ ID NO:105

I11: -GUUGGA---GCUUAGGAGCUCCUCGAGCGGGA-GGGGAUGCGGAGGG--UGGCAAACGA---GAAAAAA---AAAAAAAA---AAA--AAAAAAAAAAAAA---AAAAAAAAAA----AAAAAAAUU---
SEQ ID NO:106

I7: -UAAUNU--GGUUCCGAA-----AAUNUNAA--GGUGUCCCUAAGUU----AAAAAAA--AAAAAAAAAAAAAAAAAAAAA--AAA--AAAAAAAAAAAAA---AAAAAAAAAA----AAAAAAAUU---
SEQ ID NO:107

I15: -UAAUNU--GGUUCCGAA-----AAUNUNAA--GGUGUCCCUAAGUU----AAAAAAA--AAAAAAAAAAAAAAAAAAAAA--AAA--AAAAAAAAAAAAA---AAAANAAGG-UCUUCAGCUGACGCAU
SEQ ID NO:108

I32: -UAAUGN--GGUUACGNA-----AAUNUGAA--GGNGUCCCUAAGU-----AAAAGA---AAAAAAANAAGNAVAAA--AAA--AAAAAAAAAAAAA---AAAAAAAGG-UCUUCAGCUGACGCAU
SEQ ID NO:109

I4: -CAAUGU--GGUUCCGAA------GAUGUAA--GGUGUCCCUAAGUN----AAAAAA---AAAAAAAAAAAAAAAAGG-AAA--AAAAAAAAAAAAA---AAAANNAAGG-UCUUCAGCUGACGCAU
SEQ ID NO:110

I26: -UAAUGU--GGUUCCGAA------GAUGUAA--GGUGUCCCUAAGCC----AAAAAAA--ANAAAAAAAAAAAAAAAANA---A--A-AAAAAAAAAA---AAAAAAAAAA----AANGGUCUUCAGCUGACGCAU
SEQ ID NO:111

I14: -UAAUGU--GGUUCCGAA------GAUGUGGA--GGUGUCCCUAAGUA----AAAAAGA--AAAAAAAAAAAAAAAAAAA--ANNGGAAAAAAAAAAAAA---AAAAAAAAAAGGUCUUCAGCUGCCGCAU
SEQ ID NO:112

I1: -GUUGGA---GCUUAGGAGCUCCCUGAGCGGGACGGGGAUAUACAAGGG--UGGCAUACGU---GAAAAAA--GAAANGAAAA----AAAAAAAAAAAAAAA-----NNNNNNNNNGGGAAAAAAAAA--AG
SEQ ID NO:113

I33: -GUUGGA---GCUUAAGAGCUCCCUGAGUGGAACGGGGAUAUACAAGGG--UGGCAAACGU---GAAAAAAAAAAAAAAA---AAA--AVNNNNACCNNUNN--AAAAANAAAA-----AAAAAAAAN---U
SEQ ID NO:114

I2: -GUUGGA---GCUUANGAGC--CCCUGAGCGGGGACGGGGACAGGACGGGGAAUACAAGGG--UGGCAAACGU---GAAAAAA---AAAAAANA-----AAAAAANA-------AAAANAANCUUNNGGAANNAANNAA--AUAAAAAAAUACNG
SEQ ID NO:115

I45: -GUUGGA---GCUUANGAGCUCCCUGAGCAGGACGGGGAUAUACAAGGG--UGGCAAACGU---GAAAAAA---AAAAAAAA-----AAAAAAAAA-------AAAAAAAANNNNN--AAGGGNNNA-------ANUNAAU---
SEQ ID NO:116

I36: -GUUGGA---ACUUAGGAGUUNCCUGAGCGGGACGCGGGAUACAAGGG--UGGUAAACGU---GNNAAAA--AAAAAAA----AAAAAAA--------A--AAAAAUNANGGGA----CUNCUAACNN---CAAANAAAAA---U
SEQ ID NO:117

I30: CGUAAAAGGCUGAUCAGU--CCCAGGCUGGCUAGGCCUCUCGUGGGGGCUGGCUAGGCC----AAUCNAAAAAAAAAAAAA------AAAAAAAAAAAANN--NAANAANAAA--UGUUGCGGACU--G
SEQ ID NO:118

I39: -GUUGGA---GNUUAGGAAUUCCCUAANNGGGACGGGAANNNNAAGGG--CGGCCCCNGUNAAGANNNVNANUAAANAAAAA---AAGGAANAAAAAANAANANU--AANAAAAANNA---NAANAAGCGNNNU
SEQ ID NO:119
```

FIGURE 4 (cont.)

Phylogenetic Analysis of 3H biocatalysts

SEQUENCE LISTING

<160> NUMBER OF SEQ ID NOS: 120

<210> SEQ ID NO 1
<211> LENGTH: 147
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(147)
<223> OTHER INFORMATION: n is A,G,C, or T

<400> SEQUENCE: 1
gggagacaag aataaacgct caannnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnttcgaca ggaggctcac aacaggc                                        147

<210> SEQ ID NO 2
<211> LENGTH: 147
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(147)
<223> OTHER INFORMATION: n is A,G,C, or T

<400> SEQUENCE: 2
gggagatgct actactaaca acannnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnttcgaca ggaggctcac aacaggc                                        147

<210> SEQ ID NO 3
<211> LENGTH: 147
<212> TYPE: DNA
<213> ORGANISM: Artificial Sequence
<220> FEATURE:
<223> OTHER INFORMATION: Synthetic Sequence
<220> FEATURE:

<221> NAME/KEY: misc_feature
<222> LOCATION: (1)..(147)
<223> OTHER INFORMATION: n is A,G,C, or T

<400> SEQUENCE: 3
gggaggaaac atcacaatcc atannnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnttcgaca ggaggctcac aacaggc                                       147

<210> SEQ ID NO 4
<211> LENGTH: 147
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(147)
<223> OTHER INFORMATION: n is A,G,C, or T

<400> SEQUENCE: 4
gggagataat aaatgcccag agannnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnttcgaca ggaggctcac aacaggc                                       147

<210> SEQ ID NO 5
<211> LENGTH: 147
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(147)
<223> OTHER INFORMATION: n is A,G,C, or T

<400> SEQUENCE: 5
gggagaaata caaataggca ggannnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnttcgaca ggaggctcac aacaggc                                       147

<210> SEQ ID NO 6
<211> LENGTH: 147
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(147)
<223> OTHER INFORMATION: n is A,G,C, or T

<400> SEQUENCE: 6
gggagaactt attattcacc cgannnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnttcgaca ggaggctcac aacaggc                                       147

<210> SEQ ID NO 7
<211> LENGTH: 147
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(147)
<223> OTHER INFORMATION: n is A,G,C, or T

<400> SEQUENCE: 7
gggagactat ttatcatacg gcannnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnttcgaca ggaggctcac aacaggc                                       147

<210> SEQ ID NO 8
<211> LENGTH: 147
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(147)
<223> OTHER INFORMATION: n is A,G,C, or T

<400> SEQUENCE: 8
gggagaatca aagtaatcgc tcannnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnttcgaca ggaggctcac aacaggc                                       147

<210> SEQ ID NO 9
<211> LENGTH: 147
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(147)
<223> OTHER INFORMATION: n is A,G,C, or T

<400> SEQUENCE: 9
gggagaccta agcatctaaa ctannnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnttcgaca ggaggctcac aacaggc                                       147

<210> SEQ ID NO 10
<211> LENGTH: 147
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(147)
<223> OTHER INFORMATION: n is A,G,C, or T

<400> SEQUENCE: 10
gggagaaggt agtagtagaa gatnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnttcgaca ggaggctcac aacaggc                                       147

<210> SEQ ID NO 11
<211> LENGTH: 40
<212> TYPE: DNA
<213> ORGANISM: Artificial Sequence
<220> FEATURE:

<223> OTHER INFORMATION: Synthetic Sequence

<400> SEQUENCE: 11
taatacgact cactataggg agacaagaat aaacgctcaa                          40

<210> SEQ ID NO 12
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 12
taatacgact cactataggg agatgctact actaacaaca                          40

<210> SEQ ID NO 13
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 13
taatacgact cactataggg aggaaacatc acaatccata                          40

<210> SEQ ID NO 14
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 14
taatacgact cactataggg agataataaa tgcccagaga                          40

<210> SEQ ID NO 15
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 15
taatacgact cactataggg agaaatacaa ataggcagga                          40

<210> SEQ ID NO 16
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 16
taatacgact cactataggg agaacttatt attcacccga                          40

<210> SEQ ID NO 17
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 17
taatacgact cactataggg agactatttta tcatacggca                         40

-continued

```
<210> SEQ ID NO 18
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 18
taatacgact cactataggg agaatcaaag taatcgctca                40

<210> SEQ ID NO 19
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 19
taatacgact cactataggg agacctaagc atctaaacta                40

<210> SEQ ID NO 20
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 20
taatacgact cactataggg agaaggtagt agtagaagat                40

<210> SEQ ID NO 21
<211> LENGTH: 10
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: 5' nucleotide is conjugated to diene reactant 1
      or 2 via 2000MW PEG linker

<400> SEQUENCE: 21
aaaccacccc                                                 10

<210> SEQ ID NO 22
<211> LENGTH: 10
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: 5' nucleotide is conjugated to diene reactant 3
      or 4 via 2000MW PEG linker

<400> SEQUENCE: 22
ccaggcacgc                                                 10

<210> SEQ ID NO 23
<211> LENGTH: 10
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
```

<223> OTHER INFORMATION: 5' nucleotide is conjugated to diene reactant 5
      or 6 via 2000MW PEG linker

<400> SEQUENCE: 23
ctcctccttt                                                              10

<210> SEQ ID NO 24
<211> LENGTH: 10
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: 5' nucleotide is conjugated to diene reactant 7
      or 8 via 2000MW PEG linker

<400> SEQUENCE: 24
gaggagggag                                                              10

<210> SEQ ID NO 25
<211> LENGTH: 10
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: 5' nucleotide is conjugated to diene reactant 9
      or 10 via 2000MW PEG linker

<400> SEQUENCE: 25
gtgttgggtg                                                              10

<210> SEQ ID NO 26
<211> LENGTH: 10
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: 5' nucleotide is conjugated to diene reactant
      11 or 12 via 2000MW PEG linker

<400> SEQUENCE: 26
cacgcgacac                                                              10

<210> SEQ ID NO 27
<211> LENGTH: 10
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: 5' nucleotide is conjugated to diene reactant
      13 or 14 via 2000MW PEG linker

<400> SEQUENCE: 27
tttcggcggg                                                              10

<210> SEQ ID NO 28
<211> LENGTH: 10
<212> TYPE: DNA
<213> ORGANISM: Artificial Sequence

```
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: 5' nucleotide is conjugated to diene reactant
      15 or 16 via 2000MW PEG linker

<400> SEQUENCE: 28
gggtggtaaa                                                          10

<210> SEQ ID NO 29
<211> LENGTH: 10
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: 5' nucleotide is conjugated to diene reactant
      17 or 18 via 2000MW PEG linker

<400> SEQUENCE: 29
ccctctcata                                                          10

<210> SEQ ID NO 30
<211> LENGTH: 10
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: 5' nucleotide is conjugated to diene reactant
      19 or 20 via 2000MW PEG linker

<400> SEQUENCE: 30
atagcggctc                                                          10

<210> SEQ ID NO 31
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 31
cttgtctccc ggggtggttt                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 32
agcatctccc gcgtgcctgg                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 33
```

```
gtttcctccc aaaggaggag                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 34
attatctccc ctccctcctc                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 35
tatttctccc cacccaacac                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 36
aagttctccc gtgtcgcgtg                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 37
atagtctccc cccgccgaaa                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 38
tgattctccc tttaccaccc                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 39
taggtctccc tatgagaggg                                              20

<210> SEQ ID NO 40
<211> LENGTH: 20
<212> TYPE: DNA
```

```
<213> ORGANISM: Artificial Sequence
<220> FEATURE:
<223> OTHER INFORMATION: Synthetic Sequence

<400> SEQUENCE: 40
accttctccc gagccgctat                                                    20

<210> SEQ ID NO 41
<211> LENGTH: 119
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(119)
<223> OTHER INFORMATION: U is 5-(4-pyridylmethyl)U

<400> SEQUENCE: 41
gacaagaaua aacgcuuaag ccgacaguga ggagcgguga ugcagggcug gugcgugcag         60
gucggcucag gacccgagua agugguggcu aagugugagg gugacucguc gaauagaag         119

<210> SEQ ID NO 42
<211> LENGTH: 120
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(120)
<223> OTHER INFORMATION: U is 5-(4-pyridylmethyl)U

<400> SEQUENCE: 42
gacaagaaua aacgcucaag ccaacaguga ggggcgguga ugcggggcug gugcgugcag         60
ggucgguuca ggacccgagu aagugguggc uaagugugag ggugacucau cgaauagagg        120

<210> SEQ ID NO 43
<211> LENGTH: 119
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(119)
<223> OTHER INFORMATION: U is 5-(4-pyridylmethyl)U

<400> SEQUENCE: 43
gacaagaaua aacgcucaag ccaacaguga ggagcgguga ugcggggcug gugcgugcag         60
gucgguucag gacccgagua agugguggcu aagugugagg gugacuuguc gaauagaag         119

<210> SEQ ID NO 44
<211> LENGTH: 118
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(118)
<223> OTHER INFORMATION: U is 5-(4-pyridylmethyl)U

<400> SEQUENCE: 44
gacaagaaua aacgcucaag ccaacaguga ggagcgguga ugcggggcug gucgugcagg         60
ucgguucagg acccgaguaa gugguggcua agugugaggg ugacucgucg aauagaag          118
```

<210> SEQ ID NO 45
<211> LENGTH: 117
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(117)
<223> OTHER INFORMATION: U is 5-(4-pyridylmethyl)U

<400> SEQUENCE: 45
gacaagaaua aacgcucaag ccaacaguga ggagcgauga ugcggcuggu gcgugcaggu     60
cgguucagga cccgaguaag ugguggcuaa gugugagggu gacucgucga auagaag       117

<210> SEQ ID NO 46
<211> LENGTH: 119
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(119)
<223> OTHER INFORMATION: U is 5-(4-pyridylmethyl)U

<400> SEQUENCE: 46
gacaagaaua aacgcucaag ccaacaguga ggagcgguga ugcagggcug gugcgugcag     60
gucgguucag gacccgagua aguggugggu gugacucguc gaauagaag                119

<210> SEQ ID NO 47
<211> LENGTH: 119
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(119)
<223> OTHER INFORMATION: U is 5-(4-pyridylmethyl)U

<400> SEQUENCE: 47
gacaagaaua aacgcucaag ccaacaguga ggagugguga ugcggggcug gugcgugcag     60
gucgguucag gacccgagua aguggugggu aagugugagg gugacucguc gaacagaag     119

<210> SEQ ID NO 48
<211> LENGTH: 119
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(119)
<223> OTHER INFORMATION: U is 5-(4-pyridylmethyl)U

<400> SEQUENCE: 48
gacaagaaua aacgcccaag ccagcaguga ggagcgguga ugcggggcug gugcgugcag     60
gucgguucaa gacccgagua aguggugggu aagugugagg gugacucguc gaauagaag     119

<210> SEQ ID NO 49
<211> LENGTH: 100
<212> TYPE: RNA
<213> ORGANISM: Artificial Sequence
<220> FEATURE:

<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U
<220> FEATURE:
<221> NAME/KEY: misc_feature
<222> LOCATION: (1)..(100)
<223> OTHER INFORMATION: n is A,G,C, or 5-(4-pyridylmethyl)U

<400> SEQUENCE: 49
gccaacagug aggagcggug augcggggcu gaugcgugca ggucgguuca ggacccgagu    60 aaguggugc uaagugugag ggugacucnu cgaauauaag                           100

<210> SEQ ID NO 50
<211> LENGTH: 102
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(102)
<223> OTHER INFORMATION: N is A,G,C, or 5-(4-pyridylmethyl)U
<220> FEATURE:
<221> NAME/KEY: modified_base
<222> LOCATION: (1)..(102)
<223> OTHER INFORMATION: U is 5-(4-pyridylmethyl)U

<400> SEQUENCE: 50
gccaacagug aggagcnggu aaugcggggc uggugcgugc aggucgguuc agnccccgagu   60 aaguggugc uaagugunag ggugacucag ccagaauaga ag                       102

<210> SEQ ID NO 51
<211> LENGTH: 100
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U

<400> SEQUENCE: 51
gcuagcaggu ugagggagua cuacguuggu ugagguaggg agaggcugac ugcugaggac   60
uacaggcuau ggcuaguaua augcgccacg ggaauaacug                         100

<210> SEQ ID NO 52
<211> LENGTH: 100
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U

<400> SEQUENCE: 52
acgugagaac uaccggggau ggggcugagu cggaaagugg aagccucuga uccgcuggac   60
cugggauaag cccagaggaa gcgguagggg guagcaaaac                         100

<210> SEQ ID NO 53
<211> LENGTH: 100
<212> TYPE: RNA
<213> ORGANISM: Artificial Sequence

```
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U

<400> SEQUENCE: 53
ugcucacccg auaugcaucg gaguagaggu uguagguaac gaugcggcgu aaucggugag      60
ggcgugaacu agagacgacg gugaaggugg gugcgugagg                          100

<210> SEQ ID NO 54
<211> LENGTH: 100
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U
<220> FEATURE:
<221> NAME/KEY: misc_feature
<222> LOCATION: (1)..(100)
<223> OTHER INFORMATION: N is A,G,C, or 5-(4-pyridylmethyl)U

<400> SEQUENCE: 54
acccgnaaga uugccuggua guggucgguc acgagaagug ggucggcuug gcgguuagag      60 uagggccac uagucaacuu gacgnaacag gggcgggcan                           100

<210> SEQ ID NO 55
<211> LENGTH: 100
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U
<220> FEATURE:
<221> NAME/KEY: misc_feature
<222> LOCATION: (1)..(100)
<223> OTHER INFORMATION: N is A,G,C, or U is (4-pyridylmethyl)U

<400> SEQUENCE: 55
gaacugccga aucgacuagg uaaagnagau gucgcugnag gnaagguugc caggagugua      60
ggacaugugu cgcagcugcc caucaggggc aaaugaucca                          100

<210> SEQ ID NO 56
<211> LENGTH: 100
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U

<400> SEQUENCE: 56
ggucagcugu acuagcuggu gggggugacc cccuacgaga gcgaauaacg ggagaauugc      60
cuaguuuggg ugcaaggauc aauggccgcu cuccgggggc                          100

<210> SEQ ID NO 57
<211> LENGTH: 99
<212> TYPE: RNA
```

<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(99)
<223> OTHER INFORMATION: U is 5-(4-pyridylmethyl)U

<400> SEQUENCE: 57
accucggugg aggcuaccgg uuacgccggg gggaucgcug ugcgcugcga gacuauaugg    60 uuggguaaa ugggagaugg ccgcucgagg cagucuggc                            99

<210> SEQ ID NO 58
<211> LENGTH: 101
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(101)
<223> OTHER INFORMATION: N is A,G,C, or 5-(4-pyridylmethyl)U
<220> FEATURE:
<221> NAME/KEY: modified_base
<222> LOCATION: (1)..(101)
<223> OTHER INFORMATION: U is 5-(4-pyridylmethyl)U

<400> SEQUENCE: 58
unggngccua agcacaagag gncgauggcu cnnccgcguu gnuggggaga cgugagganu    60
angcngagug nngcaacugu aggagcuugg ggaaacacua g                       101

<210> SEQ ID NO 59
<211> LENGTH: 100
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U

<400> SEQUENCE: 59
aggaguguug ccgggacgaa cucgaacggu guuccggaga ggagucuagg caucauaggg    60
agauugagug ggagugugcc agcgauucgg acggcgaacg                         100

<210> SEQ ID NO 60
<211> LENGTH: 98
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(98)
<223> OTHER INFORMATION: U is 5-(4-pyridylmethyl)U
<220> FEATURE:
<221> NAME/KEY: misc_feature
<222> LOCATION: (1)..(98)
<223> OTHER INFORMATION: N is A,G,C, or 5-(4-pyridylmethyl)U

<400> SEQUENCE: 60
ucgguggcag gggcgcgcgu ggcugacuau acgacugucu aacugacuua gugauggccu    60
gcugcgggaa acgaagnccc acaguggggc gguanaag                            98

<210> SEQ ID NO 61
<211> LENGTH: 100

```
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U

<400> SEQUENCE: 61
agcgccgagg uuagcuggau ugacguaguc uucgauaacc acacuaaggc ggcgaccugg      60
auaauaggua gcacgccaaa gggggcggcg cggggauugc                          100

<210> SEQ ID NO 62
<211> LENGTH: 129
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(129)
<223> OTHER INFORMATION: U is 5-(4-pyridylmethyl)U
<220> FEATURE:
<221> NAME/KEY: misc_feature
<222> LOCATION: (1)..(129)
<223> OTHER INFORMATION: N is A,G,C, or 5-(4-pyridylmethyl)U

<400> SEQUENCE: 62
caggagauaa unaaugnccn ganaccccug gaaaaaagga uggucguuga agguugyguu      60
gucgccgguc ggncaguaaa cuggauacgg gucgcgcacu aaaganugga uunuggaacc     120
gcguuugga                                                            129

<210> SEQ ID NO 63
<211> LENGTH: 101
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(101)
<223> OTHER INFORMATION: U is 5-(4-pyridylmethyl)U

<400> SEQUENCE: 63
aggugagggg agaaugccug uugagccggg ccaugcggag ggcgcaggcu cuaccguucc      60
acagcuuugu ggccuaguag gucggcauug aaugauggcg c                        101

<210> SEQ ID NO 64
<211> LENGTH: 99
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(99)
<223> OTHER INFORMATION: U is 5-(4-pyridylmethyl)U

<400> SEQUENCE: 64 gacggguugaa cugccacucg agccugugag aaaccguucg gucggaagac guaaauacga     60
acgaacaacu guuaggggua agucacuugc ugacuuacg                            99

<210> SEQ ID NO 65
<211> LENGTH: 99
<212> TYPE: RNA
```

```
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(99)
<223> OTHER INFORMATION: U is 5-(4-pyridylmethyl)U

<400> SEQUENCE: 65 gacggugaa cugccucucg agccugugag aaaccguucg gucggaagac guaaauacga    60
acgaacaacu guuaggggua agucacuugc ugacuuacg                          99

<210> SEQ ID NO 66
<211> LENGTH: 100
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U

<400> SEQUENCE: 66
acauguggag gggaauugcc uagugguggg aggucggagc ggaacagcgu ggcgucgucu    60
gacaaacagg cggaggccgg uguugcgcuc caggaugugg                         100

<210> SEQ ID NO 67
<211> LENGTH: 100
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U
<220> FEATURE:
<221> NAME/KEY: misc_feature
<222> LOCATION: (1)..(100)
<223> OTHER INFORMATION: N is A,G,C, or 5-(4-pyridylmethyl)U

<400> SEQUENCE: 67
ccgaguggga auacuguagg cgangccngg gngcauguga ugcugaugag gaaganuaca    60
uuncgagacc uacugucgga ggggngaung gagngcucca                         100

<210> SEQ ID NO 68
<211> LENGTH: 101
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(101)
<223> OTHER INFORMATION: U is 5-(4-pyridylmethyl)U
<220> FEATURE:
<221> NAME/KEY: misc_feature
<222> LOCATION: (1)..(101)
<223> OTHER INFORMATION: N is A,G,C, or 5-(4-pyridylmethyl)U

<400> SEQUENCE: 68
gguacaccac gngagacugg guguggcca ccccggcgcu cgcaacgacu uguuacucuc     60
gugaguccuu aaacgugagu ugcuugaagg ucguguaguu g                      101

<210> SEQ ID NO 69
<211> LENGTH: 99
```

<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(99)
<223> OTHER INFORMATION: U is 5-(4-pyridylmethyl)U
<220> FEATURE:
<221> NAME/KEY: misc_feature
<222> LOCATION: (1)..(99)
<223> OTHER INFORMATION: N is A,G,C, or  5-(4-pyridylmethyl)U

<400> SEQUENCE: 69
ggaguuccag uagagugacg cuggagugcu gcgcggaagc uaggucagcu ggugcccaau      60
gagggcgugc ggggugggna gaucaugccu cggggaucc                            99

<210> SEQ ID NO 70
<211> LENGTH: 99
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(99)
<223> OTHER INFORMATION: U is 5-(4-pyridylmethyl)U
<220> FEATURE:
<221> NAME/KEY: misc_feature
<222> LOCATION: (1)..(99)
<223> OTHER INFORMATION: N is A,G,C, or  5-(4-pyridylmethyl)U

<400> SEQUENCE: 70
cucgugugau cggucagggg gcguugnaac uaccguaaga ggguggggga gaacunccuu      60
guaugugcca aaaggaccug ucugaccgcg gagccggcu                             99

<210> SEQ ID NO 71
<211> LENGTH: 101
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(101)
<223> OTHER INFORMATION: U is 5-(4-pyridylmethyl)U

<400> SEQUENCE: 71
auccuguagg ggugagucaa ggaggguguc agaauuccua guugcgaauu agcugagguc      60
cggguguuca aaacgggaag gugcugcaug aggggaguag c                         101

<210> SEQ ID NO 72
<211> LENGTH: 104
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(104)
<223> OTHER INFORMATION: U is 5-(4-pyridylmethyl)U
<220> FEATURE:
<221> NAME/KEY: misc_feature
<222> LOCATION: (1)..(104)
<223> OTHER INFORMATION: N is A,G,C, or  5-(4-pyridylmethyl)U

<400> SEQUENCE: 72
ggugacccua cagggcaunu ggguccgaga acuaaaaaaa aaaggacaug cgaccuuncg      60

-continued

<210> SEQ ID NO 73
<211> LENGTH: 100
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U
<220> FEATURE:
<221> NAME/KEY: misc_feature
<222> LOCATION: (1)..(100)
<223> OTHER INFORMATION: N is A,G,C, or 5-(4-pyridylmethyl)U

<400> SEQUENCE: 73
caugggguga cguggagcgg gcaauugaug gauccnaguu agggugccag uagugaguca    60
acgaauucgg cguuccgagg uuuaaccaga aaugccucug                         100

<210> SEQ ID NO 74
<211> LENGTH: 101
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(101)
<223> OTHER INFORMATION: U is 5-(4-pyridylmethyl)U
<220> FEATURE:
<221> NAME/KEY: misc_feature
<222> LOCATION: (1)..(101)
<223> OTHER INFORMATION: N is A,G,C, or 5-(4-pyridylmethyl)U

<400> SEQUENCE: 74
uggauuugau gagcuaaccu cgagacuaag cugcacgaca guggagacuc aagggugaau    60
ugcgugcuug cgggcgaugc ggaagcgagg gaucuncugg u                       101

<210> SEQ ID NO 75
<211> LENGTH: 120
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(120)
<223> OTHER INFORMATION: U is 5-(4-pyridylmethyl)U

<400> SEQUENCE: 75
ugugcaagaa uaaacgcuca agcguggacu cgaagcagca uuuagcgcuc gguacaucga    60
gggagggagg acuaguuuac ggucauauag gcuugccuga gcgaacgggg ggccccgcug   120

<210> SEQ ID NO 76
<211> LENGTH: 101
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(101)
<223> OTHER INFORMATION: U is 5-(4-pyridylmethyl)U
<220> FEATURE:
<221> NAME/KEY: misc_feature
<222> LOCATION: (1)..(101)
<223> OTHER INFORMATION: N is A,G,C, or 5-(4-pyridylmethyl)U

<400> SEQUENCE: 76
nngccgauug gcacggguca ncuggcuguu gaugacuggg gcggauncug uccccggau    60 agcuagcgga gagauggaau gcccgcnucg gcaauuggcg c    101

<210> SEQ ID NO 77
<211> LENGTH: 116
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(116)
<223> OTHER INFORMATION: U is 5-(4-pyridylmethyl)U

<400> SEQUENCE: 77
ccuaagcauc uaaacuagau cguaaggguu uuagggccag gugagcgagg ugagggagac    60
gccggagcga uugcauggcc ccgagagaua ggguugcaag cugagcaaga gguggg    116

<210> SEQ ID NO 78
<211> LENGTH: 101
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(101)
<223> OTHER INFORMATION: U is 5-(4-pyridylmethyl)U

<400> SEQUENCE: 78
ggugggcaag uugguaccga guuacuccgg ucgugcacuc acaggagcga ugacgaagua    60
ccacgggaga gaugugagug uuggcuggca gagaaauagc g    101

<210> SEQ ID NO 79
<211> LENGTH: 102
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(102)
<223> OTHER INFORMATION: U is 5-(4-pyridylmethyl)U
<220> FEATURE:
<221> NAME/KEY: misc_feature
<222> LOCATION: (1)..(102)
<223> OTHER INFORMATION: N is A,G,C, or 5-(4-pyridylmethyl)U

<400> SEQUENCE: 79
aucaaggugg augggcaacu ggggacugc cggggcgug accuaaggag agaggaugug    60
ccuggagcau agcuugguaa uggcuacgga cggagaacau nc    102

<210> SEQ ID NO 80
<211> LENGTH: 100
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U
<220> FEATURE:
<221> NAME/KEY: misc_feature
<222> LOCATION: (1)..(100)

<223> OTHER INFORMATION: N is A,G,C, or 5-(4-pyridylmethyl)U

<400> SEQUENCE: 80
cggggucgga gaaugccugu nuuggaagca gcgguccgcu uggaccucug agagguaggg    60
agcuacncac agacggagcu guccacuacc agaugugacc                        100

<210> SEQ ID NO 81
<211> LENGTH: 100
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U
<220> FEATURE:
<221> NAME/KEY: misc_feature
<222> LOCATION: (1)..(100)
<223> OTHER INFORMATION: N is A,G,C, or 5-(4-pyridylmethyl)U

<400> SEQUENCE: 81
cggggcggun auagggunac acguuaangu auguguuacc uagaggaccu gaguauagaa    60
uaacgacgua gggagncugc auaaugggag aucucggggg                        100

<210> SEQ ID NO 82
<211> LENGTH: 100
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U
<220> FEATURE:
<221> NAME/KEY: misc_feature
<222> LOCATION: (1)..(100)
<223> OTHER INFORMATION: N is A,G,C, or 5-(4-pyridylmethyl)U

<400> SEQUENCE: 82
caggunuggg gacggagggu ggucgagcac cguguccucc cguggaggau ggagagcgag    60
gggagguucc uaugacgccu ucgaacgggg agucccguga                        100

<210> SEQ ID NO 83
<211> LENGTH: 101
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(101)
<223> OTHER INFORMATION: U is 5-(4-pyridylmethyl)U
<220> FEATURE:
<221> NAME/KEY: misc_feature
<222> LOCATION: (1)..(101)
<223> OTHER INFORMATION: N is A,G,C, or  5-(4-pyridylmethyl)U

<400> SEQUENCE: 83
uugguagggg cuggguggug ccgguuaggu gccgauagag aaacuaucca gcuccgcggu    60
uauggcggag nacuagucgg auuucgggcu aggaggcggu g                      101

<210> SEQ ID NO 84
<211> LENGTH: 101
<212> TYPE: RNA
<213> ORGANISM: Artificial Sequence

```
<220> FEATURE:
<223> OTHER INFORMATION: Synthetic Sequence
<220> FEATURE:
<221> NAME/KEY: modified_base
<222> LOCATION: (1)..(101)
<223> OTHER INFORMATION: U is 5-(4-pyridylmethyl)U
<220> FEATURE:
<221> NAME/KEY: misc_feature
<222> LOCATION: (1)..(101)
<223> OTHER INFORMATION: N is A,G,C, or 5-(4-pyridylmethyl)U

<400> SEQUENCE: 84
uugguagggc ugggguggugc cggguuaggu gccgauagag aaacuaucca gcuccgcggu     60
uauggcggag nacuagucgg auuucgggcu aggaggcggu g                        101

<210> SEQ ID NO 85
<211> LENGTH: 47
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(47)
<223> OTHER INFORMATION: U is 5-(4-pyridylmethyl)U

<400> SEQUENCE: 85
ggaggagggu gcggguggga gggcgcgaga agugggggcgu gaggugg                  47

<210> SEQ ID NO 86
<211> LENGTH: 100
<212> TYPE: RNA
<213> ORGANISM: Artificial Sequence
<220> FEATURE:
<223> OTHER INFORMATION: Synthetic Sequnce
<220> FEATURE:
<221> NAME/KEY: modified_base
<222> LOCATION: (1)..(100)
<223> OTHER INFORMATION: U is 5-(4-pyridylmethyl)U

<400> SEQUENCE: 86
guugcacgcg caauugguga cuccgugagg ggcgggggcc uccaccaagu gcugagugcg     60
cgauucaacc gagggggaugu cuuaaggucg guugcguguc                         100

<210> SEQ ID NO 87
<211> LENGTH: 113
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(113)
<223> OTHER INFORMATION: U is 5-(4-pyridylmethyl)U
<220> FEATURE:
<221> NAME/KEY: misc_feature
<222> LOCATION: (1)..(113)
<223> OTHER INFORMATION: N is A,G,C, or 5-(4-pyridylmethyl)U

<400> SEQUENCE: 87
guuggagcgu aggaguuccc ugagcgggac ggggaauaca agggcggcaa acgugaccga     60
naaunaccca aaccnanaag gnaggannna aacucnaacu aggaaaaann naa           113

<210> SEQ ID NO 88
<211> LENGTH: 100
<212> TYPE: RNA
<213> ORGANISM: Artificial Sequence
<220> FEATURE:
```

<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U

<400> SEQUENCE: 88 cugggcaau uccgguugg gaggauggcu uaaggagcuc cugagugagc aaagccucgg    60
uggggcccgg ggugugcug caaccgaggu gugaugcgca                         100

<210> SEQ ID NO 89
<211> LENGTH: 98
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(98)
<223> OTHER INFORMATION: U is 5-(4-pyridylmethyl)U
<220> FEATURE:
<221> NAME/KEY: misc_feature
<222> LOCATION: (1)..(98)
<223> OTHER INFORMATION: N is A,G,C, or 5-(4-pyridylmethyl)U

<400> SEQUENCE: 89
agguggggag acugccagag cugccaugcg cggcccaccg ugugggccga gcgauccggc    60
guagguacgn aggacacuug aacgauucgu aguaugga                           98

<210> SEQ ID NO 90
<211> LENGTH: 108
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(108)
<223> OTHER INFORMATION: U is 5-(4-pyridylmethyl)U
<220> FEATURE:
<221> NAME/KEY: misc_feature
<222> LOCATION: (1)..(108)
<223> OTHER INFORMATION: N is A,G,C, or 5-(4-pyridylmethyl)U

<400> SEQUENCE: 90
guuggagcuu angagccccu gagcgggacg gggagugcaa gguggcaaa cgugaaaaaa    60 aaaaaaaua naaaaaaaa ggaaaaaaaa aaaaaaaaaa aaaaaaag                  108

<210> SEQ ID NO 91
<211> LENGTH: 98
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(98)
<223> OTHER INFORMATION: U is 5-(4-pyridylmethyl)U

<400> SEQUENCE: 91
guuggagcuu aggaguuccc ugaguggac ggggaauaca gggguggcaa acgugaaaaa    60
aaaaaaaaaa aaaaaaaaa aaaaaaaaa aaaaaaau                             98

<210> SEQ ID NO 92
<211> LENGTH: 106
<212> TYPE: RNA
<213> ORGANISM: Artificial Sequence

```
<220> FEATURE:
<223> OTHER INFORMATION: Synthetic Sequence
<220> FEATURE:
<221> NAME/KEY: modified_base
<222> LOCATION: (1)..(106)
<223> OTHER INFORMATION: U is 5-(4-pyridylmethyl)U
<220> FEATURE:
<221> NAME/KEY: misc_feature
<222> LOCATION: (1)..(106)
<223> OTHER INFORMATION: N is A,G,C, or 5-(4-pyridylmethyl)U

<400> SEQUENCE: 92
guuggagcuu aagaguuccc ugagcaggac ggggaauaca angguggnaa acgugaaaaa      60
aaaaaaaaaa aaaaaaanaa annanannaa anggaaaaaa aanaau                   106

<210> SEQ ID NO 93
<211> LENGTH: 107
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(107)
<223> OTHER INFORMATION: U is 5-(4-pyridylmethyl)U

<400> SEQUENCE: 93
guuggagcuu aggagcuccc ugagcgggac ggggaauaca agggguggcag acgugaaaaa     60 aaaaaaaaa aaaggaaaaa aaaaaaaaaa aaaaaaaaaa aaaaaau                   107

<210> SEQ ID NO 94
<211> LENGTH: 111
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(111)
<223> OTHER INFORMATION: U is 5-(4-pyridylmethyl)U
<220> FEATURE:
<221> NAME/KEY: misc_feature
<222> LOCATION: (1)..(111)
<223> OTHER INFORMATION: N is A,G,C, or 5-(4-pyridylmethyl)U

<400> SEQUENCE: 94
guuggagcuu aggaguuccc ugagcgggac ggggaauacu agggcggcaa acgugaaaaa      60
aagaaaaaaa aaaaaaaaaa aaaaaaaaaa aaaaaaaaaa aaaaanccuc c             111

<210> SEQ ID NO 95
<211> LENGTH: 107
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(107)
<223> OTHER INFORMATION: U is 5-(4-pyridylmethyl)U

<400> SEQUENCE: 95
guuggggccu aggagcuccc ugagcgguac ggggaauaca aggguggcaa acgugaaaaa      60 agaaagaaa aaaaaaaaaa aaaaaaaaaa aaaaaaaaaa aaaaaau                   107

<210> SEQ ID NO 96
<211> LENGTH: 117
<212> TYPE: RNA
```

```
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(117)
<223> OTHER INFORMATION: U is 5-(4-pyridylmethyl)U
<220> FEATURE:
<221> NAME/KEY: misc_feature
<222> LOCATION: (1)..(117)
<223> OTHER INFORMATION: N is A,G,C, or 5-(4-pyridylmethyl)U

<400> SEQUENCE: 96
guuggagcuu aggagcuccc ugancgggac ggggaanaca aggguggcag acgunnaaaa      60
anaaagnaaa aaaaaaaaaa aaaaaaaaaa aaaaaaaaaa aaagaaaaaa aaaaaaa        117

<210> SEQ ID NO 97
<211> LENGTH: 120
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(120)
<223> OTHER INFORMATION: U is 5-(4-pyridylmethyl)U
<220> FEATURE:
<221> NAME/KEY: misc_feature
<222> LOCATION: (1)..(120)
<223> OTHER INFORMATION: N is A,G,C, or 5-(4-pyridylmethyl)U

<400> SEQUENCE: 97
guuggagcuu angaguuccc ugagcgggcc ggggaauaca aggguggcag acnugaaaaa      60
aaaaaaaaaa aaggaaggaa aaaaaaaaaa aaaaggaaaa annnaaaaan nnaaaaaaaa     120

<210> SEQ ID NO 98
<211> LENGTH: 112
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(112)
<223> OTHER INFORMATION: U is 5-(4-pyridylmethyl)U
<220> FEATURE:
<221> NAME/KEY: misc_feature
<222> LOCATION: (1)..(112)
<223> OTHER INFORMATION: N is A,G,C, or 5-(4-pyridylmethyl)U

<400> SEQUENCE: 98
guuggagcuu aggagcuccc ugagcgggac ggggaauaca aggguggcaa acgugaaaaa      60 aaagaaaaa aaaaaaaaaa aaaaaaaaaa aaanaaaaaa aaaaaaaaaa an             112

<210> SEQ ID NO 99
<211> LENGTH: 108
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(108)
<223> OTHER INFORMATION: U is 5-(4-pyridylmethyl)U
<220> FEATURE:
<221> NAME/KEY: misc_feature
<222> LOCATION: (1)..(108)
<223> OTHER INFORMATION: N is A,G,C, or 5-(4-pyridylmethyl)U

<400> SEQUENCE: 99
```

```
guuggagccu agnagcuccc unagcgggnu gaggaaunca agggugguaa ccgugaaaag    60 aaaaacccc aaaaaaaaaa aaaaaaaaaa aaaaanaaaa annnuuun                 108
```

<210> SEQ ID NO 100
<211> LENGTH: 107
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(107)
<223> OTHER INFORMATION: U is 5-(4-pyridylmethyl)U
<220> FEATURE:
<221> NAME/KEY: misc_feature
<222> LOCATION: (1)..(107)
<223> OTHER INFORMATION: N is A,G,C, or 5-(4-pyridylmethyl)U

<400> SEQUENCE: 100

```
guuggagcuu agnagcnccn unaacggnan gnggaaanca agggnggccn ccnuuuaaaa    60
aaaaaaaaaa aaaaaaaaaa aaaaaaaaaa aaaaaaaaaa anaaaaa                 107
```

<210> SEQ ID NO 101
<211> LENGTH: 111
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(111)
<223> OTHER INFORMATION: U is 5-(4-pyridylmethyl)U
<220> FEATURE:
<221> NAME/KEY: misc_feature
<222> LOCATION: (1)..(111)
<223> OTHER INFORMATION: N is A,G,C, or 5-(4-pyridylmethyl)U

<400> SEQUENCE: 101

```
guuggagcuu angggcuccc uguncgggac gggaacncn angggcnac cguuunaaa       60 aaaaaaaaaa aaaagnaaaa anaaaaaaaa aaaaaaaaaa aaaaaaaaaa g            111
```

<210> SEQ ID NO 102
<211> LENGTH: 114
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(114)
<223> OTHER INFORMATION: U is 5-(4-pyridylmethyl)U
<220> FEATURE:
<221> NAME/KEY: misc_feature
<222> LOCATION: (1)..(114)
<223> OTHER INFORMATION: N is A,G,C, or 5-(4-pyridylmethyl)U

<400> SEQUENCE: 102

```
guuggagcuu aggaguuccc unancgggac gggaanaca angguggcaa acgunnaaaa    60
aaagaaaaaa aaaaaaaaaa aaaaaaaaaa aaaaaaaaaa aaaaaannn auag          114
```

<210> SEQ ID NO 103
<211> LENGTH: 104
<212> TYPE: RNA
<213> ORGANISM: Artificial Sequence
<220> FEATURE:
<223> OTHER INFORMATION: Synthetic Sequence
<220> FEATURE:

<221> NAME/KEY: modified_base
<222> LOCATION: (1)..(104)
<223> OTHER INFORMATION: U is 5-(4-pyridylmethyl)U
<220> FEATURE:
<221> NAME/KEY: misc_feature
<222> LOCATION: (1)..(104)
<223> OTHER INFORMATION: N is A,G,C, or 5-(4-pyridylmethyl)U

<400> SEQUENCE: 103
guuggagcuu aggaguuccc ugagugggac ggggaauaua aggggcaaa cgugaaaaaa    60 aaaaaaaaaa annaaaaaaa aggaaaaaaa aaaaaaaaaa aaan                  104

<210> SEQ ID NO 104
<211> LENGTH: 105
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(105)
<223> OTHER INFORMATION: U is 5-(4-pyridylmethyl)U
<220> FEATURE:
<221> NAME/KEY: misc_feature
<222> LOCATION: (1)..(105)
<223> OTHER INFORMATION: N is A,G,C, or 5-(4-pyridylmethyl)U

<400> SEQUENCE: 104
guuggagcuu aggagcuccc ugagcgggau gggaauaca agggcggcaa acgugaaaaa    60
aaaaangaaa aaaaaaaaaa naaaaaaaaa aaaaaagga aaaag                  105

<210> SEQ ID NO 105
<211> LENGTH: 104
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(104)
<223> OTHER INFORMATION: U is 5-(4-pyridylmethyl)U
<220> FEATURE:
<221> NAME/KEY: misc_feature
<222> LOCATION: (1)..(104)
<223> OTHER INFORMATION: N is A,G,C, or 5-(4-pyridylmethyl)U

<400> SEQUENCE: 105
guuggagcuu angaguuccc ugagcgggac ggggaauaca aggggcaga cgugaaaaaa    60 cnaaaaaaaa aaaaaaaaaa aaaaannnna aaaaaaaaaa aauu                  104

<210> SEQ ID NO 106
<211> LENGTH: 103
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(103)
<223> OTHER INFORMATION: U is 5-(4-pyridylmethyl)U

<400> SEQUENCE: 106
guuggagcuu aggagcuccu cgagcgggag gggaaugcga ggguggcaaa cgagaaaaaa    60
aaaaaaaaaa aaaaaaaaaa aaaaaaaaaa aaaaaaaaaa auu                   103

<210> SEQ ID NO 107
<211> LENGTH: 106

```
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(106)
<223> OTHER INFORMATION: U is 5-(4-pyridylmethyl)U
<220> FEATURE:
<221> NAME/KEY: misc_feature
<222> LOCATION: (1)..(106)
<223> OTHER INFORMATION: N is A,G,C,or 5-(4-pyridylmethyl)U

<400> SEQUENCE: 107
uaaunugguu ccggaaaaun unaagguguc ccuaaguuaa aaaaaaaaaa aaaaaaaaaa      60
aaaaaaaaaa aaaaaaaaaa aaaanaaagg ucuucagcug acgcau                   106

<210> SEQ ID NO 108
<211> LENGTH: 107
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(107)
<223> OTHER INFORMATION: U is 5-(4-pyridylmethyl)U
<220> FEATURE:
<221> NAME/KEY: misc_feature
<222> LOCATION: (1)..(107)
<223> OTHER INFORMATION: N is A,G,C, or 5-(4-pyridylmethyl)U

<400> SEQUENCE: 108
uaaunugguu ccggaaaaun unaagguguc ccuaaguuaa aaaaaaaaaa aaaaaaaaaa      60
aaaaaaaaaa aaaaaaaaaa aaaaaaaagg gucuucagcu gacgcau                  107

<210> SEQ ID NO 109
<211> LENGTH: 104
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(104)
<223> OTHER INFORMATION: U is 5-(4-pyridylmethyl)U
<220> FEATURE:
<221> NAME/KEY: misc_feature
<222> LOCATION: (1)..(104)
<223> OTHER INFORMATION: N is A,G,C, or 5-(4-pyridylmethyl)U

<400> SEQUENCE: 109
uaaugngguu acgnaaaaun ugaagggnuc ccuaaguaaa agaaaaaaaa anaaagnana      60
aaaaaaaaaa aaaaaaaaaa annaangguc uucaguugac gcau                    104

<210> SEQ ID NO 110
<211> LENGTH: 108
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(108)
<223> OTHER INFORMATION: U is 5-(4-pyridylmethyl)U
<220> FEATURE:
<221> NAME/KEY: misc_feature
<222> LOCATION: (1)..(108)
<223> OTHER INFORMATION: N is A,G,C, or 5-(4-pyridylmethyl)U
```

```
<400> SEQUENCE: 110
caaugugguu ccggaagaug ugaaggeguc ccuaagunaa aaaaaaaaa aaaaaaaaa      60 aaaggaaaaa aaaaaaaaaa aaaaaaaaan ggucuucagc ugacgcau                108

<210> SEQ ID NO 111
<211> LENGTH: 104
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(104)
<223> OTHER INFORMATION: U is 5-(4-pyridylmethyl)U
<220> FEATURE:
<221> NAME/KEY: misc_feature
<222> LOCATION: (1)..(104)
<223> OTHER INFORMATION: N is A,G,C,or 5-(4-pyridylmethyl)U

<400> SEQUENCE: 111
uaaugugguu ccggaagaug ugaaggeguc ccuaagccaa aaaaaanaaa aanaaaaaaa     60
aanaaaaaaa aaaaaaaaaa aaaaanggun uunagnugac ncau                    104

<210> SEQ ID NO 112
<211> LENGTH: 110
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(110)
<223> OTHER INFORMATION: U is 5-(4-pyridylmethyl)U
<220> FEATURE:
<221> NAME/KEY: misc_feature
<222> LOCATION: (1)..(110)
<223> OTHER INFORMATION: N is A,G,C,or 5-(4-pyridylmethyl)U

<400> SEQUENCE: 112
uaaugugguu ccggaagaug uggaggeguc ccuaaguaaa aaagaaaaaa aaaaaaaaaa     60
aaaaaanngg aaaaaaanaa aaaaaaaaaa aaggucuuca gcugccgcau              110

<210> SEQ ID NO 113
<211> LENGTH: 109
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(109)
<223> OTHER INFORMATION: U is 5-(4-pyridylmethyl)U
<220> FEATURE:
<221> NAME/KEY: misc_feature
<222> LOCATION: (1)..(109)
<223> OTHER INFORMATION: N is A,G,C, or 5-(4-pyridylmethyl)U

<400> SEQUENCE: 113
guuggagcuu aggagcuccc ugagcgggac agggaauaca aggguggcau acgugaaaaa     60
agaaangaaa aaaaaaaana nannnnnnnn nnngggggaa aaaaaaag               109

<210> SEQ ID NO 114
<211> LENGTH: 107
<212> TYPE: RNA
<213> ORGANISM: Artificial Sequence
<220> FEATURE:
<223> OTHER INFORMATION: Synthetic Sequence
```

```
<220> FEATURE:
<221> NAME/KEY: modified_base
<222> LOCATION: (1)..(107)
<223> OTHER INFORMATION: U is 5-(4-pyridylmethyl)U
<220> FEATURE:
<221> NAME/KEY: misc_feature
<222> LOCATION: (1)..(107)
<223> OTHER INFORMATION: N is A,G,C, or 5-(4-pyridylmethyl)U

<400> SEQUENCE: 114
guuggagcuu aagagcuccc ugaguggaac gggaauaca agggugcaa acgugaaaaa       60 aaaaaaaaaa aaaaannnna ccnnunnaaa nnaaanaaaa aaaaanu                  107

<210> SEQ ID NO 115
<211> LENGTH: 109
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(109)
<223> OTHER INFORMATION: U is 5-(4-pyridylmethyl)U
<220> FEATURE:
<221> NAME/KEY: misc_feature
<222> LOCATION: (1)..(109)
<223> OTHER INFORMATION: N is A,G,C, or 5-(4-pyridylmethyl)U

<400> SEQUENCE: 115
guuggagcuu angagccccu gagcgggacg gggagugcaa ggguggcaaa cgugaaaaaa     60
aaaaaanaaa aanaancuun nggaannaaa nnaaauaaaa aaaauacng               109

<210> SEQ ID NO 116
<211> LENGTH: 100
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(100)
<223> OTHER INFORMATION: U is 5-(4-pyridylmethyl)U
<220> FEATURE:
<221> NAME/KEY: misc_feature
<222> LOCATION: (1)..(100)
<223> OTHER INFORMATION: N is A,G,C, or 5-(4-pyridylmethyl)U

<400> SEQUENCE: 116
guuggagcuu angagcuccc ugagcaggac gggaauaca aggguggcaa acguggaaaa      60
aaaaaaaaaa aaaaaaaann nnnaagggnn nnaanunaau                         100

<210> SEQ ID NO 117
<211> LENGTH: 104
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(104)
<223> OTHER INFORMATION: U is 5-(4-pyridylmethyl)U
<220> FEATURE:
<221> NAME/KEY: misc_feature
<222> LOCATION: (1)..(104)
<223> OTHER INFORMATION: N is A,G,C, or 5-(4-pyridylmethyl)U

<400> SEQUENCE: 117
guuggaacuu aggaguuncc ugagcgggac ggggaauaca agggugguaa acgugnnaaa     60
```
aaaaaaaaaa aaaaaunang ggacuncuaa cnncaaanaa aaau         104

<210> SEQ ID NO 118
<211> LENGTH: 112
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(112)
<223> OTHER INFORMATION: U is 5-(4-pyridylmethyl)U
<220> FEATURE:
<221> NAME/KEY: misc_feature
<222> LOCATION: (1)..(112)
<223> OTHER INFORMATION: N is A,G,C, or 5-(4-pyridylmethyl)U

<400> SEQUENCE: 118
cguuaaaagg cugaucaguc ccaggcuggc uaggccucuc gugggcugg gucuccaauc    60 naaaaaaaaa aaaaaaaaaa aaaaaanann naanaanaaa uguugcggac ug          112

<210> SEQ ID NO 119
<211> LENGTH: 117
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(117)
<223> OTHER INFORMATION: U is 5-(4-pyridylmethyl)U
<220> FEATURE:
<221> NAME/KEY: misc_feature
<222> LOCATION: (1)..(117)
<223> OTHER INFORMATION: N is A,G,C, or 5-(4-pyridylmethyl)U

<400> SEQUENCE: 119
guuggagnuu aggaauuccc uaanngggac ggggaannna aggggggccc cngunaagan    60
nnanuaaana aaaaaaagga anaaaaanaa nanuaanaaa annanaanaa gcgnnnu      117

<210> SEQ ID NO 120
<211> LENGTH: 97
<212> TYPE: RNA
<213> ORGANISM: Artificial Sequence
<220> FEATURE:
<221> NAME/KEY: modified_base
<222> LOCATION: (1)..(97)
<223> OTHER INFORMATION: U is 5-(4-pyridylmethyl) uridine)
<220> FEATURE:
<221> NAME/KEY: misc_feature
<222> LOCATION: (1)..(97)
<223> OTHER INFORMATION: N is A,G,C, or 5-(4-pyridylmethyl) uridine)

<400> SEQUENCE: 120
gggcugacgc gcgucaguag uuuacuguca ggugcggcua uacuaggaag caaggugggc    60
ucucgagucu agggnagauu ggauguaguu ggguagc                             97

ANTIBIOTIC COMPOUNDS

FIELD OF THE INVENTION

The present invention relates to antibiotic compounds, especially those effective against methicilin-resistant *Staphylococcus aureus*, and methods for their preparation.

BACKGROUND OF THE INVENTION

Methicillin-resistant *Staphylococcus aureus* (MRSA) is a prevalent and rapidly growing nosocomial pathogen problem. Not only has the incidence of MRSA among hospital *S. aureus* isolates reached 50% (Am. J. Infect. Control 27: 520–532), there is also an emerging prevalence of MRSA strains in the community (Chambers, et al., Emerging Infectious Diseases 7: 178–182). The resistance of MRSA to methicillin and other β-lactam antibiotics is mediated by the acquired penicillin-binding protein 2a (PBP2a). PBP2a is a transpeptidase involved in cell wall peptidoglycan biosynthesis and has very low affinity for these antibiotics. A rational approach to anti-MRSA drug development is to restore sensitivity to R-lactam antibiotics by directly targeting this molecular mechanism of resistance.

Evolutionary Chemistry™ is a methodology for the discovery of small molecule pharmaceutical lead compounds. Evolutionary Chemistry™ is unique in that it integrates the steps of small molecule synthesis and high throughput screening into a single system. This is accomplished by utilizing the ability of RNA to catalyze chemical transformations that can create drug-like molecules, and exploiting this ability to assemble an enormous small molecule library. By incubating a large library of reactant-coupled, random-sequence, modified RNAs (approximately $10^{15}$ unique potential biocatalysts) with a library of small molecule reactants ($10^4$–$10^6$ unique constituents), a library of $10^5$–$10^8$ potential lead compounds can be generated. Potential lead compounds remain attached to the biocatalysts responsible for their formation and are thus addressable. The biocatalyst-assembled product library is then subjected to evolutionary pressures that demand that the selected small molecules have specified properties (such as high affinity for a drug target). Biocatalysts conjugated to lead compounds that exhibit the demanded properties are enzymatically amplified. The biocatalyst sequence-specific small molecule assembly is reliably reproduced in subsequent cycles of biocatalysis, selection, and amplification. These cycles are iterated with increasing evolutionary pressure until the most effective lead compounds evolve from the population.

In the most general embodiments, a nucleic acid-reactant test mixture is formed by attaching a first reactant to each of the nucleic acids in a test mixture (containing $10^2$ to $10^{18}$ nucleic acids with randomized sequences). The nucleic acid-reactant test mixture is treated with other free reactants that will combine with the first reactant to form different products. It is important to note that from the nucleic acid test mixture, discrete nucleic acid sequences will be associated with facilitating the formation of the different shaped products. The products may differ in shape, reactivity or both shape and reactivity. Partitioning of the desirable product shape or reactivity is accomplished by binding to or reaction with a target. Proteins, small molecules, lipids, saccarides, etc., are all examples of targets. After binding to or reacting with the target the non-interacting products, are partitioned from the interacting products, and discarded. The nucleic acid associated with the interacting product is then amplified by a variety of methods known to those experienced in the art. This nucleic acid is then used to facilitate the assembly of the desirable product by facilitating the specific reaction to form the selected product on treatment with the mixture of starting reactants. In a typical reaction, the amplified nucleic acid can be reattached to the first reactant, however, said reattachment is not always required. This is an idealized case and in many examples the nucleic acid facilitator may assemble more than one product from the starting mixture, but all of the products selected will have the desired properties of binding to or chemical reaction with the target.

The overall process is described in more detail in, for example, U.S. Pat. Nos. 6,048,698; 6,030,776; 5,858,660; 5,789,160; 4 5,723,592; and 5,723,289, each of which is entitled "Parallel SELEX," and each of which is incorporated herein by reference in its entirety. These patents are hereinafter referred to collectively as the "Parallel SELEX patents."

The present invention provides novel monobactams with anti-PBP2a activity that were identified using the aforementioned Evolutionary Chemistry™ process.

SUMMARY OF THE INVENTION

In one embodiment, the invention provides monobactams with anti-PBP2a activity having the following formula:

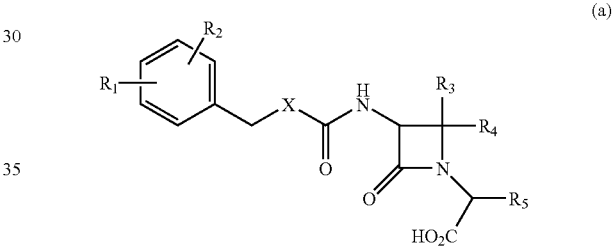

(a)

wherein X is $CH_2$, NH, or O;

$R_1$, $R_2$, $R_3$, $R_4$ and $R_5$ are independently selected from the group consisting of H, $C_1$–$C_{20}$ alkyl, $C_1$–$C_{20}$ alkenyl, $C_1$–$C_{20}$ alkynyl, $OR^6$, $C(O)R^6$, carboalkoxyalkyl, heterocyclyl, aromatic hydrocarbon and cycloalkyl, all of which may be optionally substituted by one or more of the groups selected from $C_1$–$C_{20}$ alkyl, $C_1$–$C_{20}$ alkenyl, $C_1$–$C_{20}$ alkynyl, cycloalkyl, heterocyclyl, aryl, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, $OR^6$, $CONR^6$, wherein all said substituents may be optionally substituted with one or more selected from the group consisting of halogen, $C_1$–$C_{20}$ alkyl, $C_1$–$C_{20}$ alkenyl, $C_1$–$C_{20}$ alkynyl, cycloalkyl, $OR^6$, $C(O)R^6$, carboalkoxyalkyl, cyano, and nitro; and $R_6$ is selected from the group consisting of hydrogen, halogen, $C_1$–$C_{20}$ alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, and carboxamides.

The invention also provides methods for identifying monobactams with anti-PBP2a activity. The methods employ RNA biocatalyst libraries in which each RNA library member has a randomized sequence region and a unique sequence region that encodes the identity of a tethered diene reactant. The RNA molecules are incubated with free reactants formed by the cyclotrimerization of a monobactam alkyne with additional alkynes, at least some of which additional alkynes bear a dienophile functionality. RNA molecules that catalyze the Diels-Alder reaction between a diene and a cyclotrimerization product with a dienophile functionality yield a product that binds to PBP2a (which product is tethered to the 5' end of the RNA via the diene) and are partitioned from the library by virtue of the affinity of the tethered product for PBP2a. The RNA molecules are then amplified, and used to initiate further cycles of selection, leading to the identification of 1) a monobactam that binds to PBP2a; and 2) an RNA molecule (hereinafter referred to as an "RNA biocatalyst") that catalyzes the formation of that monobactam from a diene and a cyclotrimerization product (which acts as a dienophile). The monobactam is then characterized by deconvolution of the reaction history of the RNA, thereby yielding the identity of the individual components incorporated into the monobactam i.e., the alkynes used in the cyclotrimerization and the diene used in the biocatalyzed Diels-Alder reaction.

The invention also provides RNA biocatalysts that can catalyze the formation of compositions with anti-PBP2a activity when tethered to specific diene reactants and then incubated with the cyclotrimerization products of specific alkynes. The compositions thereby produced are also included in the invention, as are the individual compounds within the composition that are responsible for the anti-PBP2a activity.

The invention also provides RNA biocatalysts that can catalyze the formation of compositions with anti-PBP2a activity in the absence of tethered diene reactants when incubated with the cyclotrimerization products of specific alkynes. The compositions thereby produced are also included in the invention, as are the individual compounds within the composition that are responsible for the anti-PBP2a activity.

In another embodiment, the invention provides a monobactam compound having the following formula:

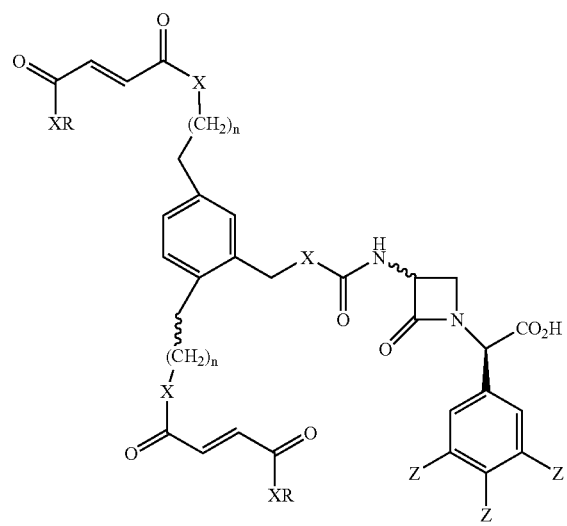

wherein each n is independently 0–4; each X is independently O, S, CHZ or NH; each R is independently lower alkyl optionally substituted with OR, where $R_1$ is H or lower alkyl; and each Z is independently H; halogen; OH; phenyl, heteroaromatic, or lower alkyl optionally substituted with one or more halogen, OH, phenyl or heteroaromatic groups. The invention also includes methods for synthesizing this compound.

BRIEF DESCRIPTION OF THE DRAWINGS

FIG. 2 provides sequence alignments for the random regions of individual clones from the 3H biocatalyst subpopulation.

FIG. 4 provides sequence alignments for the random regions of individual clones from the 8I biocatalyst subpopulation.

DETAILED DESCRIPTION OF THE PREFERRED EMBODIMENTS

Figure 1:
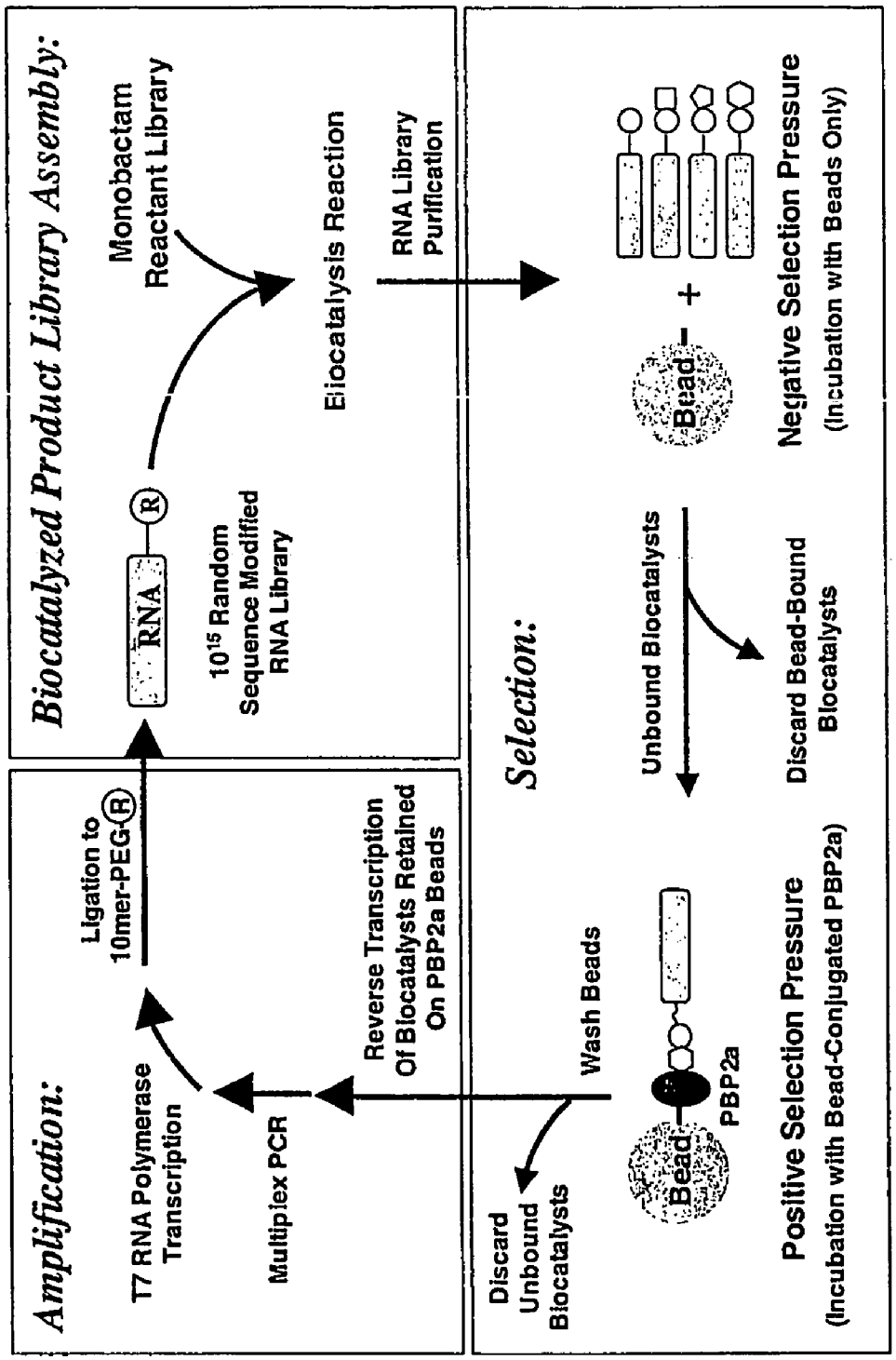
FIG. 1 illustrates schematically the selection process used to identify the biocatalysts of the invention.

The monobactams of the invention may be defined by the formula:

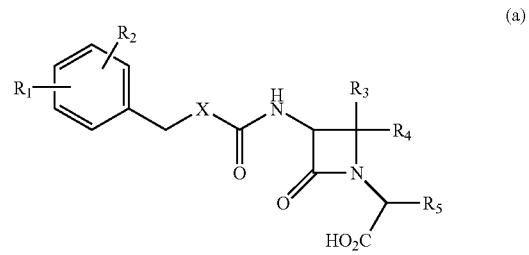

(a)

wherein X is $CH_2$, NH, or O;

$R_1$, $R_2$, $R_3$, $R_4$ and $R_5$ are independently selected from the group consisting of H, $C_1$–$C_{20}$ alkyl, $C_1$–$C_{20}$ alkenyl, $C_1$–$C_{20}$ alkynyl, $OR^6$, $C(O)R^6$, carboalkoxyalkyl, heterocyclyl, aromatic hydrocarbon and cycloalkyl, all of which may be optionally substituted by one or more of the groups selected from $C_1$–$C_{20}$ alkyl, $C_1$–$C_{20}$ alkenyl, $C_1$–$C_{20}$ alkynyl, cycloalkyl, heterocyclyl, aryl, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, $OR^6$, $CONR^6$, wherein all said substituents may be optionally substituted with one or more selected from the group consisting of halogen, $C_1$–$C_{20}$ alkyl, $C_1$–$C_{20}$ alkenyl, $C_1$–$C_{20}$ alkynyl, cycloalkyl, $OR^6$, $C(O)R^6$, carboalkoxyalkyl, cyano, and nitro; and $R_6$ is selected from the group consisting of hydrogen, halogen, $C_1$–$C_{20}$ alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, and carboxamides.

The monobactams of the invention may also be defined as the reaction products formed by:

1) providing a monobactam core alkyne (also referred to herein as an "A alkyne") having the structure

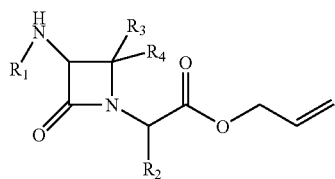

(b)

wherein $R_1$ is one of:

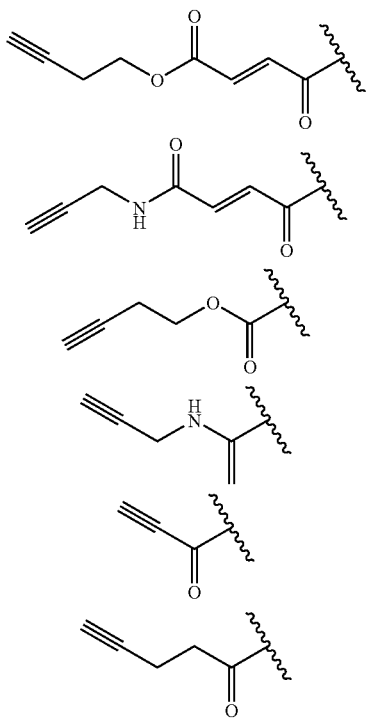

$R_2$ is one of:

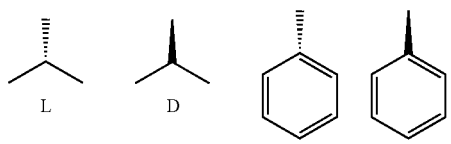

$R_3$ and $R_4$ are independently selected from the group consisting of hydrogen, $C_1$–$C_{20}$ alkyl, $C_1$–$C_{20}$ alkenyl, $C_1$–$C_{20}$ alkynyl, $OR^5$, $C(O)R^5$, carboalkoxyalkyl, heterocyclyl, aromatic hydrocarbon and cycloalkyl, all of which may be optionally substituted by one or more of the groups selected from $C_1$–$C_{20}$ alkyl, $C_1$–$C_{20}$ alkenyl, $C_1$–$C_{20}$ alkynyl, cycloalkyl, heterocyclyl, aryl, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^5$, $OR^5$, $CONR^5$, wherein all said substituents may be optionally substituted with one or more selected from the group consisting of halogen, $C_1$–$C_{20}$ alkyl, $C_1$–$C_{20}$ alkenyl, $C_1$–$C_{20}$ alkynyl, cycloalkyl, $OR^5$, $C(O)R^5$, carboalkoxyalkyl, cyano, and nitro; and $R_5$ is selected from the group consisting of hydrogen, halogen, $C_1$–$C_{20}$ alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, and carboxamides:

2) reacting the monobactam alkyne of 1) with one or more of the following alkynes (hereinafter referred to as "C alkynes") under conditions that promote alkyne cyclotrimerization:

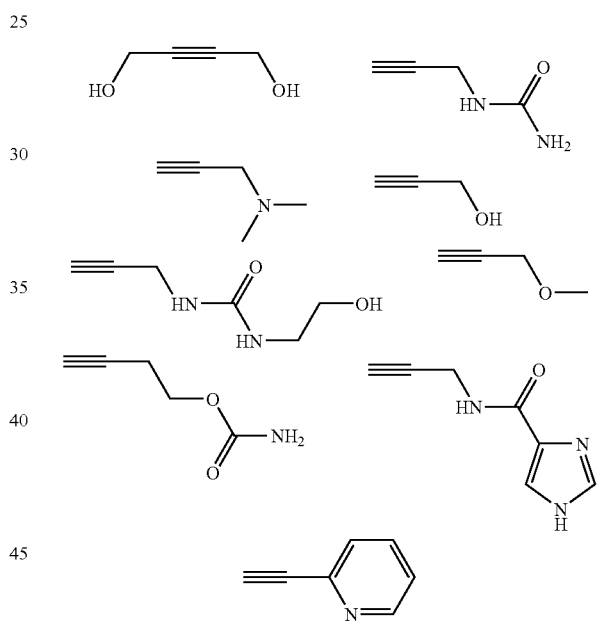

with the priviso that when $R_1$ is one of:

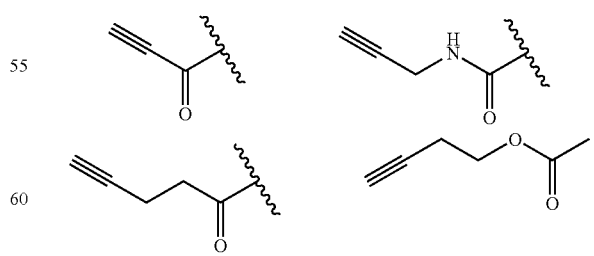

the cyclotrimerization reaction mixture also includes one or more of the following alkynes (hereinafter referred to as "B alkynes"):

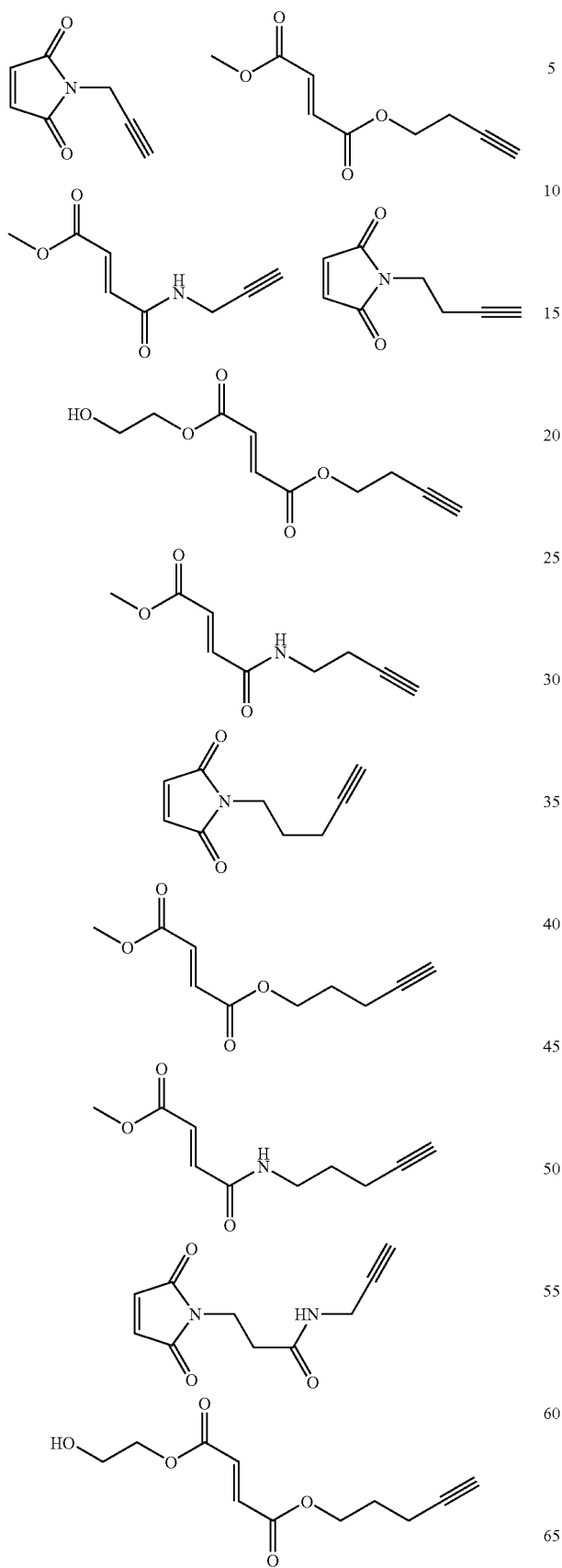
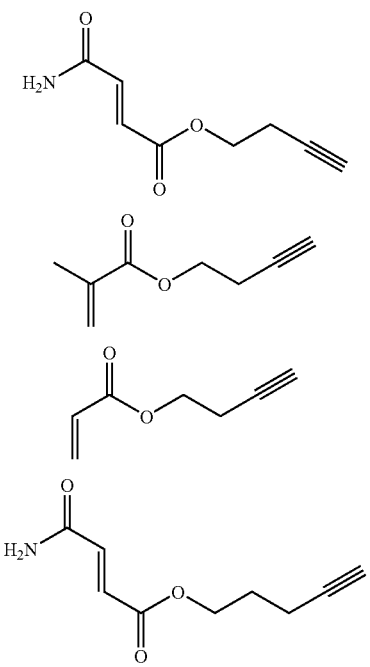
3) performing a Diels-Alder reaction between the cyclotrimerization product of 2) (a dienophile) and one of the following diene reactants (dienes reactants 1–20):
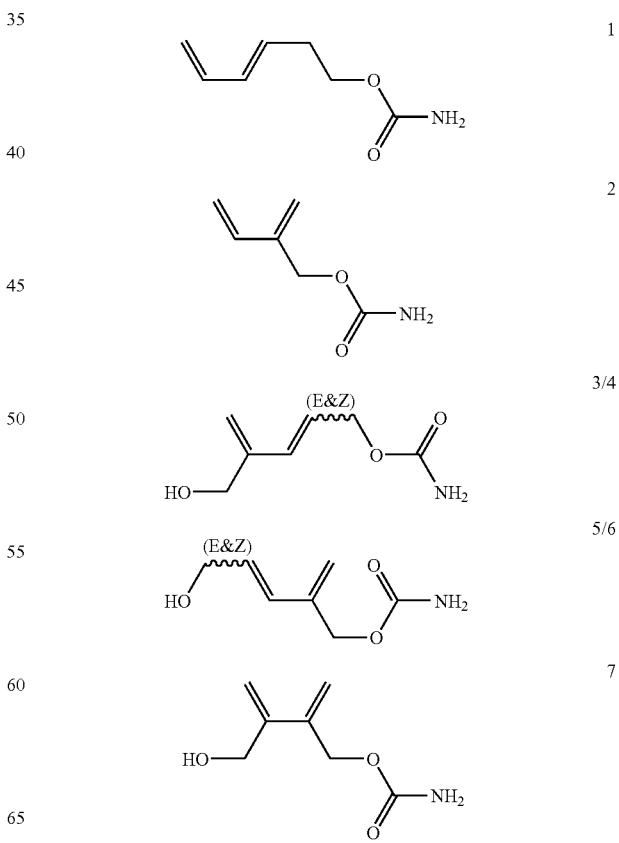

-continued

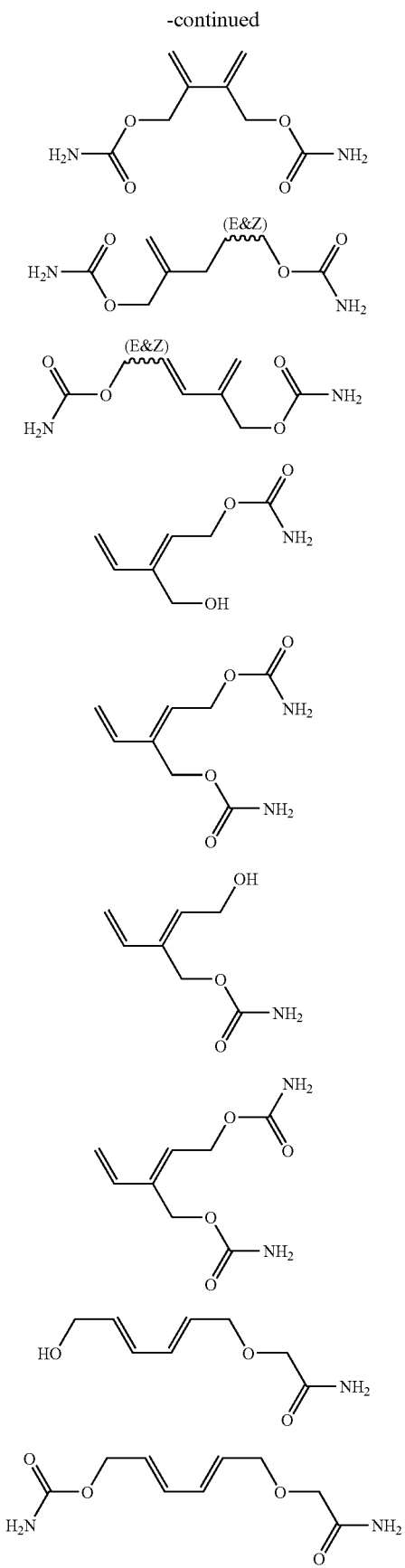

-continued

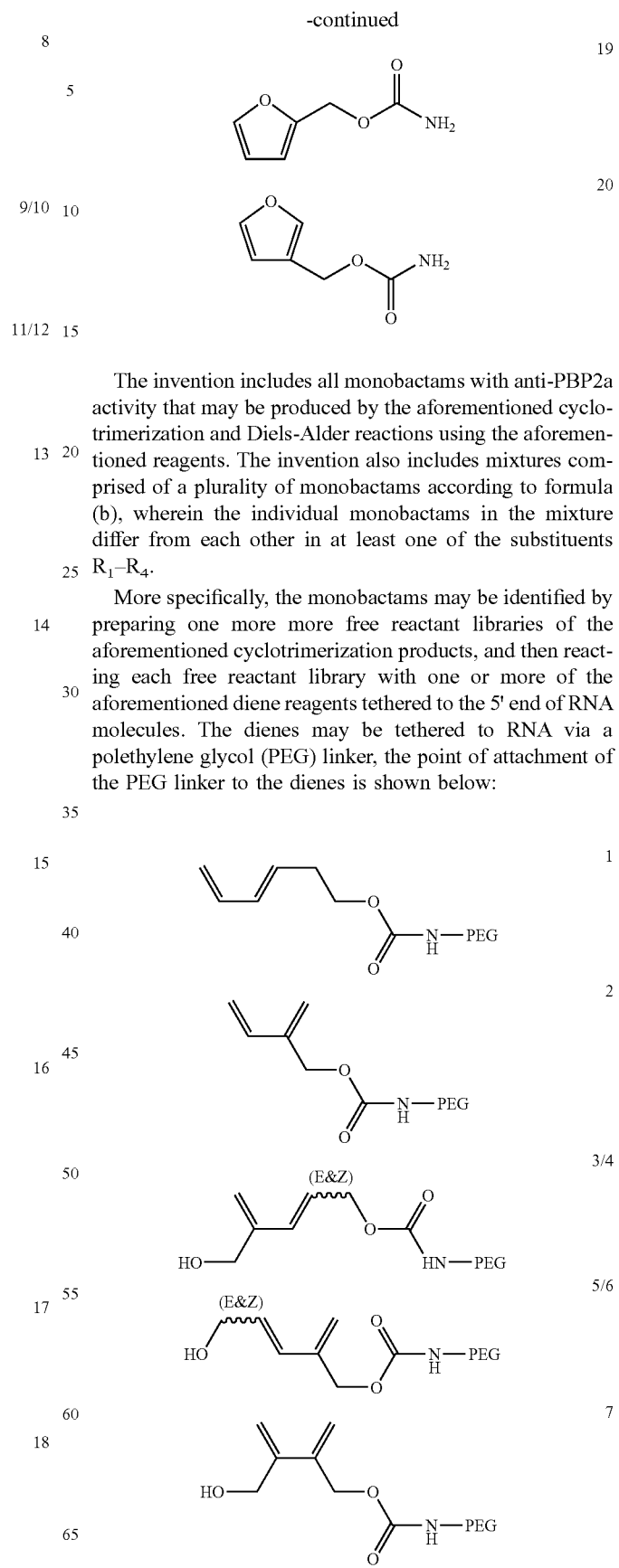

The invention includes all monobactams with anti-PBP2a activity that may be produced by the aforementioned cyclotrimerization and Diels-Alder reactions using the aforementioned reagents. The invention also includes mixtures comprised of a plurality of monobactams according to formula (b), wherein the individual monobactams in the mixture differ from each other in at least one of the substituents $R_1$–$R_4$.

More specifically, the monobactams may be identified by preparing one more more free reactant libraries of the aforementioned cyclotrimerization products, and then reacting each free reactant library with one or more of the aforementioned diene reagents tethered to the 5' end of RNA molecules. The dienes may be tethered to RNA via a polethylene glycol (PEG) linker, the point of attachment of the PEG linker to the dienes is shown below:

The RNA molecules form a RNA biocatalyst library in which each RNA library member has a randomized sequence region and a unique sequence region that encodes the identity of the tethered diene. RNA molecules that catalyze the Diels-Alder reaction between a diene and a cyclotrimerization product to yield a product that binds to PBP2a (which product is tethered to the 5' end of the RNA via the diene) are partitioned from the library by virtue of the affinity of the tethered product for PBP2a. The RNA molecules are then amplified, and used to initiate further cycles of selection, leading to the identification of 1) a monobactam that binds to PBP2a; and 2) an RNA molecule (hereinafter referred to as an "RNA biocatalyst") that catalyzes the formation of that monobactam from a diene and a cyclotrimerization product (which acts as a dienophile). The monobactam is then characterized by deconvolution of the reaction history of the RNA, thereby yielding the identity of the individual components incorporated into the monobactam i.e., the alkynes used in the cyclotrimerization and the diene used in the biocatalyzed Diels-Alder reaction. Methods for the selection of RNA molecules that can generally catalyze the reaction of a tethered reactant with a free reactant, and specifically can catalyze the reaction between a tethered diene reactant and a free dienophile reactant, are provided in the Parallel SELEX patents. Examples 1–12 below provide detailed and non-limiting descriptions of the methods used to generate free reactant libraries, select RNA catalysts, and assay for PBP2a inhibition. FIG. 1 illustrates the selection process schematically.

More specifically, monobactams of the instant invention may be represented by the formula:

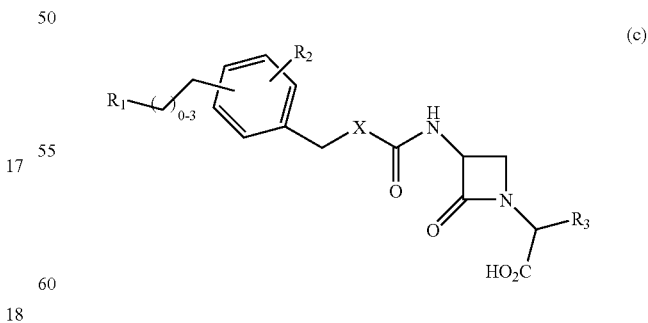

wherein X is CH$_2$, NH, or O;

R$_1$ is the Diels-Alder product formed by the reaction of one of diene reactants 1–20 (which may be tethered to a RNA biocatalyst) with the functionality on the following B alkynes:

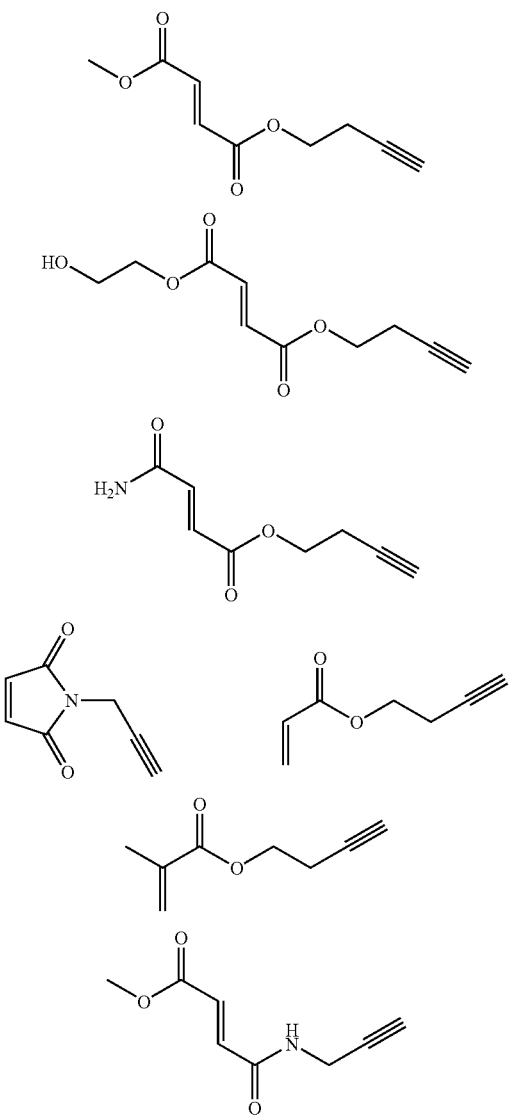

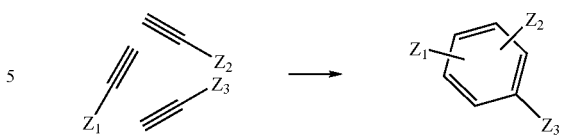

Additional monobactams of the instant invention may be represented by the formula:

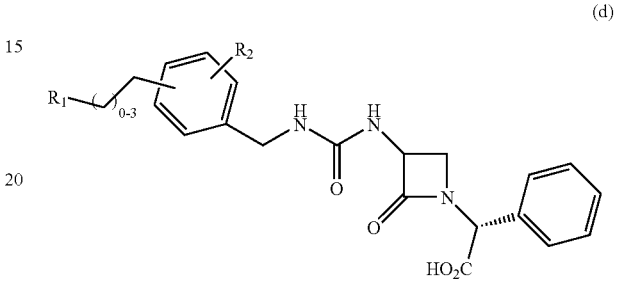

(d)

wherein $R_1$ is the Diels-Alder product formed by the reaction of one of the following diene reagents (shown as free amines; attachment to a RNA biocatalyst is also contemplated, as discussed above):

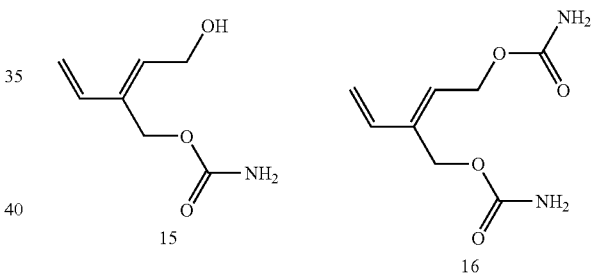

with the functionality on one of the B alkynes, and wherein $R_2$ can be the functionality found on an A, B, or C alkyne.

The invention also includes mixtures comprised of a plurality of monobactams according to formula (d), wherein the individual monobactams in the mixture differ from each other in at least one of the substituents $R_1$–$R_2$.

Still further monobactams of the instant invention can be represented by the formula:

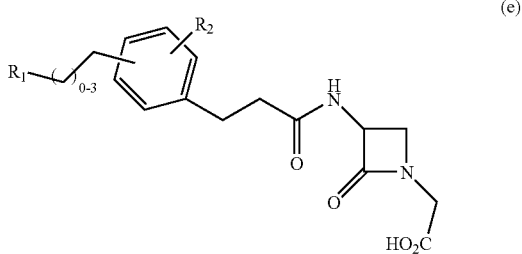

(e)

$R_2$ is the functionality found on the A alkynes, B alkynes or C alkynes; and $R_3$ is one of:

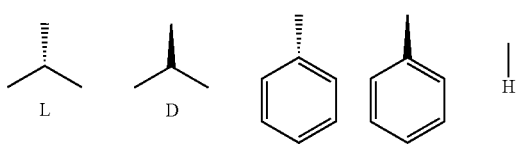

The invention also includes mixtures comprised of a plurality of monobactams according to formula (c), wherein the individual monobactams in the mixture differ from each other in at least one of the substituents $R_1$–$R_6$.

Note that the term "functionality" used in the context of A, B, or C alkynes refers to the moiety attached to the alkyne group, which moiety becomes one of the substituents of the ring formed during cyclotrimerization. For example, in the following hypothetical the functionalities are $Z_1$, $Z_2$, and $Z_3$:

wherein R₁ is the Diels-Alder product formed by the reaction of the following diene reagent (shown as a free amine; attachment to a RNA biocatalyst is also contemplated, as discussed above):

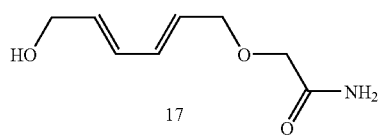

with the functionality on one of the B alkynes, and wherein R₂ can be the functionality found on an A, B, or C alkyne.

The invention also includes mixtures comprised of a plurality of monobactams according to formula (e), wherein the individual monobactams in the mixture differ from each other in at least one of the substituents $R_1$–$R_2$.

Even further monobactams of the instant invention can be represented by the formula:

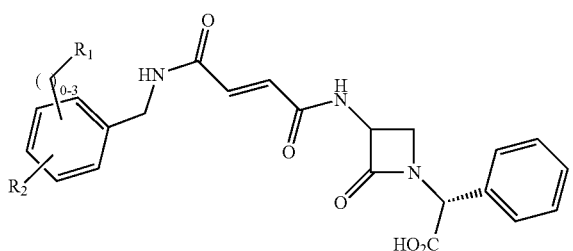

(f)

wherein R₁ is the Diels-Alder product formed by the reaction of the following diene reagent (shown as a free amine; attachment to a RNA biocatalyst is also contemplated, as discussed above):

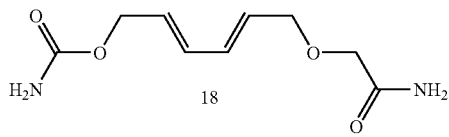

with the functionality on one of the B alkynes, and wherein R₂ an be the functionality found on an A, B, or C alkyne.

The invention also includes mixtures comprised of a plurality of monobactams according to formula (f), wherein the individual monobactams in the mixture differ from each other in at least one of the substituents $R_1$–$R_2$.

Yet further monobactams of the instant invention can be represented by the formula:

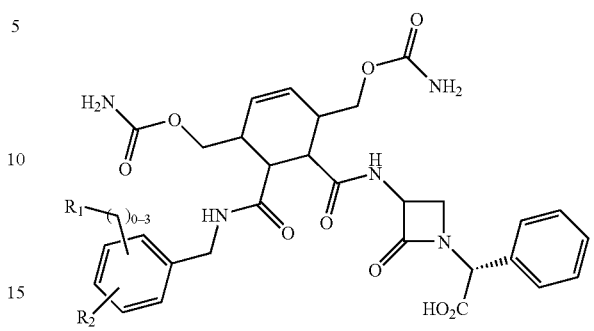

(g)

wherein each of $R_1$ and $R_2$ is independently the functionality on any one of the A alkynes, the B alkynes, and the C alkynes.

The invention also includes mixtures comprised of a plurality of monobactams according to formula (g), wherein the individual monobactams in the mixture differ from each other in at least one of the substituents $R_1$–$R_4$.

The monobactams of the instant invention were initially identified by selecting for catalytic RNA molecules that catalyze the reaction between a diene (tethered to the RNA via a PEG linker) and a dienophile (a free reactant library member). The selection process also identified RNA molecules in which certain nucleophilic functionalities present in the RNA itself react with members of the free reactant library, thereby forming a monobactam that is tethered directly to the RNA, rather than via the diene tethered to a PEG linker. The following functionalities present on RNA can serve as nucleophiles:

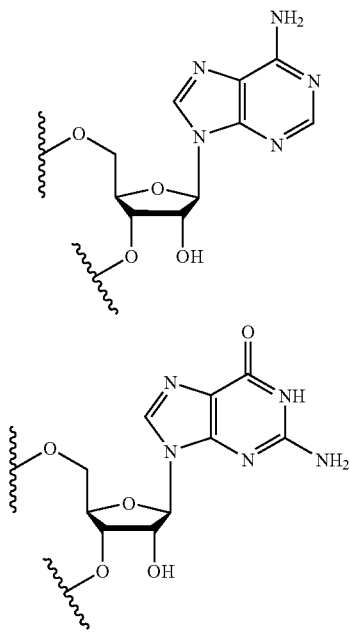

-continued

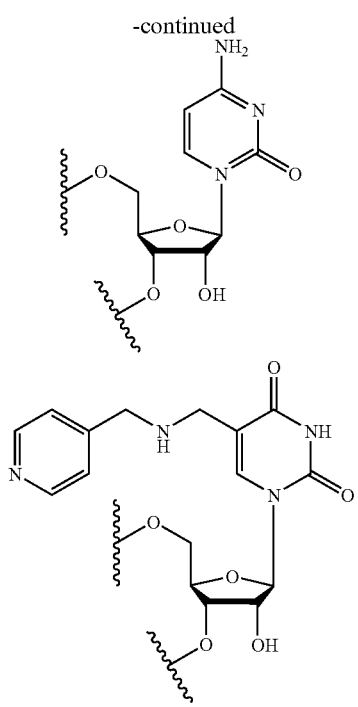

Hence, further monobactams of the instant invention can be represented by the formula (h)

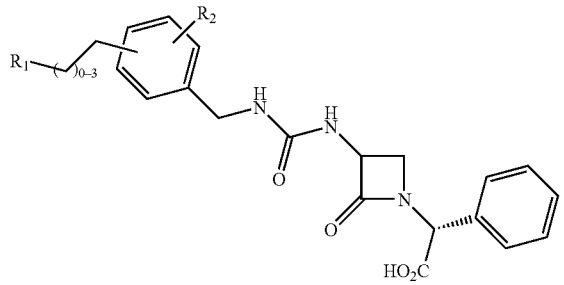

wherein R$_1$ is the product of the reaction between one of the aforementioned nucleophilic functionalties present in RNA with one of the functionalities on one of the B alkynes, and wherein R$_2$ an be any functionality found on an A, B, or C alkyne.

The invention also includes mixtures comprised of a plurality of monobactams according to formula (h), wherein the individual monobactams in the mixture differ from each other in at least one of the substituents R$_1$–R$_2$.

The invention also provides RNA molecules that can catalyze the formation of the above-mentioned compositions, and further includes the compositions thereby produced. Preferred RNA molecules have the sequence:

```
5' GGGAGAAUCAAAGUAAUCGCUCA-[X]-   SEQ ID NO: 121
UUCGACAGGAGGCUCACAACAGGC 3'
``` in which X is one of the sequences provided in FIG. 2 (SEQ ID NOS: 41–84 and 120), and U is 5-(4-pyridylmethyl) uridine). Each of the aforementioned RNA biocatalysts (hereinafter referred to collectively as "3H biocatalysts" may be used to provide a composition with anti-PBP2a activity. Specifically, a free reactant library is synthesized by cyclotrimerizing, with all of the B alkynes and all of the C alkynes, the monobactam alkyne (A alkyne 43) having the formula:

A43

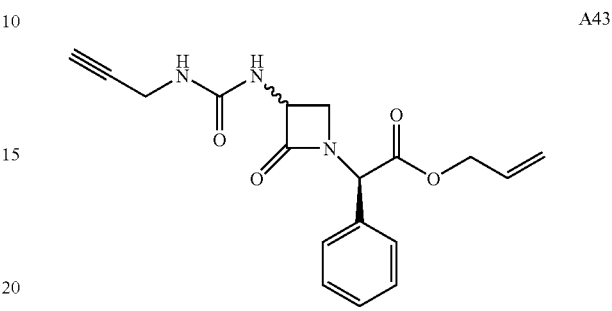

An exemplary method for cyclotrimerization is provided in Example 2. The resulting free reactant sublibrary (termed C43) comprises a large number of cyclotrimerization products, each having the following formula:

(i)

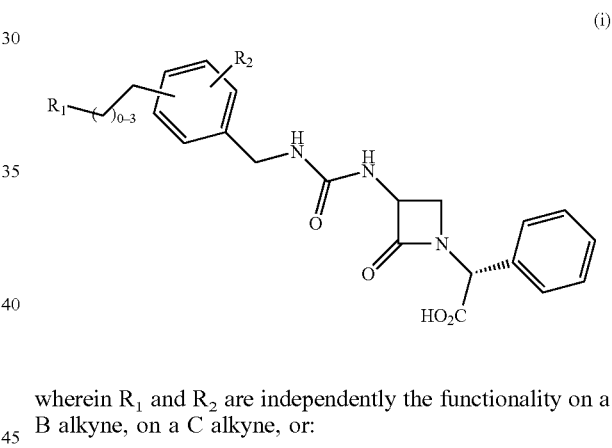

wherein R$_1$ and R$_2$ are independently the functionality on a B alkyne, on a C alkyne, or:

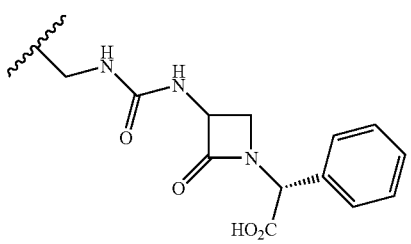

Following cyclotrimerization, the free reactant sublibrary may be partitioned from unreacted reagents. The library is then incubated with one or more of the aforementioned RNA biocatalysts. Biocatalysis yields a composition having anti-PBP2a activity. The individual biocatalyzed products in the composition with anti-PBP2a activity may then be purified by virtue of their affinity for PBP2a. The structure of the product(s) responsible for the anti-PBP2a may be determined by, for example, a combination of reactant library deconvolution, involving the synthesis and analysis of successively smaller subsets of free reactant sublibrary C43, and tandem C18 reversed-phase HPLC-electrospray mass spectrometry (LC-MS) techniques.

Preferably, the RNA biocatalyst used in conjunction with the free reactant library C43 is 3H4 (x=SEQ ID NO: 66), 3H15 (x=SEQ ID NO: 120), 3H16 (x=SEQ ID NO: 77), 3H38 (x=SEQ ID NO: 75), 3H50 (x=SEQ ID NO: 62), 3H56 (x=SEQ ID NO: 72), or 3H112 (x=SEQ ID NO: 43).

Figure 3:
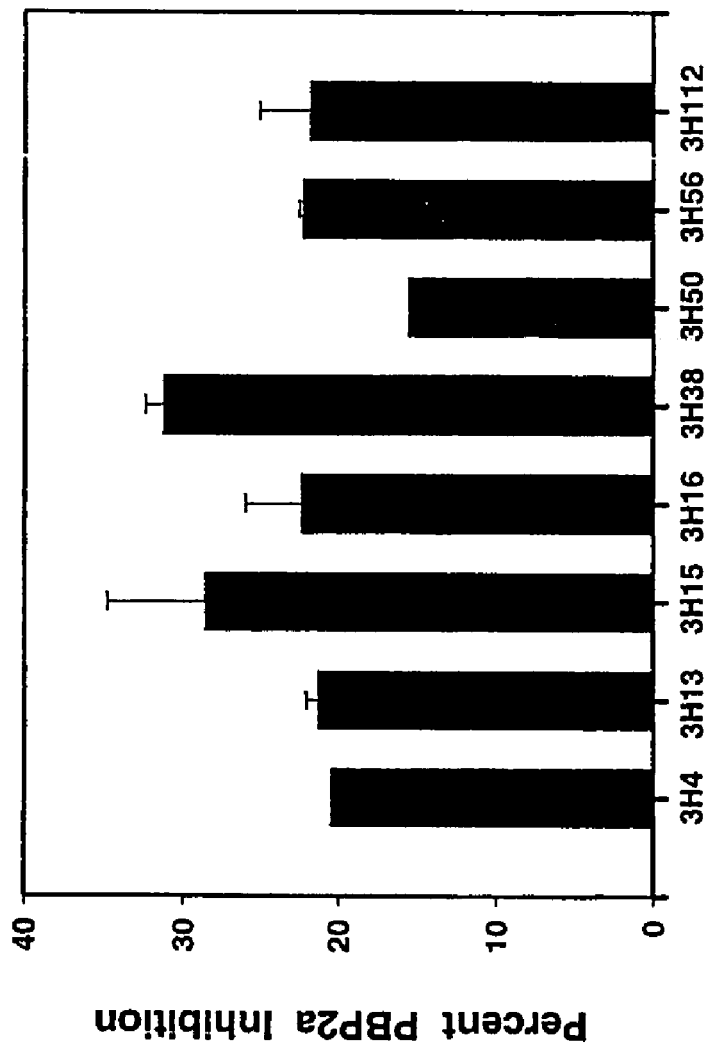
FIG. 3 illustrates the PBP2a inhibitory activity of products produced by individual biocatalysts isolated from subpopulation 3H.

FIG. 3 illustrates percentage PBP2a inhibition values for the compositions produced by these biocatalysts.

The reaction and kinetic parameters of PBP2a inhibition by the compositions produced by these RNA biocatalysts with the free reactant library C43 may be represented as follows:

$$E + I \underset{k_{-1}}{\overset{k_1}{\rightleftharpoons}} E \cdot I \overset{k_2}{\rightarrow} E - I \overset{k_3}{\rightarrow} E \cdot I^*$$

$$K_1 = k_3/(k_2/K_m); k_2 = (d[E-I]/dt)/[E \cdot I]; K_m = [E][I]/[E \cdot I]$$
$$k_2/K_m = ((d[E-I]/dt)[E \cdot I])/([E][I]/[E \cdot I]) = (d[E-I]/dt)/([E][I])$$

Values for the individual kinetic parameters are listed in Table 1.

The individual biocatalyzed products in the composition with anti-PBP2a may then be purified by virtue of their affinity for PBP2a. The structure of the product(s) responsible for the anti-PBP2a may be determined by, for example, a combination of reactant library deconvolution, involving the synthesis and analysis of successively smaller subsets of free reactant sublibrary C43, and tandem C18 reversed-phase HPLC-electrospray mass spectrometry (LC-MS) techniques.

Note that the anti-PBP2a activity generated by the individual RNA biocatalyst subpopulation 3H clones with the free reactant sublibrary C43 does not depend on the presence of the tethered diene reactants 15 and 16 (or of the associated PEG linker and 10 nt ssDNA). This indicates that the anti-PBP2a activity produced by these RNA biocatalysts is not the result of a Diels-Alder reaction between a tethered diene and a dienophile moeity on a free reactant sublibrary member. Instead, it is likely that a functional group inherent in RNA itself participates in the biocatalyzed reaction with a free reactant sublibrary member, thereby acting as the

TABLE 1

| Biocatalyst | [E] (µM) | [I] (µM) | [E − I] (µM) | d[E − I] (µM/min) | $k_2/K_m$ (µM$^{-1}$min$^{-1}$) | $K_1$ (µM) | IC$_{50}$ (µg/ml) | Random Region SEQ ID NO: |
|---|---|---|---|---|---|---|---|---|
| Entire 3H subpop. (incl. tethered diene reactant 15) | 1.1 | 2.8 | 0.32 | 0.0036 | 0.0012 | 0.93 | 0.64 | — |
| Clone 3H4 | 1.2 | 1.5 | 0.25 | 0.0028 | 0.0016 | 0.70 | 0.48 | 66 |
| Clone 3H15 | 1.2 | 1.5 | 0.34 | 0.0035 | 0.0021 | 0.53 | 0.37 | 120 |
| Clone 3H16 | 1.5 | 2.0 | 0.34 | 0.0037 | 0.0012 | 0.93 | 0.64 | 77 |
| Clone 3H38 | 1.2 | 1.5 | 0.38 | 0.0042 | 0.0023 | 0.48 | 0.33 | 75 |
| Clone 3H50 | 1.2 | 1.5 | 0.19 | 0.0021 | 0.0011 | 0.97 | 0.67 | 62 |
| Clone 3H56 | 1.2 | 1.5 | 0.27 | 0.0030 | 0.0017 | 0.68 | 0.47 | 72 |
| Clone 3H112 | 1.5 | 1.5 | 0.33 | 0.0036 | 0.0016 | 0.69 | 0.48 | 43 |

The inhibition data indicates that the anti-PBP2a activity of the isolated monobactam derivatives produced by the aforementioned 3H4, 3H15, 3H16, 3H38, 3H50, 3H56, and 3H112 RNA biocatalysts in conjunction with the free reactant sublibrary C43 is comparable to that observed with bicyclic β-lactam inhibitors of this enzyme (literature IC$_{50}$ values range from ~0.4–4 µg/ml; examples given in Table 2; see Example 12).

TABLE 2

Examples of reported β-lactam inhibitors of PBP2a.

| Source | Compound Class | IC$_{50}$ for PBP2a | Reference |
|---|---|---|---|
| Eli Lilly (LY-206763) | Carbacephem | 2 µg/ml | J. Med. Chem. 36: 1971–76 |
| Taiho Pharmaceutical (TOC-39) | 2-Thioisocephem | 0.58 µg/ml | Chemotherapy 43: 1–5 |
| RW Johnson/ Microside (MC-02479) | Cephem | 0.5 µg/ml | ICAAC (1998) 38: F14, 21, 22, 24, &25 |

"tethered" reagent that attaches the RNA biocatalyst to the free reactant sublibrary member. As described above, the following groups in RNA can serve as tethered reagents:

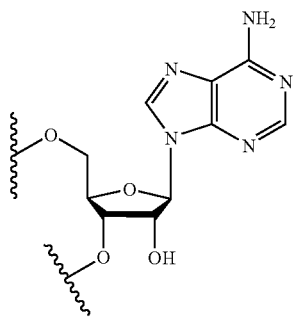

-continued

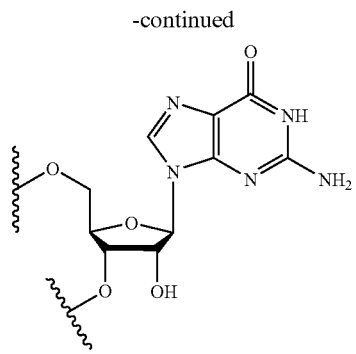

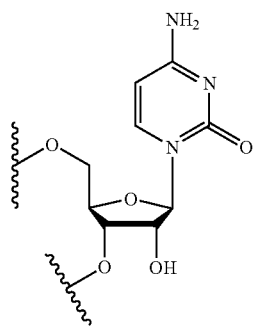

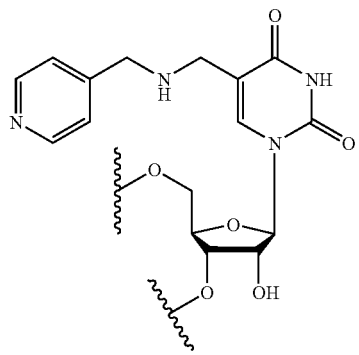

More specifically, but without being limited to a single mechanism or hypothesis, it is contemplated that the primary amine group on an RNA base reacts as a nucleophile with a functionality on a B or C alkyne. For example, the RNA biocatalyst may catalyze the following reaction between a functionality on a B alkyne (which functionality is present as a substituent of the phenyl ring of a free reactant sublibrary member) and an RNA base:

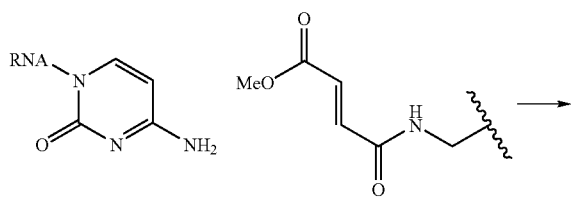

-continued

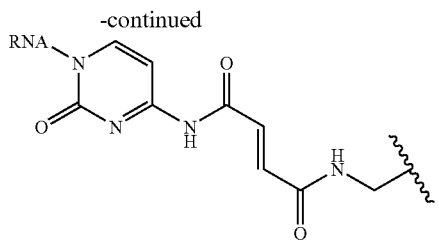

Figure 7:
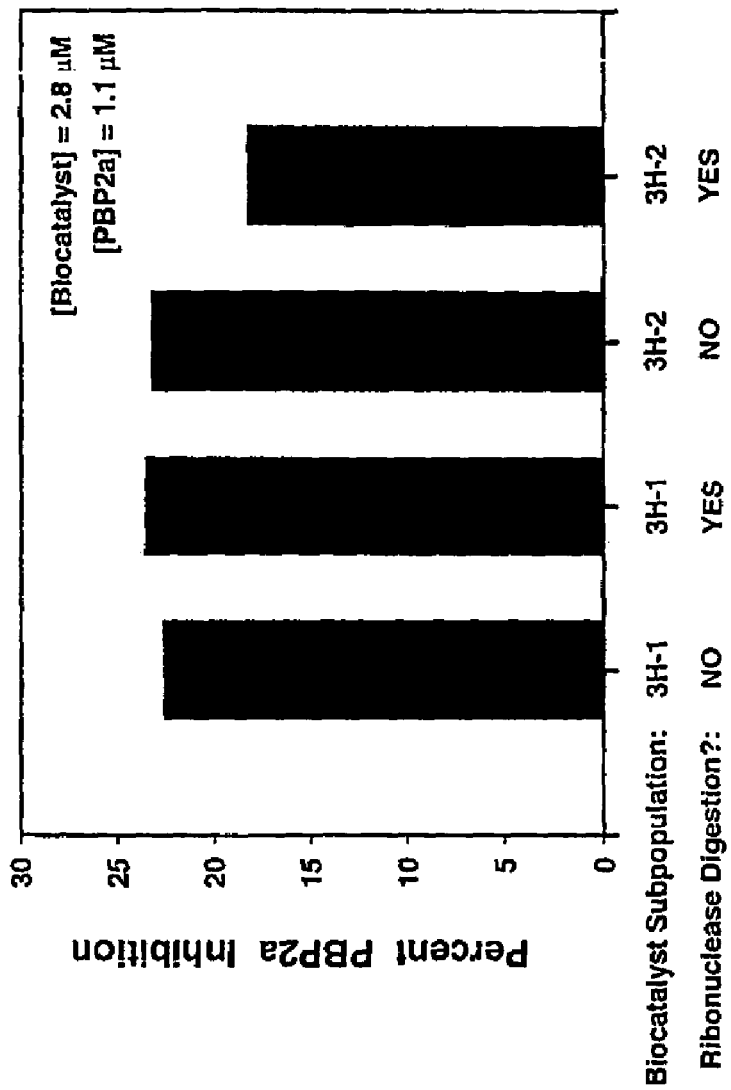
FIG. 7 illustrates that the inhibition of PBP2a activity observed for products produced by the 3H biocatalyst subpopulation is not sensitive to RNase digestion.

Example 10 and FIG. 7 demonstrate that the anti-PBP2a activity of the biocatalyzed product is resistant to RNase digestion. Therefore, it is likely that only one or a very few RNA bases are required in the product for activity.

In another embodiment, the invention provides further RNA molecules that can catalyze the formation of the above-mentioned compositions, and further includes the compositions thereby produced. Preferred RNA molecules have the sequence:

5'dienel7/PEG/<u>CCCTCTCATA</u>GGGAGACCUAAG SEQ ID NO: 122

CAUCUAAACUA(Y)UUCGACAGGAGGCUCACAACAG

GC3' in which Y is one of the sequences provided in FIG. 4 (SEQ ID NOS: 86–119), U is 5-(4-pyridylmethyl) uridine, the underlined sequence is DNA, and the 5' end of the DNA is coupled to a 2,000 MW PEG linker, which in turn is coupled to the free amine of diene reactant 17 having the structure:

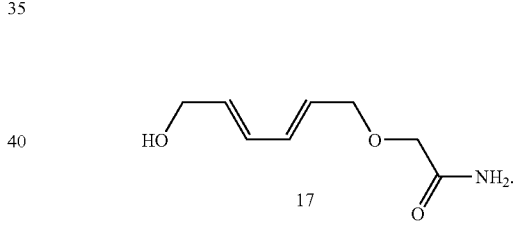

Each of the aforementioned RNA biocatalysts (hereinafter referred to collectively as "8I biocatalysts") may be used to provide a composition with anti-PBP2a activity. Specifically, a free reactant library is synthesized by cyclotrimerizing, with all of the B alkynes and all of the C alkynes, the monobactam alkyne (A alkyne 24) having the formula:

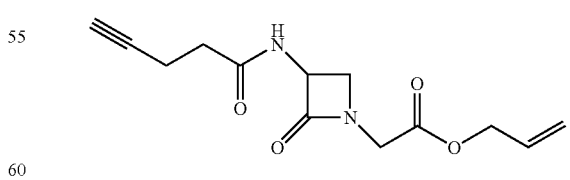

Cyclotrimerization produces a free reactant sublibrary, termed C24, comprising a large number of monobactams. Following cyclotrimerization, the free reactant sublibrary may be partitioned from unreacted reagents. The free reactant sublibrary C24 is then incubated with one or more of the aforementioned 8I RNA biocatalysts (including tethered diene reactant 17). Biocatalysis yields a composition having anti-PBP2a activity. The individual biocatalyzed products in the composition with anti-PBP2a activity may then be purified by virtue of their affinity for PBP2a. The structure of the product(s) responsible for the anti-PBP2a may be determined by, for example, a combination of reactant library deconvolution, involving the synthesis and analysis of successively smaller subsets of free reactant sublibrary C43, and tandem C18 reversed-phase HPLC-electrospray mass spectrometry (LC-VMS) techniques.

Although the monobactams with anti-PBP2a activity described throughout this application were initially identified using RNA biocatalysts, one skilled in the art will appreciate that it is possible to synthesize all of the aforementioned monobactams using standard organic synthesis techniques. Hence, the invention is not limited to monobactams with anti-PBP2a activity that are formed by the RNA biocatalysts described herein.

In another embodiment, the invention provides a monobactam compound with the following formula:

(j)

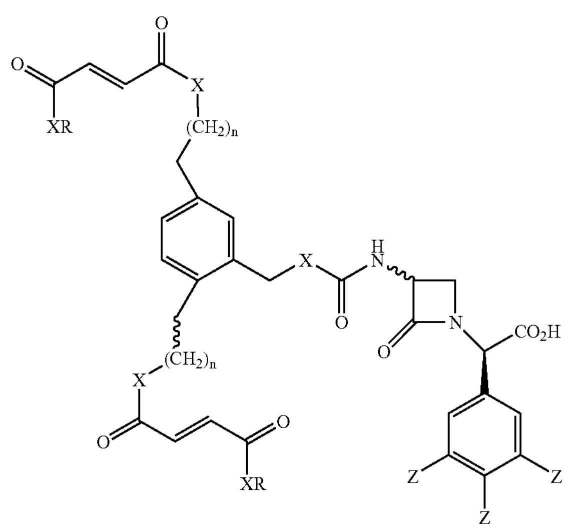

wherein each n is independently 0–4; each X is independently O, S, $CH_2$ or NH; each R is independently lower alkyl optionally substituted with OR, where $R_1$ is H or lower alkyl; and each Z is independently H; halogen, OH; phenyl, heteroaromatic, or lower alkyl optionally substituted with one or more halogen, OH, phenyl or heteroaromatic groups. This compound may be synthesized according to the method of Example 13.

The present methods resulted in the preparation of the monobactam compounds described above. Those compounds have antibacterial activity and thus may be administered to patients (including humans and mammals) in need thereof. For therapeutic or prophylactic treatment, the compounds of the present invention may be formulated in a pharmaceutical composition, which may include, in addition to an effective amount of active ingredient, pharmaceutically acceptable carriers, thickeners, diluents, buffers, preservatives, surface active agents and the like. Pharmaceutical compositions may also include one or more other active ingredients if necessary or desirable.

The pharmaceutical compositions of the present invention may be administered in a number of ways as will be apparent to one of ordinary skill. Administration may be done topically, orally, rectally, nasally, vaginally, by inhalation, or parenterally (including subcutaneous, intramuscular, intravenous and intradermal), for example.

Topical formulations may include ointments, lotions, creams, gels, drops, suppositories, sprays, liquids and powders. Oral formulations include powders, granules, suspensions or solutions in water or non-aqueous media, capsules or tablets, for example. Thickeners, flavorings, diluents, emulsifiers, dispersing aids or binders may be used as needed.

Parenteral formulations may include sterile aqueous solutions which may also contain buffers, diluents and other suitable additives.

The dose regimen will depend on a number of factors which may readily be determined, such as severity and responsiveness of the condition to be treated, but will normally be one or more doses per day, with a course of treatment lasting from several days to several months, or until a cure is effected or a diminution of disease state is achieved. One of ordinary skill may readily determine optimum dosages, dosing methodologies and repetition rates. In general, it is contemplated that unit dosage form compositions according to the present invention will contain from about 0.01 mg to about 500 mg of active ingredient, preferably about 0.1 mg to about 10 mg of active ingredient. Topical formulations (such as creams, lotions, solutions, etc.) may have a concentration of active ingredient of from about 0.1% to about 50%, preferably from about 0.1% to about 10%. However, final strength of the finished dosage form will depend on the factors listed above and may be readily determined by one of ordinary skill.

While the present invention has been described in terms monobactam derivatives having activity against MRSA, it will be readily appreciated that the methods described herein could be used to generate compounds having different core structures, as well as compounds active against other pharmaceutical targets.

EXAMPLE 1

Reactant Library Design and Synthesis

The PBP2a Evolutionary Chemistry™ small molecule reactant library was designed around the monobactam pharmacophore. An approximate 5,000,000-member monobactam library was assembled and surveyed for PBP2a inhibitors using the Evolutionary Chemistry process. The monobactam library was created by the RNA catalyzed combination of free and tethered reactants. The tethered reactants attached to the RNA via a PEG linker were the following 20 dienes (diene reactants 1–20):

1

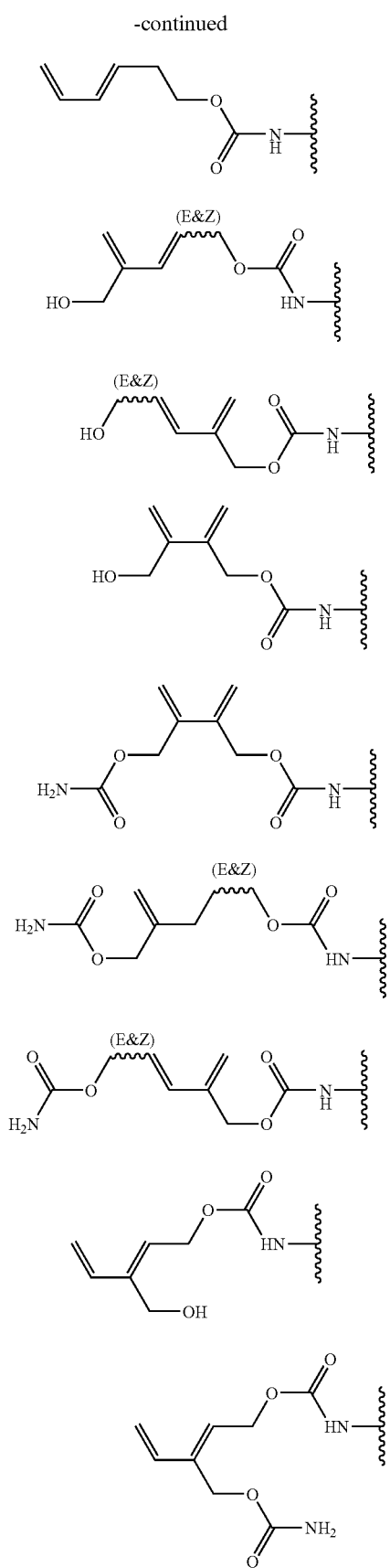
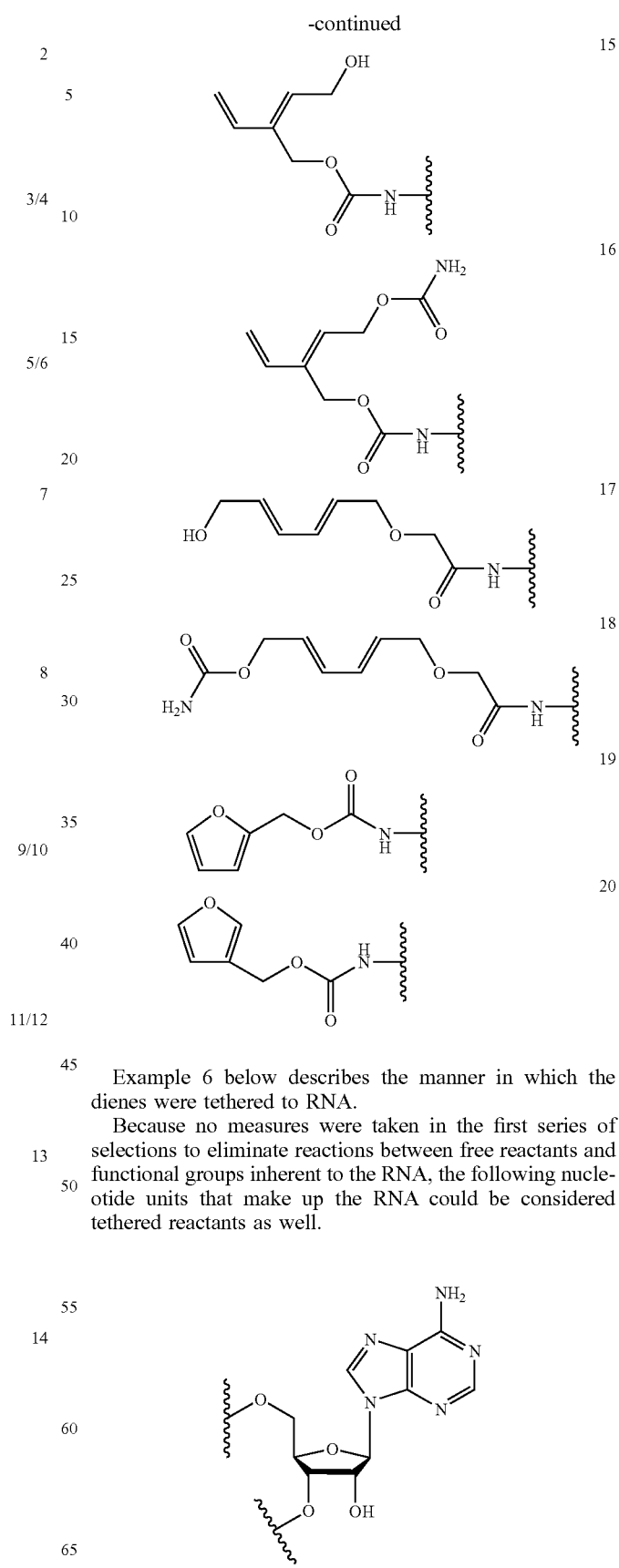
Example 6 below describes the manner in which the dienes were tethered to RNA.
Because no measures were taken in the first series of selections to eliminate reactions between free reactants and functional groups inherent to the RNA, the following nucleotide units that make up the RNA could be considered tethered reactants as well.

-continued

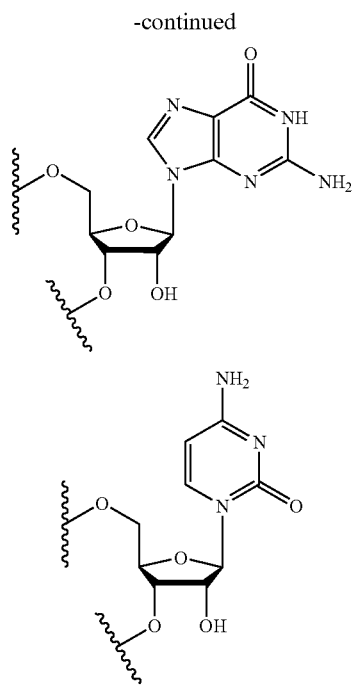

-continued

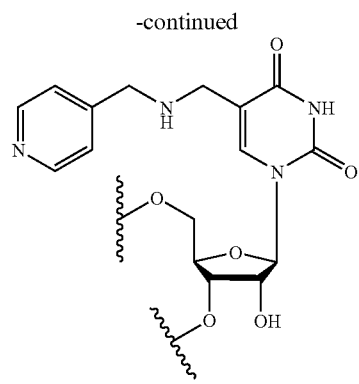

The free reactants were assembled via the cyclotrimerization of three different classes of alkynes consisting of monobactam alkynes (alkyne A's), dienophiles/reactant alkynes (alkyne B's) and alkynes bearing other functionality (alkyne C's). The alkynes used to create the monobactam free reactant library are shown below.

A Alkynes: 30 monobactam (A) alkynes were synthesized and used to create the free reactant library. The 30 monobactam alkynes were comprised of all of the combinations of $R_1$ and $R_2$ as shown in Table 3:

TABLE 3

| | A alkynes (monobactam alkynes) | | | | |
|---|---|---|---|---|---|
| $R_1$ | | | $R_2$ | | |
| | L | D | | | H |
| | A10 | A11 | A12 | A13 | A14 |
| | A20 | A21 | A22 | A23 | A24 |
| | A30 | A31 | A32 | A33 | A34 |
| | A40 | A41 | A42 | A43 | A44 |

TABLE 3-continued
A alkynes (monobactam alkynes)
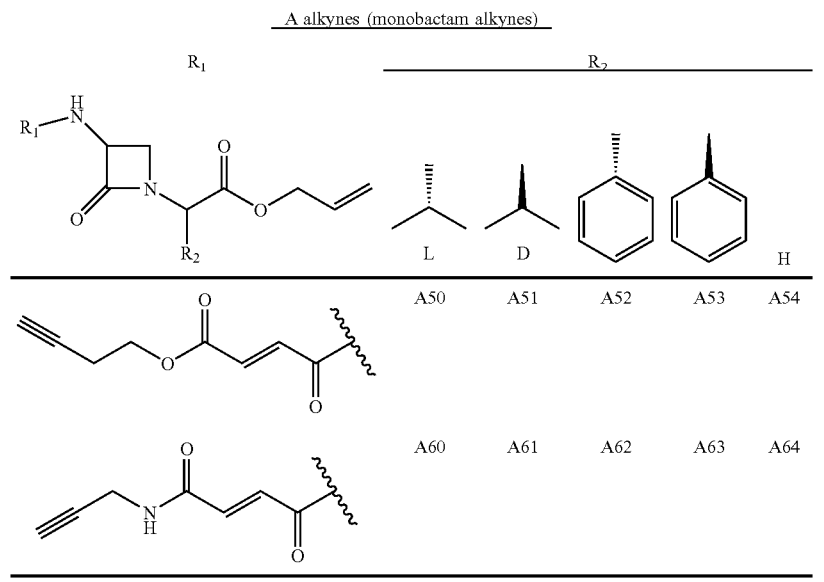
| | L | D | | H |
|---|---|---|---|---|
| | A50 | A51 | A52 | A53 | A54 |
| | A60 | A61 | A62 | A63 | A64 |
B Alkynes: The following 15 alkynes were used in the synthesis of the free reactants, each of which has reactive functionality that RNA can catalytically modify using the tethered reactants.
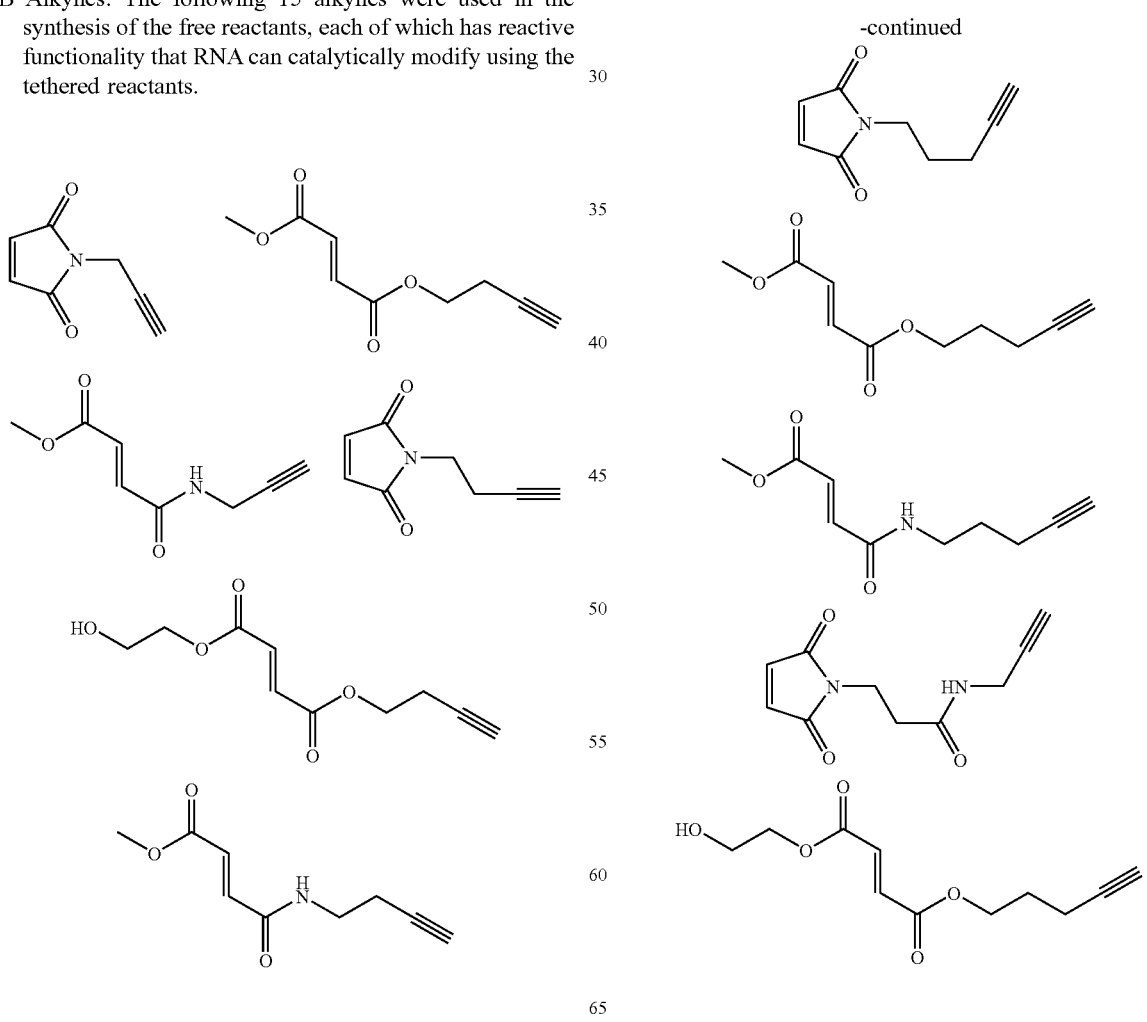

-continued

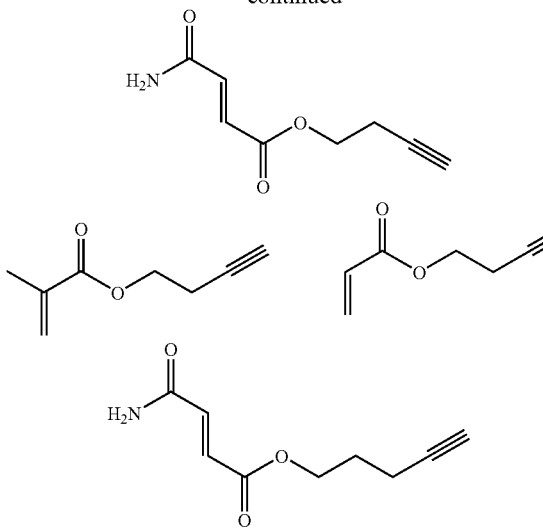

C Alkynes: The following 9 alkynes were used to synthesize the free reactant library.

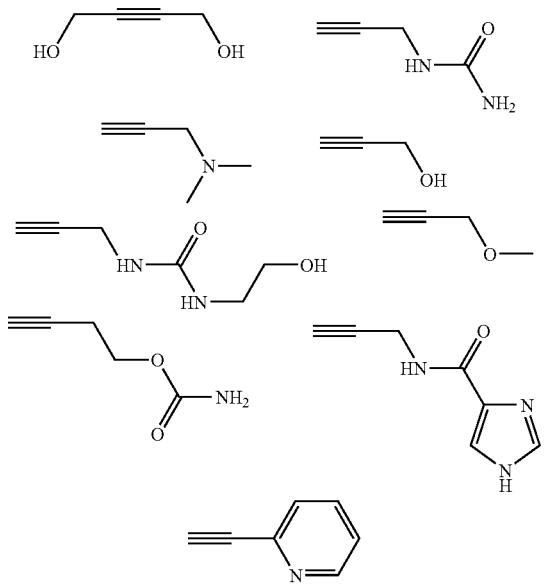

The free reactant library was comprised of 30 free reactant sub-libraries with each sub-library created by the cyclotrimerization of one A alkyne with all of the C alkynes and either with or without all of the B alkynes. Specifically, A alkynes A10–A44 were cyclotrimerized with all of the B alkynes and all of the C alkynes, while A alkynes A50–A64 were cyclotrimerized only with the C alkynes. Each free reactant sublibrary (also referred to asia "core library") is referred to using the A alkyne used to create that sublibrary e.g., "C43" refers to the sublibrary created by the cyclotrimerization of A alkyne A43 with all of the B and C alkynes. The following example illustrates the cyclotrimerization of A alkyne A43 with all the B and C alkynes to create free reactant sublibrary C43; the same procedure was used for the other core A alkynes.

EXAMPLE 2

Synthesis of Free Reactant Sublibrary C43 by Cyclotrimerization of Alkynes

Alkyne A43 has the following structure:

A43

$C_{18}H_{19}N_3O_4$
Exact Mass: 341.14
Mol. Wt.: 341.36

Cyclotrimerization was performed using the following cobalt catalyst, hereinafter referred to as "Cp$Co[COD]":

This alkyne cyclotrimerization catalyst is described in great detail in U.S. Pat. Nos. 5,659,069; 5,760,266; and 6,225,500, each entitled "Method for the Cyclotrimerization of Alkynes in Aqueous Solutions," and each incorporated herein by reference in their entirety.

All of the following weighing and reaction set-ups were conducted in an inert atmosphere glove box.

Alkyne A43 (monobactam alkyne): In the box, weigh out 228 mg (0.667 mmol) of core into reaction tube.

B Alkynes (all 15): Weight out each solid, combine in a clean dry vial and take into the box. Combine liquids in a flask, freeze-pump-thaw to remove oxygen (3×), and take into the box. Dissolve the liquids in dry deoxygenated THF to a final volume of 2.0 mL, transfer the solution to the vial containing the solid alkynes and store the mixture in the glovebox freezer. Label contents of bottle as Alkyne B Core 43 Main Library Master Mix with the date prepared. Final stock concentrations should be 33 mM in each alkyne and 500 mM total alkyne. Use 2.0 mL in cyclotrimerization mixture for library synthesis (0.667 mmol core A43).

C Alkynes (all 9): Weight out each solid and combine in a clean and dry vial and take into the box. If necessary, Vac-transfer fresh batches of the liquids and take into the box. Dissolve the solids in dry deoxygenated THF to a final volume of 2.0 mL, add remaining liquid alkynes and store in the glovebox freezer. Label contents of bottle as Alkyne C Core 43 Main Library Master Mix with the date prepared. Final stock concentrations should be 37 mM in each alkyne and 333 mM total alkyne. Use 2.0 mL in cyclotrimerization mixture for main library synthesis (0.667 mmol core A43).

Cp$Co[COD]: Weigh out 74.4 mg (0.234 mmol) catalyst in glovebox. Add 2.0 mL of dry deoxygenated THF to give a final stock concentration of 117 mM. Use 2.0 mL in cyclotrimerization mixture for main library synthesis (0.667 mmol core A43).

Cyclotrimerization Reaction

To Alkyne A in the reaction tube, add 2.0 mL of alkyne B stock solution, 2.0 mL of alkyne C stock solution, 2.0 mL of catalyst stock solution and 7.3 mL of dry deoxygenated THF to give a final volume of 13.3 mL. Final concentrations should be the following:
Alkyne A: 50 mM
Alkyne B (each alkyne): 5.0 mM
Alkyne C (each alkyne): 5.6 mM
Cp$Co[COD]: 17.5 mM Add stir bar, seal reaction tube, take out of box and heat at 105° C. for 72 hr.

The cyclotrimerization reaction products were then subjected to an activated charcoal treatment according to the following method:

Activated Charcoal Treatment
Equipment:
  100 mL round bottoms
  THF
  MeOH
  Clean rotovap bump trap
  Transfer pipet
  10 mL syringe
  Acrodisc (0.45 µM, PTFE)

Procedure: Transfer cyclotrimerization reaction to 100 mL round bottom flasks. Rotovap with a bath temperature of 20° C. The mixture may bump. After concentrating add up to 100 mL MeOH in 25 mL to the flask to dissolve the reaction mixture. If products do not completely dissolve then roto-vap to dryness and proceed to the next step, deprotection. If products dissolve completely then add 90 mg of activated charcoal and a stir bar, cap with a plastic cap-plug and stir for 5 minutes at room temperature. Using the transfer pipet, transfer the mixture to the 10 mL syringe fitted with the acrodisc filter. Filter the mixture into a 100 mL round bottom flask. Rinse the flask with 3 mL and then 1.5 mL of MeOH, filtering each through the acrodisc and collecting the filtrate into the 100 mL round bottom flask. Concentrate the mixture on the rotovap using minimal heat (<25° C.) to avoid bumping. The crude reaction mixture should be a brown oil.

The crude reaction mixture was then deprotected according to the following procedure:

Deprotection
Equipment:
  Box
  2×14/20 septa
  18 gauge disposable needle
  $PdL_4$
  0.2 M TEAA in DMF
  1 mL pipetman
  stir bar
  DMF Procedure: Place a septum equipped with the 18 g needle on the flasks containing the crude reaction mixture and take the flask into the box. To each of the three flasks add 46 mg of $PdL_4$ (6 mol %) followed by 33 mL of 0.2 M TEAA/DMF (10 eq.) solution. Add a stir bar to each flask and seal with a septum. Remove all from the box and stir for 4 hours at room temperature. Remove the stir bar and rinse with DMF. Concentrate the mixture on the rotovap using minimal heat (<25° C. bath temp.). Further evaporate the DMF on a high vacuum line for at least 15 minutes while stirring or rotating the flask to increase surface area.

The deprotected products were then subjected to anion exchange purification according to the following procedure.

Anion Exchange Purification
Equipment:
  Bio-rad low-pressure chromatography system
  Sephadex A-25 resin
  15% MeOH/$H_2O$
  15% MeOH/500 mM TBK (pH 7) or 15% MeOH/500 mM NaCl
  1000 mL round bottom flask Procedure: Dilute mixture to <5 mM using 15% MeOH/$H_2O$. Load onto 200 mL of Sephadex A-25 anion exchange resin ($HCO_3^-$ of $Cl^-$ equilibrated) at 1 mL/min. Wash column with 15% MeOH/$H_2O$ at 15 mL/min for 50 min. Elute library with 15% MeOH/500 mM TBK or 15% MeOH/500 mM NaCl solution at 15 mL/min., collect sample based on UV absorbance (usually peak elutes after 10–15 min of TBK or NaCl and requires ~30 additional minutes to fully elute). Freeze purified library and lyophilize.

The residue from the anion exchange purification was then subjected to reverse phase purification according to the following procedure.

Reverse Phase Purification
Equipment:
  Prep-C18 reverse phase HPLC column
  Prep-HPLC Procedure: Dissolve residue from anion exchange purification in a minimum amount of $H_2O$. Add MeCN up to 10% to obtain complete solution of residue. Load onto the prep C18 column at 1% MeCN/$H_2O$, wash for 10 minutes with 1% MeCN/$H_2O$ and then flash elute library by rapidly increasing mobile phase to 95% MeCN/$H_2O$ over 2 minutes. Collect and combine all products that are eluted with the increased MeCN, remove MeCN by rotary evaporation and remove remaining $H_2O$ by lyophilization.

EXAMPLE 3

Creation of Free Reactant Libraries by Combination of Individual Free Reactant Sub-Libraries Each of the 30 free reactant sub-libraries was dissolved in 50% MeOH/$H_2O$ to a final concentration of 100 mM. They were combined as follows to create the 10 free reactant libraries (FR1–10):

Library Stocks: All volumes correspond to 100 mM stock solutions of each of the sub-libraries in 50% MeOH/$H_2O$. Final concentration of total monobactam in each library is 80 mm.

FR 1: C10, C12, C53 (369 µL C10; 369 µL C12; 62.0 µL C53; 200 µL $H_2O$)

FR 2: C11, C44, C52 (369 µL C11; 369 µL C44; 62.0 µL C52; 200 µL $H_2O$)

FR 3: C21, C43, C64 (369 µL C21; 369 µL C43; 62.0 µL C64; 200 µL $H_2O$)

FR 4: C13, C20, C54 (369 µL C13; 369 µL C20; 62.0 µL C54; 200 µL H$_2$O)
FR 5: C14, C23, C50 (369 µL C14; 369 µL C23; 62.0 µL C50; 200 µL H$_2$O)
FR 6: C34, C42, C51 (369 µL C34; 369 µL C42; 62.0 µL C51; 200 µL H$_2$O)
FR 7: C22, C31, C63 (369 µL C22; 369 µL C31; 62.0 µL C63; 200 µL H$_2$O)
FR 8: C24, C30, C62 (369 µL C24; 369 µL C30; 62.0 µL C62; 200 µL H$_2$O
FR 9: C32, C41, C60 (369 µL C32; 369 µL C41; 62.0 µL C60; 200 µL H$_2$O)
FR 10: C33, C40, C61 (369 µL C33; 369 µL C40; 62.0 µL C61; 200 µL H$_2$O)
FR 11:
   36.9 µL C10, C11, C12, C13, C14 C20, C21, C22, C23, C24 C30, C31, C32, C33, C34 C40, C41, C42, C43, C44
   +6.2 µL C50, C51, C52, C53, C54 C60, C61, C62, C63, C64
   +200 µL H$_2$O

EXAMPLE 4

Cloning, Expression, and Purification of PBP2a

Following previously published cloning and expression methods (Frank et al., Protein Expr. Purif. 6: 671–8), the mecA gene from MRSA strain 27 was modified to remove the putative N-terminal trans-membrane region and cloned into the T7 RNA polymerase expression vector pET-11d, which was then used to transform *Escherichia coli* strain BL21 (DE3). The protein was isolated in the form of inclusion bodies, requiring extraction, denaturation, and renaturation by methods described in the above reference. The protein was then purified by cation-exchange on CM Sepharose (Sigma) and affinity chromatography on Reactive Blue 4 agarose (Sigma). Typical yields of purified protein were 5 mg/L culture.

EXAMPLE 5

Conjugation of Purified PBP2a to Sepharose Beads

For use in partitioning reactions, PBP2a was conjugated to sulfhydryl-functionalized Sepharose 4B via the heterobifunctional cross-linking reagent sulfosuccinimidyl 6(3-[2-pyridyldithio]propionamido)hexanoate (Sulfo-LC-SPDP; Pierce), providing a disulfide linkage between the solid support and PBP2a. Step one of the conjugation procedure was incubation of 10 mg/ml PBP2a with 5 mM Sulfo-LC-SPDP in 150 mM NaCl, 0.05% Triton X-100, and 50 mM sodium phosphate, pH 7.5. Following a one hour incubation at room temperature with constant gentle mixing, unreacted Sulfo-LC-SPDP was removed by extensive washing (with 150 mM NaCl, 10 mM EDTA, 0.05% Triton X-100, 50 mM sodium phosphate, pH 7.5). Step two of the procedure was the preparation of sulfhydryl-functionalized Sepharose beads. Pyridyldithio-functionalized Sepharose 4B (Sigma) was added at 125 mg/ml to 50 mM HEPES, pH 7.5, allowed to completely hydrate, then transferred to a mini-chromatography column (Bio-Rad) and washed extensively with the same buffer. One ml of 200 mM dithithreitol in 50 mM HEPES, pH 7.5 was added per 500-µl bead bed volume and the column was capped. Following a 30-min incubation at room temperature with constant mixing on a rotating platform the beads were extensively washed (~25 ml) with 150 mM NaCl, 10 mM EDTA, 0.05% Triton X-100, 50 mM sodium phosphate, pH 7.5. The washed beads were transferred to a microcentrifuge tube and excess buffer was removed. In step 3 of the procedure, 450-µl of pyridyldithiol-functionalized PBP2a from step 1 was combined with a 500-µl bed volume of thiol-functionalized Sepharose 4B prepared in step2. The reaction was incubated at 4° C. for 16 hours then transferred to a mini-chromatography column and washed extensively (~20 ml) with 150 mM NaCl, 10 mM EDTA, 0.05% Triton X-100, and 50 mM sodium phosphate, pH 7.5 to remove non-conjugated PBP2a. Sepharose-S-S-PBP2a bead conjugates were stored at 4° C.

The quantity of active PBP2a per microliter bead bed volume was determined by active site titration with [$^{14}$C] benzylpenicillin. A 10-µl bead bed volume was first washed with three 200-µl volumes of assay buffer (1.2 M NaCl, 20% glycerol, 20 mM HEPES, pH 7.0). [$^{14}$C]benzylpenicillin at 200 µg/ml in assay buffer was added to the beads and the reaction was incubated at room temperature with constant mixing on a rotating platform for 3 hours. Following incubation, the beads were washed with five 400-µl volumes of 1.2 M NaCl, 50 mM HEPES, pH 7.0. The beads were then suspended in 100 µl of the same buffer and transferred to scintillation fluid for liquid scintillation. The quantity of active PBP2a per microliter bead volume was determined by extrapolation from a standard curve prepared from scintillation counts of [$^{14}$C]benzylpenicillin at known concentrations and specific activity.

EXAMPLE 6

Design and Synthesis of Biocatalyst RNA Library

Figure 5:
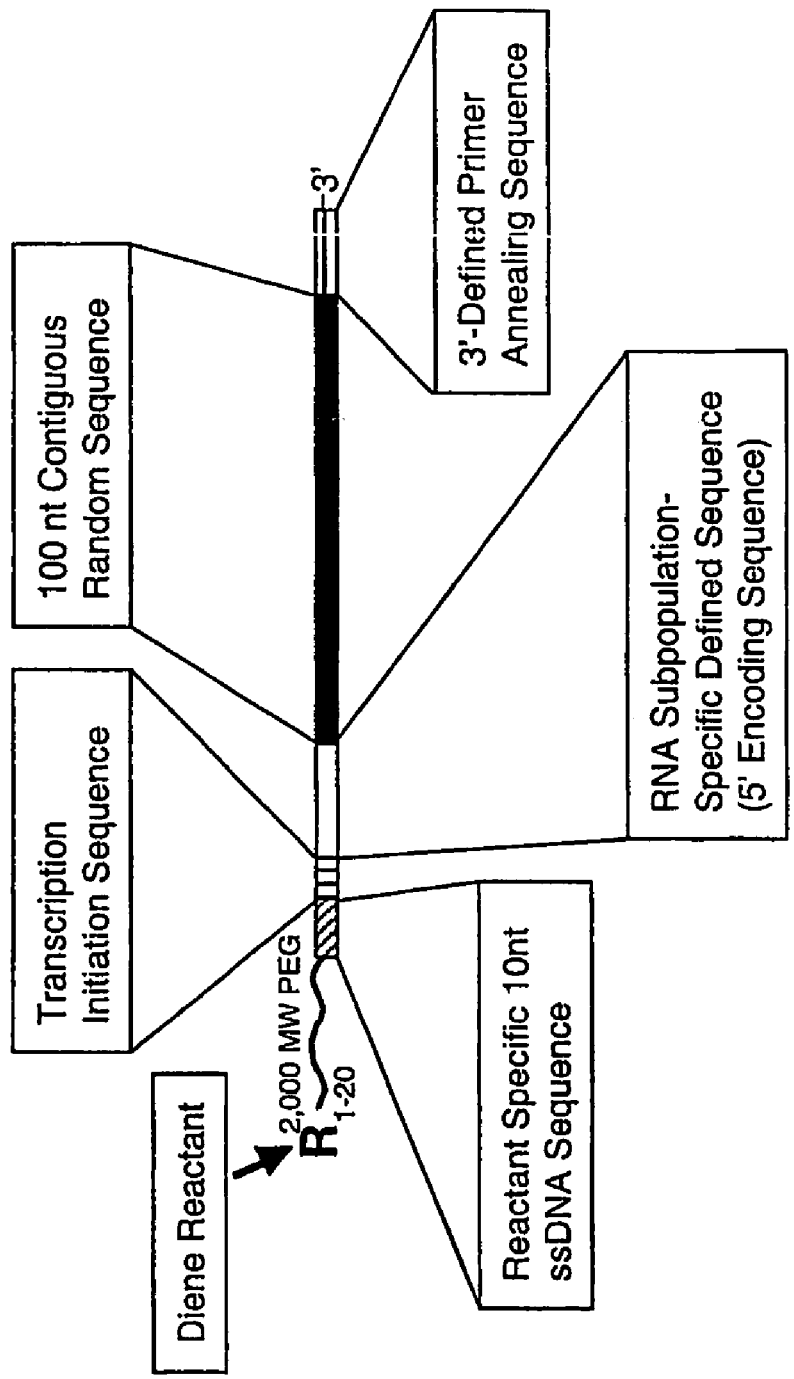
FIG. 5 illustrates the general structure of the RNAs used in the biocatalyst screening method.

The modified RNA library utilized for each Evolutionary Chemistry experiment was composed of ten different RNA subpopulations (A–J), each differing in a 5'-encoding sequence that permitted the 5' ligation of only one out of ten different sequence-encoded 10 nt ssDNA-PEG$_{2000}$-Diene reactant species (see FIG. 5). Each RNA in the population had in common a 6-nucleotide high efficiency T7 transcription initiation sequence, a 100-nt contiguous random sequence block (100N), and a 3'-defined primer-annealing sequence.

The dsDNA template for the initial random sequence modified RNA library was generated through high-efficiency PCR amplification of chemically-synthesized ssDNA with the following sequences:

A:    GGGAGACAAGAATAAACGCTCAA-(100N)- SEQ ID NO: 1
      TTCGACAGGAGGCTCACAACAGGC

B:    GGGAGATGCTACTACTAACAACA-(100N)- SEQ ID NO: 2
      TTCGACAGGAGGCTCACAACAGGC

C:    GGGAGGAAACATCACAATCCATA-(100N)- SEQ ID NO: 3
      TTCGACAGGAGGCTCACAACAGGC

D:    GGGAGATAATAAATGCCCAGAGA-(100N)- SEQ ID NO: 4
      TTCGACAGGAGGCTCACAACAGGC

E:    GGGAGAAATACAAATAGGCAGGA-(100N)- SEQ ID NO: 5
      TTCGACAGGAGGCTCACAACAGGC

F:    GGGAGAACTTATTATTCACCCGA-(100N)- SEQ ID NO: 6
      TTCGACAGGAGGCTCACAACAGGC

G:    GGGAGACTATTTATCATACGGCA-(100N)- SEQ ID NO: 7
      TTCGACAGGAGGCTCACAACAGGC

```
                         -continued
H:   GGGAGAATCAAAGTAATCGCTCA-(100N)- SEQ ID NO: 8
     TTCGACAGGAGGCTCACAACAGGC

I:   GGGAGACCTAAGCATCTAAACTA-(100N)- SEQ ID NO: 9
     TTCGACAGGAGGCTCACAACAGGC

J:   GGGAGAAGGTAGTAGTAGAAGAT-(100N)- SEQ ID NO: 10
     TTCGACAGGAGGCTCACAACAGGC
```

The 5' primers utilized in this amplification (and throughout the selection experiments) included a T7 RNA polymerase promoter sequence and have the following sequence:

```
5pA:   TAA TAC GAC TCA CTA TAG GGA     SEQ ID NO: 11
       GAC AAG AAT AAA CGC TCA A

5pB:   TAA TAC GAC TCA CTA TAG GGA     SEQ ID NO: 12
       GAT GCT ACT ACT AAC AAC A

5pC:   TAA TAC GAC TCA CTA TAG GGA     SEQ ID NO: 13
       GGA AAC ATC ACA ATC CAT A

5pD:   TAA TAC GAC TCA CTA TAG GGA     SEQ ID NO: 14
       GAT AAT AAA TGC CCA GAG A

5pE:   TAA TAC GAC TCA CTA TAG GGA     SEQ ID NO: 15
       GAA ATA CAA ATA GGC AGG A

5pF:   TAA TAC GAC TCA CTA TAG GGA     SEQ ID NO: 16
       GAA CTT ATT ATT CAC CCG A

5pG:   TAA TAC GAC TCA CTA TAG GGA     SEQ ID NO: 17
       GAC TAT TTA TCA TAC GGC A

5pH:   TAA TAC GAC TCA CTA TAG GGA     SEQ ID NO: 18
       GAA TCA AAG TAA TCG CTC A

5pI:   TAA TAC GAC TCA CTA TAG GGA     SEQ ID NO: 19
       GAC CTA AGC ATC TAA ACT A

5pJ:   TAA TAC GAC TCA CTA TAG GGA     SEQ ID NO: 20
       GAA GGT AGT AGT AGA AGA T
```

Following PCR amplification, the cDNA was transcribed from the T7 polymerase promoter. Transcription was performed using 5-(4-pyridylmethyl)UTP:

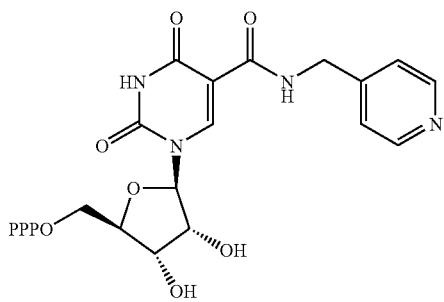

instead of UTP in the transcription reaction (Dewey et al., Nucleosides & Nucleotides 15: 1611–7). Due to the 100-nt contiguous random sequence, each RNA sequence is either unique or, as a result of the above amplification process, present in the population at a very low copy number (<10).

Each 10-nt ssDNA was tethered to one of two possible dienes (approx. equimolar mixture of each) via a 2000-MW polyethylene glycol (PEG) linker, resulting in a total of 20 different diene reactants within the RNA library. The individual diene species are illustrated in Example 1 above. The 10-nt ssDNAs have the following sequences and tethered dienes:

| Tethered Dienes | | | |
|---|---|---|---|
| 10-A: | AAA CCA CCC C | 1, 2 | SEQ ID NO: 21 |
| 10-B: | CCA GGC ACG C | 3, 4 | SEQ ID NO: 22 |
| 10-C: | CTC CTC CTT T | 5, 6 | SEQ ID NO: 23 |
| 10-D: | GAG GAG GGA G | 7, 8 | SEQ ID NO: 24 |
| 10-E: | GTG TTG GGT G | 9, 10 | SEQ ID NO: 25 |
| 10-F: | CAC GCG ACA C | 11, 12 | SEQ ID NO: 26 |
| 10-G: | TTT CGG CGG G | 13, 14 | SEQ ID NO: 27 |
| 10-H: | GGG TGG TAA A | 15, 16 | SEQ ID NO: 28 |
| 10-I: | CCC TCT CAT A | 17, 18 | SEQ ID NO: 29 |
| 10-J: | ATA GCG GCT C | 19, 20 | SEQ ID NO: 30 |

The 10-nt ssDNA species were ligated to the transcribed RNA using bridging oligonucleotides. Each bridging oligonucleotide (listed below) is complementary to the 5' portion of only one of the RNA sub-populations and complementary to one of the 10-nt ssDNA molecules. For example, bridging oligonucleotide Br-B was used to ligate ssDNA 10-A (with its two possible attached diene species linked to the 5' end via a 2,000 MW PEG linker) to RNA subpopulation B.

```
Br-A:   CTT GTC TCC CGG GGT GGT TT     SEQ ID NO: 31

Br-B:   AGC ATC TCC CGC GTG CCT GG     SEQ ID NO: 32

Br-C:   GTT TCC TCC CAA AGG AGG AG     SEQ ID NO: 33

Br-D:   ATT ATC TCC CCT CCC TCC TC     SEQ ID NO: 34

Br-E:   TAT TTC TCC CCA CCC AAC AC     SEQ ID NO: 35

Br-F:   AAG TTC TCC CGT GTC GCG TG     SEQ ID NO: 36

Br-G:   ATA GTC TCC CCC CGC CGA AA     SEQ ID NO: 37

Br-H:   TGA TTC TCC CTT TAC CAC CC     SEQ ID NO: 38

Br-I:   TAG GTC TCC CTA TGA GAG GG     SEQ ID NO: 39

Br-J:   ACC TTC TCC CGA GCC GCT AT     SEQ ID NO: 40
```

The ligation reaction was carried out in a multiplex formation using the following reaction conditions chosen to greatly minimize heterologous ligation: 0.5 µM total modified RNA, 6 µM each of ten different bridge oligonucleotides, 6 µM each of ten different ssDNA$_{10}$-PEG$_{2000}$-Reactants, 1× ligase buffer (Boehringer Mannheim), 0.4U/µl T4 DNA ligase, and 8% v/v ligase stability buffer (20 mM Tris-HCl, pH 7.5, 1 mM EDTA, 5 mM DTT, 60 mM KCl, 50% glycerol). Following a 3 to 4 hr incubation at 37° C., reaction products were separated by denaturing PAGE. Ligated RNAs were visualized by autoradiography or UV light shadowing, excised from the gel, and passively eluted from crushed gel slices. The elution volume was spun through a 0.45 micron microcentrifuge spin filter than was desalted on a Sephadex size exclusion column NAP column; Pharmacia).

As a result of the ligation, each RNA in a particular subpopulation was tethered to one of two possible dienes. Thus RNA subpopulation A comprised RNA molecules linked to diene 1 or diene 2, subpopulation B comprised RNA molecules linked to diene 3 or diene 4, . . . and RNA subpopulation J comprised RNA molecules linked to diene 19 or diene 20.

EXAMPLE 7

Biocatalysis, Selection, and Amplification Cycles

Each selection experiment was initiated with 2.4 nmole modified RNA library composed of 240 pmoles of each of RNA subpopulations A–J. A single cycle of (1) small molecule library assembly via biocatalysis, 2) selection for small molecule affinity to PBP2a, and (3) amplification of RNA biocatalysts responsible for assembly of selected small molecules was performed as summarized in FIG. 1. Specifically, each of free reactant libraries FR1–10 (described in Example XX and each comprised of approximately 4,000 monobactam members) was incubated with a mixture of RNA subpopulations A–J (a total of $10^{15}$ unique sequences) in the presence of 200 mM NaCl, 50 mM KCl, 5 mM each of $MgCl_2$ and $CaCl_2$, 20 µM each of $CuCl_2$ and $NiCl_2$, 10 µM each of $CoCl_2$, $ZnCl_2$, $MnCl_2$, and $FeCl_2$, and 50 mM HEPES, pH 7.0, thereby yielding ten separate biocatalyzed product libraries (P1–10, wherein the numeral indicates the free reactant library that used in the reaction). Each of P1–10 comprises the biocatalyzed products (monobactams) tethered to the RNA biocatalyst that catalyzed its formation. Biocatalysis reaction parameters for the 17 completed cycles are provided in Table 4.

TABLE 4

Biocatalyzed product library assembly reaction parameters.

| Cycle # | Reaction Volume | RNA Biocatalyst Concentration | Reactant Library Concentration | Duration of Incubation at 25° |
|---|---|---|---|---|
| 1 | 1200 µl | 2.0 µM | 20 mM | 16 hours |
| 2 | 400 µl | 1.0 µM | 20 mM | 14 hours |
| 3 | 400 µl | 1.0 µM | 20 mM | 12 hours |
| 4 | 200 µl | 1.0 µM | 20 mM | 6 hours |
| 5–14 | 100 µl | 1.0 µM | 20 mM | 4 hours |
| 15–17 | 200 µl | 0.25 µM | 10 mM | 2 hours |

Following the small molecule product assembly reaction, free reactants were removed on G25 Sephadex and the reacted biocatalyzed product library was concentrated and washed on a 30,000 molecular weight cut-off spin filter.

For selection cycles 1–6 only, the recovered RNA was reverse transcribed with Superscript II RNaseH⁻ reverse transcriptase (Life Technologies) at 46° C. for 45 min. prior to partitioning. The primer oligonucleotide utilized for reverse transcription was complementary to the 3'-defined primer annealing sequence common to all ten encoded modified RNA subpopulations; reverse transcription reaction conditions were otherwise as described by the enzyme supplier. The objective of the selection protocol was to capture biocatalyst-coupled monobactam inhibitors of PBP2a using PBP2a conjugated to beads via a disulfide-containing linker. To discard biocatalysis reaction products with affinity for bead components other than PBP2a, the recovered RNAs were first incubated with Sepharose 4B-sulfhydral at 30° C. with constant mixing. Following a 1 hour incubation in selection buffer (1.2 M NaCl, 20% v/v glycerol, and 20 mM HEPES, pH 7.0), the beads were removed and discarded and the supernatant was transferred to Sepharose 4B-S-S-PBP2a conjugates for incubation with mixing with the parameters listed in Table 5. The beads were then transferred to a micro-chromatography column and extensively washed prior to release of PBP2a and bound biocatalysts-coupled small molecules with 200 mM dithiothreitol (DTT).

TABLE 5

Selection of small molecules with affinity for PBP2a: reaction parameters.

| Cycle # | Reverse Transcription: Before or After Partitioning? | Reaction Volume | Quantity of Bead-Conjugated Active PBP2a in Reaction | Duration of Incubation at 30° |
|---|---|---|---|---|
| 1 | Before | 750 µl | 3825 pmole | 6 hours |
| 2 | Before | 250 µl | 1275 pmole | 6 hours |
| 3 | Before | 250 µl | 1275 pmole | 4 hours |
| 4 | Before | 120 µl | 480 pmole | 3 hours |
| 5–6 | Before | 60 µl | 240 pmole | 2 hours |
| 7–14 | After | 60 µl | 240 pmole | 2 hours |
| 15–17 | After | 38 µl | 160 pmole | 1 hour |

RNA biocatalysts in the DTT eluate were concentrated and washed on a 30,000 molecular weight cutt-off spin-filter then, for selection cycles 7–17, reverse transcribed with Superscript II RT.

cDNAs recovered from the selection step were amplified with Taq DNA polymerase (0.07 U/µl) in a multiplex PCR reaction that included a 3'-primer complimentary to the 3'-defined sequence of RNA subpopulations A–J, ten different 5'-primers, each complimentary to the unique 5' region of one of RNA subpopulations A–J present in the initial modified RNA library (see appendix for oligonucleotide sequences), and the following: 20 mM Tris-HCl, pH 8.5, 10 mM KCl, 10 mM $(NH_4)_2SO_4$, 2.25 mM $MgCl_2$, and 0.2 mM each of dATP, dGTP, dCTP, and dTTP. Thermal cycle parameters were an intial "melt" at 94° C. for 2 min followed by cycling between 94° C. for 30 sec, 66° C. for 30 sec, and 72° C. for 1 min. PCR products were purified using QiaQuick spin columns (Qiagen inc.) and the manufacturers recommended protocol.

Purified PCR products were transcribed with T7 RNA polymerase in a reaction consisting of 0.05–0.1 µM dsDNA template, 1 mM each of ATP, GTP, CTP, and 5-(4-pyridyl-methyl)UTP, 20 mM GMP, 0.1 µCi/µl [α-$^{32}$P]ATP, 12 mM $MgCl_2$, 5 mM DTT, 1 mM spermidine, 4% glycerol, 0.002% Triton X-100, and 50 mM Tris-HCl, pH 8.0. Following a typically 3-hour incubation at 37° C., transcripts were purified using RNeasy spin columns (Qiagen, Inc.) and the manufacturer's recommended procedure.

RNA subpopulation-specific 10-nucleotide ssDNA-2000 MW PEG-Dienes were ligated to the 5'-termini of RNAs in a multiplex reaction using T4 DNA ligase and a set of 10 different bridging oligos, each uniquely complimentary to a single 10-nt ssDNA:RNA subpopulation pair. Ligation reactions consisted of 5 µM RNA, 6 µM each bridging oligonucleotide, 6 M each 10mer-PEG-Diene pair, RNase inhibitor, T4 DNA ligase buffer (Roche), and 0.4 U/µl T4 DNA ligase. After purification of the ligation products by denaturing PAGE, the enriched RNA biocatalyst library was subjected to the next cycle of biocatalysis, selection, and amplification.

EXAMPLE 8

Analysis of RNA Biocatalysts Obtained from the Evolved Biocatalyzed Product Libraries Dideoxynucleotide termination sequencing of post-selection cycle PCR products was performed to analyze the evolution of the RNA biocatalyst (modified RNA) libraries over the course of the selection experiments. Reaction products were analyzed by denaturing PAGE; a shift from random sequence within the 100-nt contiguous random sequence block of the initial RNA libraries to significant non-randomness within this sequence block in evolved RNA libraries was an indication that the RNA populations were converging on functional sequences (data not shown).

As described above, each of the ten evolved biocatalyzed product libraries (P1–10) contained ten RNA subpopulations (designated A through J as described above) that corresponded, by virtue of their 5'-encoding sequence, to a different pair of diene reactants that were present during the selection experiments. The RNA libraries added to the first selection cycle were composed of an equal molar mixture of these ten subpopulations; the ratio of the ten subpopulations in the evolved libraries was expected to provide an indication of the favored diene reactants. Following selection cycle #17, the representation of the ten different RNA subpopulations (designated A through J) within each RNA library was determined by the following quantitative PCR procedure: for each biocatalyzed product library (P1 through P10), the RNA biocatalysts were purified and reverse transcribed, as described above, to yield ten corresponding RNA biocatalyst libraries (B1–B10). Then, a PCR reaction "master mix" containing all components except 5' primer was prepared and aliquoted to ten reaction tubes. Each of the ten reaction tubes received a different radiolabeled 5'-encoded primer (subpopulation specific primer) and PCR amplification was performed under efficient reaction conditions (linear amplification). Reaction products were separated on denaturing polyacrylamide gels and analyzed with a Packard InstantImager™. The subpopulation representation data (see Table 6) permitted a focused search for anti-PBP2a biocatalysis products within the RNA biocatalyst libraries.

Alternatively, the evolved RNA biocatalyst libraries B1–10 could be analyzed according to the following procedure:

Step 1. An oligonucletide complimentary to the conserved 3'-end of the RNAs is conjugated to a solid support (microtiter plate wells, beads, filters, etc). This oligonucleotide, referred to as the "capture oligo", will hybridize to all members of the RNA Library. Following conjugation, the solid support is thoroughly washed to remove free oligonucleotides.

Step 2: "Pre-hybridize" (equilibrate) the solid support with 4×SSC/0.5% sarkosyl buffer for one hour at 60° C.

Step 3: Remove pre-hybridization solution and add RNA library sample in 4×SSC/0.5% sarkosyl buffer. The quantity of added RNA should exceed (about 1.5×) the capacity of the conjugated oligonucleotides to ensure saturation. Add biotin-conjugated oligonucleotide (=5pDETECT oligonucleotide) that is complimentary to one of the possible 5'-encoded sequences (a separate hybridization reaction is set up for each 5pDETECT oligonucleotide, each being specific for one of the possible 5'-encoded sequences).

Step 4: Incubate the hybridization reaction for 1 hour at 60° C.

Step 5: Remove the hybridization solution and thoroughly wash the solid support with 1×SSC buffer.

Step. 6: To the solid support, add an excess of streptavidin-alkaline phosphatase conjugate in 1×SSC buffer and incubate for 30 min at room temperature.

Step 7: Remove the streptavidin-alkaline phosphatase conjugate solution and thoroughly wash the solid support with 1×SSC buffer.

Step 8: To the solid support, add either a chemiluminescent or\chromogenic alkaline phosphatase substrate. Mix and incubate at room temperature for a predetermined period of time (usually 10–30 minutes).

Step 9: Record emitted fluorescence with a luminometer (for chemiluminescent substrates), or absorbance with a spectrophotometer (for chromogenic substrates), and by comparison to appropriate controls, calculate the ratio of the possible 5'-encoded sequences in the RNA library population.

This assay may also be performed with a fluorescently labeled probe, as would be apparent to one of ordinary skill.

TABLE 6

RNA biocatalyst subpopulation representation. The ratio of each RNA biocatalyst subpopulation (A–J) within each RNA biocatalyst library (B1–B10) is expressed as a percentage of the total.

| RNA Biocatalyst Library | RNA Biocatalyst Subpopulation | | | | | | | | | |
|---|---|---|---|---|---|---|---|---|---|---|
| | A | B | C | D | E | F | G | H | I | J |
| B1  | 51.6 | 0.01 | 1.22 | 5.03  | 0.69  | 0.34 | 0.26 | 4.47 | 36.3 | 0.0  |
| B2  | 29.7 | 0.0  | 6.30 | 30.2  | 2.59  | 0.32 | 0.20 | 4.96 | 25.6 | 0.17 |
| B3  | 49.3 | 0.10 | 8.67 | 16.7  | 1.69  | 0.34 | 0.17 | 8.65 | 14.4 | 0.09 |
| B4  | 38.0 | 0.00 | 10.5 | 22.6  | 13.6  | 0.14 | 0.12 | 2.13 | 12.9 | 0.00 |
| B5  | 28.3 | 0.15 | 1.43 | 42.5  | 3.00  | 0.28 | 0.30 | 3.10 | 20.8 | 0.13 |
| B6  | 46.4 | 0.11 | 3.63 | 27.4  | 2.62  | 0.33 | 0.25 | 2.99 | 16.1 | 0.21 |
| B7  | 66.1 | 0.19 | 0.24 | 8.84  | 0.21  | 0.29 | 0.20 | 1.05 | 22.9 | 0.04 |
| B8  | 82.0 | 0.09 | 0.04 | 1.18  | 0.16  | 0.17 | 0.20 | 1.59 | 14.5 | 0.04 |
| B9  | 77.8 | 0.29 | 0.72 | 2.72  | 0.77  | 1.09 | 0.80 | 2.38 | 13.2 | 0.20 |
| B10 | 74.9 | 0.42 | 0.62 | 1.64  | 0.23  | 0.18 | 0.19 | 1.80 | 20.0 | 0.03 |

EXAMPLE 9

PBP2a Inhibition Activity of Products from Biocatalyst Subpopulations

Individual evolved RNA biocatalyst subpopulations (A–J) from each of biocatalyst libraries B1–10 chosen for further analysis were isolated by PCR amplification of selection cycle 17 PCR products using the appropriate subpopulation-specific 5'-primer. Resulting PCR products were transcribed with T7 RNA polymerase, transcripts were ligated to the appropriate 10mer-PEG$_{2000}$-Dienes with T4 DNA ligase, and ligated RNAs were purified by denaturing PAGE. Biocatalysis reactions were performed as described above (see selection cycle methods), except the RNA biocatalyst subpopulations (0.5 µM) were separately incubated with the three free reactant sublibraries (10 mM) that comprised the free reactant library utilized during the selection cycles (see Examples 1–3 for the individual free reactant sublibraries (C10–C44 and C50–C64) present in each free reactant library FR1–10). Following a two hour incubation at 25° C., free reactants were removed as described in the selection procedure and the biocatalysis reaction products were suspended in 12 µl assay buffer (500 mM NaCl, 0.05% Triton X-100, 20 mM HEPES, pH 7.0). PBP2a was added in 2 µl of assay buffer, bringing the PBP2a and biocatalysts concentrations to 1.1 µM and approximately 2.8 µM, respectively. Following a 90 minute incubation at 30° C., 2 µl of 0.5 µg/µl [$^{14}$C]benzylpenicillin was added to the reaction. Immediately following an additional 30 minute incubation at 30° C., the reaction was terminated by the addition of 200 µl CM Sepharose (50% suspension) in 10 mM sodium phosphate, 0.05% Triton X-100, pH 6.0. After a 15 minute room temperature incubation with constant mixing, the CM Sepharose beads with bound PBP2a were transferred to a Micro Bio-Spin column (Bio-Rad) and extensively washed to remove unbound benzylpenicillin. The washed beads were then carefully transferred to scintillation fluid and subjected to scintillation counting. All competition assay experiments included "no RNA" and "no reactant library" controls. Significant reactant sublibrary-specific inhibition was observed with biocatalysis products from the following subpopulations (denoted: [biocatalyst library number] [RNA subpopulation]-[diene reactant number])and free reactant sublibraries:

1. 3H-15 (i.e. RNA biocatalyst library B3, RNA subpopulation H, diene reactant 15)+free reactant sublibrary C43;
2. 3H-16+free reactant sublibrary C43;
3. 8I-17+free reactant sublibrary C24; and
4. 7I-18+free reactant sublibrary C63

Figure 6:
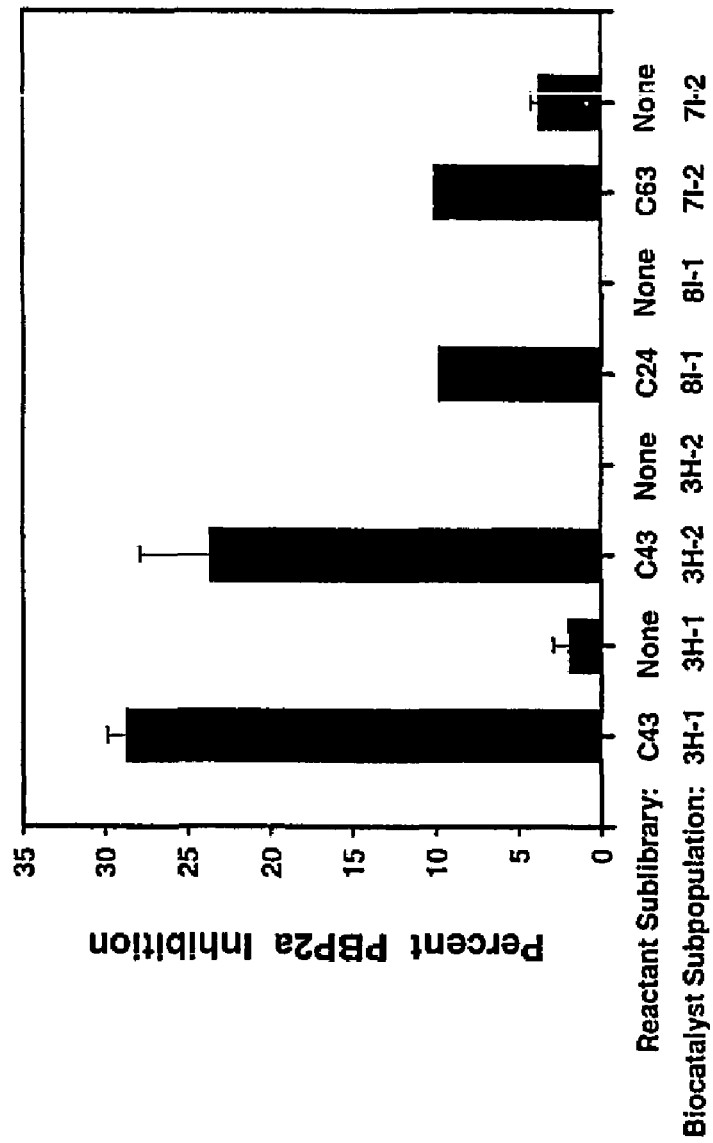
FIG. 6 illustrates the PBP2a inhibitory activity of products produced by particular biocatalyst subpopulations and free reactant sublibraries.

FIG. 6 illustrates the PBP2a inhibition activity of these subpopulations. Biocatalysis reactions that included these RNA subpopulations and other free reactant sublibraries (i.e., the other two sublibrary members of their respective free reactant library) did not yield active inhibitors; therefore, two-thirds of each of these free reactant libraries was omitted as a possible source of the reaction-contributing monobactam substrate. The RNA 3H subpopulation, with free reactant sublibrary C43 demonstrated the highest level of PBP2a inhibition and was the focus of additional studies.

EXAMPLE 10

Demonstration that RNA Structure is not Involved in the Observed PBP2a Inhibition To demonstrate that RNA biocatalyst subpopulation 3H biocatalysts were selected for PBP2a inhibition on the basis of their reaction products and not by an interaction between the RNA and PBP2a, ribonuclease I (RNase I)-digested and undigested biocatalysis reaction products were assayed for PBP2a inhibiton. The RNase I digestion conditions were shown to reduce the oligoribonucleotide component of the biocatalysts to mononucleotides, and the digestion reaction components themselves were shown not to inhibit PBP2a (data not shown). The results indicate that intact RNA is not a component of the inhibition mechanism (FIG. 7).

EXAMPLE 11

Isolation and Analysis of Individual Biocatalysts

Individual biocatalysts present in RNA biocatalyst subpopulation 3H and RNA biocatalyst subpopulation 8I were isolated by cloning into the vector PCR-Script™ Amp using a cloning kit from Stratagene® and the manufacturer's recommended procedure. Vector inserts were sequenced using a BigDye™ terminator cycle sequencing kit (Applied Biosystems) and reactions were processed by the sequencing facility of National Jewish. Center (Denver, Colo.). Sequence alignments for clones from biocatalyst subpopulations are provided in FIGS. 2 and 4. Sequence alignments were produced with Vector NTI® software (Informax, Inc.).

Figure 8:
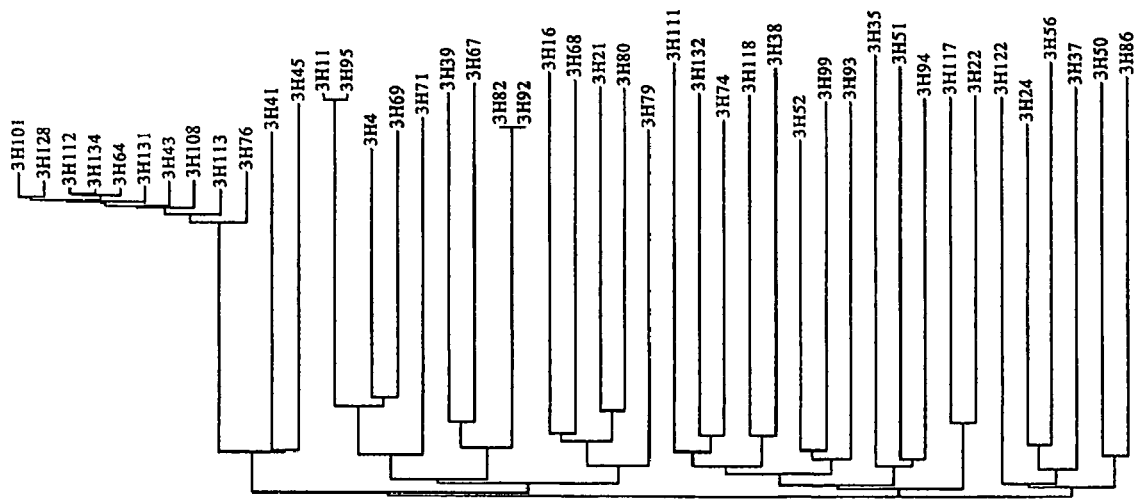
FIG. 8 illustrates a phylogenetic analysis of individual biocatalysts from the 3H subpopulation.

A preliminary phylogenetic comparative analysis was performed on clones from the RNA biocatalyst subpopulation 3H. While an alignment of these sequences (FIG. 2) reveals a family with very high similarity (suggesting that they were clonally-derived), sequence similarities among the remaining clones are fairly limited. The primary sequence diversity is highlighted by the phylogenetic tree in FIG. 8.

Approximately one-half of the illustrated clones have been screened for their ability to catalyze the synthesis of PBP2a inhibitors utilizing monobactam reactants present in free reactant sublibrary C43; significant PBP2a inhibition was observed with each. FIG. 3 illustrates the Inhibition of PBP2a by biocatalysis reaction products from RNAs found in distant branches of the subpopulation 3H phylogenetic tree. The finding that diverse sequences generate PBP2a inhibition is suggestive of the presence of multiple inhibitor structures within this population.

EXAMPLE 12

PBP2a Inhibition Levels

PBP2a inhibition assays described herein permitted a single-point determination of inhibitor $K_i$ with assumptions that yield worst-case values. In arriving at the inhibition constant, it was assumed that 100% of the biocatalysts in the biocatalysis reaction had generated product (unlikely), that the full 90 min incubation period was required to achieve the observed level of inhibition (unlikely, but not yet investigated), and that the deacylation or off rate ($k_3$) is 10-fold slower than the acylation or on rate ($k_2$). $IC_{50}$ value estimates were derived from the $K_i$ values and knowledge of approximate molecular weight.

EXAMPLE 13

Synthesis of Compound (j)

Compound (j) of the present invention may be prepared following the scheme and reactions conditions outlined below. All chemicals were obtained from either Aldrich Chemical Co. and used without further purification unless otherwise noted. $BF_3.OEt_2$ was purchased from Aldrich as the redistilled reagent. All anhydrous reactions were performed under Argon. THF and pyridine were freshly distilled.

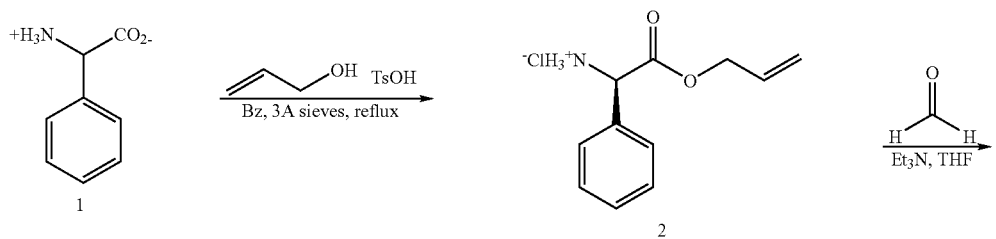
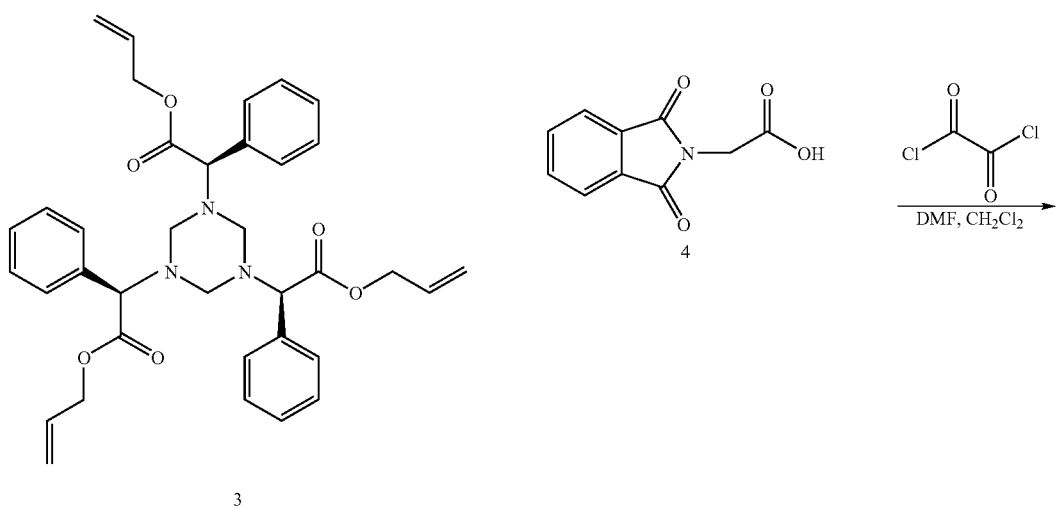
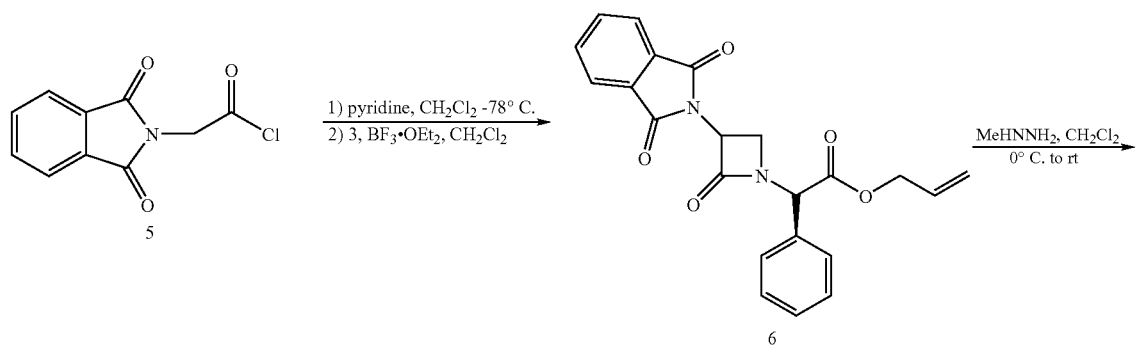
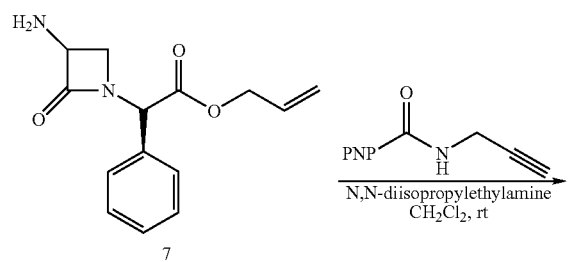

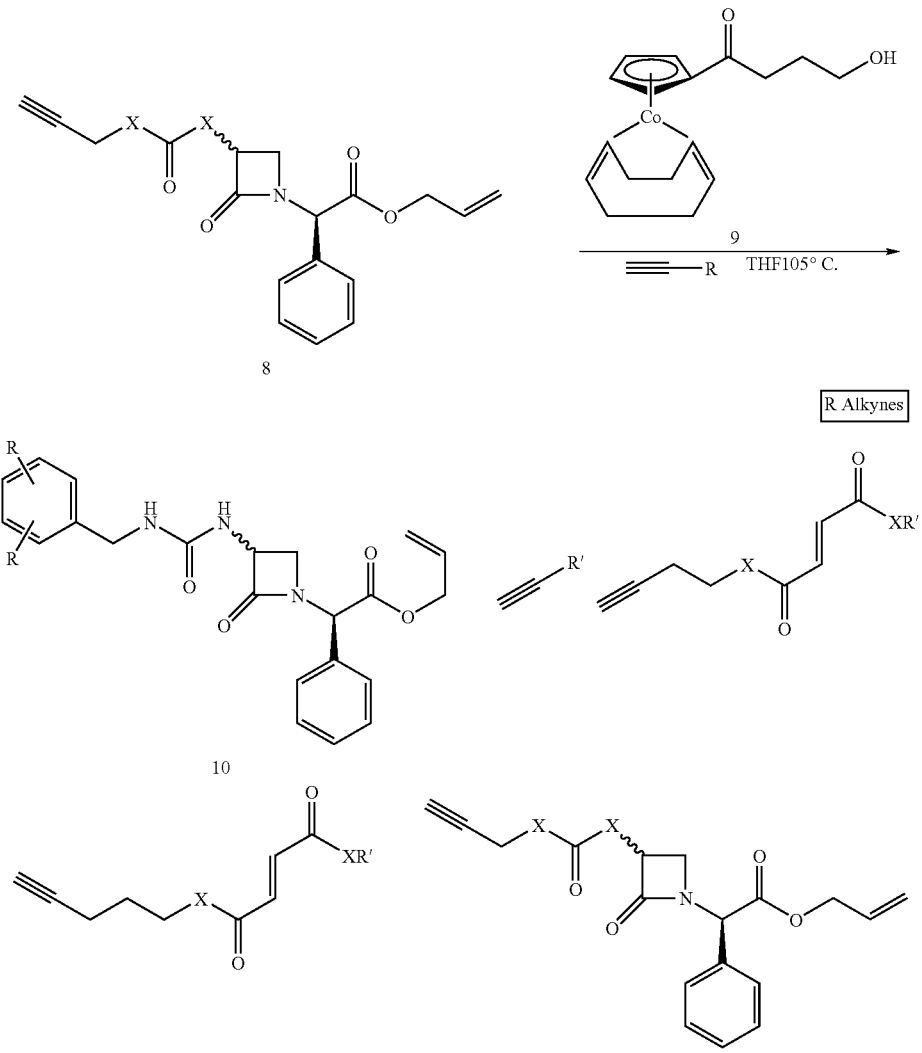

X = O, NH
R' = H, C₁–C₁₀
with heteroatoms

The compounds in this scheme may be synthesized as follows:

(2). To a mixture of (R)-phenylglycine (10.0 g, 66.0 mmoles) and allyl alcohol (17.95 mL, 264 mmoles) in benzene (150 mL) was added p-toluene sulfonic acid (16.4 g, 86.0 mmoles). The reaction round bottom flask was fitted with a Dean-Stark apparatus and reflux condenser and the mixture was heated to (105° C.) for 18 hr. The mixture was then cooled upon which it became a white solid and the remaining solvent removed by rotary evaporation. EtOAc (500 mL) was added and the solution, in a 1 L Erlenmeyer, was cooled in an ice bath. While stirring, saturated $Na_2CO_3$ (300 mL) was added to the solution. The biphasic solution was transferred to a 1 L separatory funnel, the aqueous layer removed and the organic layer washed again with saturated $Na_2CO_3$ (300 mL), brine, and then dried over $MgSO_4$. The concentrated light brown oil was dissolved in diethyl ether (300 mL), cooled with an ice bath and while stirring, 2.0 M HCl (obtained from Aldrich Chemical Co and stored in the refrigerator) in ether was slowly added. The salt product precipitated out and excess 2.0 M HCl in ether was added. The precipitate was collected, washed with cold diethyl ether, and dried in a dessicator over $P_2O_5$ under high vacuum overnight yielding 13.88 g (92% yield) of solid product.

(3). A mixture of glycinate ester 2 (13.88 g, 60.96 mmoles), formaldehyde (5.95 mL of 37 wt. % solution in water, 73.15 mmoles) and $Et_3N$ (10.2 mL, 76.15 mmoles) in THF (200 mL) were stirred for 5 hr at room temperature followed by vacuum filtration to remove $Et_3N^+HCl^-$.[4] The THF solvent was removed by rotary evaporation and the residue was dissolved in EtOAc (200 mL), washed with water (2×150 mL), brine, and then dried over $MgSO_4$. Upon concentration, triazine 3 was obtained (12.39 g, 99% yield). The compound was further dried in refluxing benzene, by passing the condensate over activated 3Å molecular sieves (500 mL) for 18 hr.[2]

(5). To a vigorously stirring solution of N-phthaloylglycine 4 (20.7 g, 100.8 mmoles) and oxalyl chloride (13.2 mL, 151.2 mmoles) in anhydrous $CH_2Cl_2$ (110 mL) were added anhydrous DMF (0.33 mL) dropwise at room temperature. The reaction stirred until the evolution of gas had ceased (2 h). The reaction mixture was concentrated and coevaporated with anhydrous CH$_2$Cl$_2$ (3×100 mL) to remove residual oxalyl chloride, to give 22.5 g (100% crude yield) of phthalimidoacetyl chloride 5 as a light yellow solid.

(6). To a solution of triazine 3 (12.29 g, 20.16 mmoles) in anhydrous CH$_2$Cl$_2$ (80 mL) was added BF$_3$.OEt$_2$ (7.66 mL, 60.48 mmoles) at room temperature and the reaction stirred for 20 minutes followed by cooling to −50° C. to give a borane-imine complex. In a separate container, a solution of phthalimidoacetyl chloride 5 (100.8 mmoles) in anhydrous CH$_2$Cl$_2$ (100 mL) was cooled to −78° C. and pyridine (8.15 mL, 100.8 mmoles) added, followed by stirring for 5 minutes (it is imperative that the triazine is dry or the imine will not form and the product will be the N-phthalimidoacetyl amide. The drying apparatus used incorporates a condenser above an addition funnel, containing 3A molecular sieves, that is connected to a 500 mL round bottom flask equipped with a stir bar). The borane-imine complex was then added and the reaction stirred at −78° C. for 30 minutes, allowed to warm to room temperature and stirred for an additional 2 hr. The mixture was washed with 10% CuSO$_4$ (2×500 mL), saturated Na$_2$CO$_3$ (500 mL), water (500 mL), brine and dried over MgSO$_4$. The concentrated light yellow residue was dissolved in CH$_2$Cl$_2$ (300 mL) and placed in a refrigerator overnight. The N-phthaloylglycine precipitate was removed by vacuum filtration and desired product isolated by silica gel flash chromatography (35% EtOAc/Hexanes). Typical yields range from 50–70%.

(7). A solution of β-lactam 6 (1.22 g, 3.125 mmoles) in anhydrous CH$_2$Cl$_2$ was cooled to 0° C. then methyl hydrazine slowly added. The reaction mixture was allowed to warm to room temperature and stirred for 48 hr. The CH$_2$Cl$_2$ solvent was removed by rotary evaporation and the desired product isolated by silica gel flash chromatography (3% MeOH/CH$_2$Cl$_2$). The product was obtained with 72% yield.

(8). To a solution of β-lactam 7 (1.64 g, 6.32 mmoles) in anhydrous CH$_2$Cl$_2$ was added prop-2-ynyl-carbamic acid 4-nitro-phenyl ester (1.53 g, 6.96 mmoles) and N,N-diisopropylethylamine (1.33 ml, 7.59 mmoles). The reaction mixture was stirred at room temperature for 1 hr. The CH$_2$Cl$_2$ solvent was removed by rotary evaporation and the yellow residue was dissolved in EtOAc (200 mL), washed with sodium carbonate until organic layer becomes colorless then dried over MgSO$_4$. The CH$_2$Cl$_2$ solvent was removed by rotary evaporation and the desired product isolated by silica gel flash chromatography (ramped from 30% EtOAc/Hexanes to 55% EtOAc/Hexanes). The product 8 was obtained with 56% yield.

(10). In an inert atmosphere glovebox, monobactam alkyne 8 (0.667 mmol), one or more other alkyne (total amount 1.33 mmol) and the cobalt cyclotrimerization catalyst 9 were combined in a sealable reaction vessel with 13.3 mL of dry deoxygenated THF box. The reaction tube was sealed, taken out of the box and heated to 105° C. for 72 hours. The reaction mixture was then allowed to come to room temperature and the THF removed under reduced pressure. Approximately 10 mL of MeOH and 75 mg of activated charcoal were added and the mixture was stirred at ambient temperature for 5 minutes. The mixture was filtered ant the filtrated concentrated under reduced pressure to give a reddish brown residue. The products were carried on to the next step without further purification.

(11). In an inert atmosphere glovebox, the cyclotrimerization products 10 were dissolved in 0.2 M TEAA in DMF (30.75 ml, 6.15 mmoles). Tetrakistriphenylphosphine palladium (46 mg, 0.07 equiv.) was added to the reaction and the reaction was left to stir 15 hr outside the glovebox at ambient temperature. The DMF solvent was removed by high vacuum rotary evaporation and the products were purified by anion-exchange chromatography and HPLC.

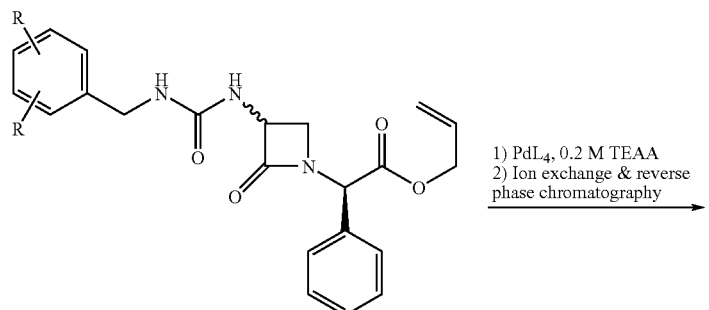

10

1) PdL$_4$, 0.2 M TEAA
2) Ion exchange & reverse phase chromatography

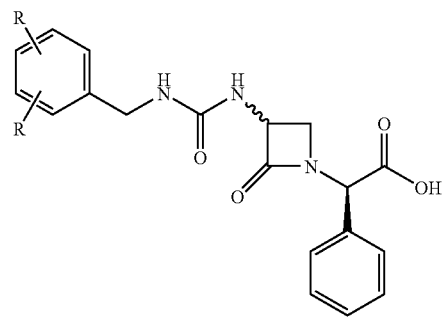

11

-continued

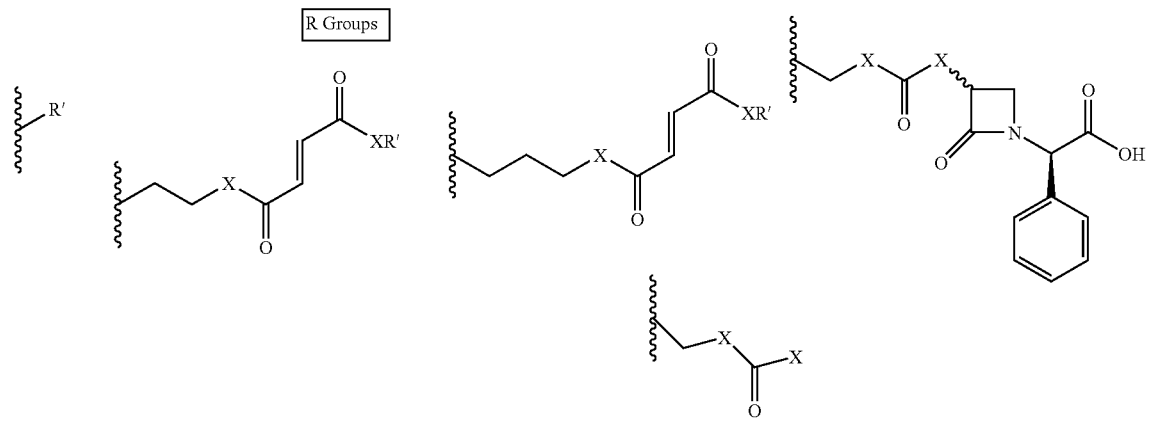

R Groups

X = O, NH
R' = H, C₁–C₁₀ with heteroatoms

---

What is claimed is:

1. A compound having the formula:

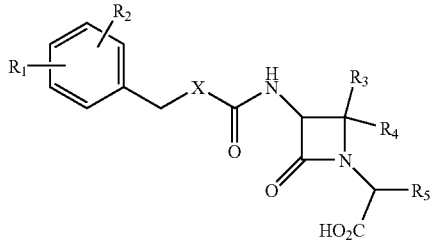

(a)

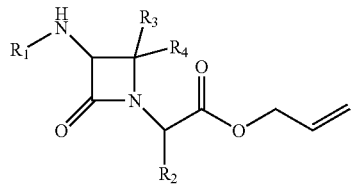

(b)

or a pharmaceutically acceptable salt thereof, wherein:
wherein X is $CH_2$, NH, or O;

$R_1$, is selected from the group consisting of $C_1$–$C_{20}$ alkyl, $C_2$–$C_{20}$ akenyl, $C_2$–$C_{20}$ alkynyl, $OR^6$, $C(O)R^6$, carboalkoxyalkyl, a heterocyclyl selected from the group consisting of furanyl, pyridyl, pyrrolyl and imidazolyl, aromatic hydrocarbon and cycloalkyl, all of which may be optionally substituted by one or more of the groups selected from $C_1$–$C_{20}$ alkyl, $C_2$–$C_{20}$ alkenyl, $C_2$–$C_{20}$ alkynyl, cycloalkyl, a heterocyclyl selected from the group consisting of furanyl, pyridyl, pyrrolyl and imidazolyl, aryl, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, $OR^6$, $CONR^6$, wherein all said substituents may be optionally substituted with one or more selected from the group consisting of halogen, $C_1$–$C_{20}$ alkyl, $C_2$–$C_{20}$ alkenyl, $C_2$–$C_{20}$ alkynyl, cycloalkyl, $OR^6$, $C(O)R^6$, carboalkoxyalkyl, cyano, and nitro; $R_2$, $R_3$, $R_4$ and $R_5$ are independently selected from the group consisting of hydrogen, $C_1$–$C_{20}$ alkyl, $C_2$–$C_{20}$ akenyl, $C_2$–$C_{20}$ alkynyl, $OR^6$, $C(O)R^6$, carboalkoxyalkyl, a heterocyclyl selected from the group consisting of furanyl, pyridyl, pyrrolyl and imidazolyl, aromatic hydrocarbon and cycloalkyl, all of which may be optionally substituted by one or more of the groups selected from $C_1$–$C_{20}$ alkyl, $C_2$–$C_{20}$ alkenyl, $C_2$–$C_{20}$ alkynyl, cycloalkyl, a heterocyclyl selected from the group consisting of furanyl, pyridyl, pyrrolyl and imidazolyl, aryl, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, $OR^6$, $CONR^6$, wherein all said substituents may be optionally substituted with one or more selected from the group consisting of halogen, $C_1$–$C_{20}$ alkyl, $C_2$–$C_{20}$ alkenyl, $C_2$–$C_{20}$ alkynyl, cycloalkyl, $OR^6$, $C(O)R^6$, carboalkoxyalkyl, cyano, and nitro; and $R^6$ is selected from the group consisting of hydrogen, halogen, $C^1$–$C^{20}$ alkyl, aromatic hydrocarbon, and alkylaryl, wherein all said substituents may be optionally substituted by one or more carboalkoxy, amino, hydroxyl, carboxyl, lower alkyl, lower alkenyl, lower alkynyl, halo, cyano, nitro, carboxyalkyl, and unsubstituted carbamoyl.

2. A monobactam with anti-PBP2a activity, wherein said monobactam is prepared by the process comprising:
   a) providing a monobactam core alkyne having the structure wherein $R_1$ is selected from the group consisting of:

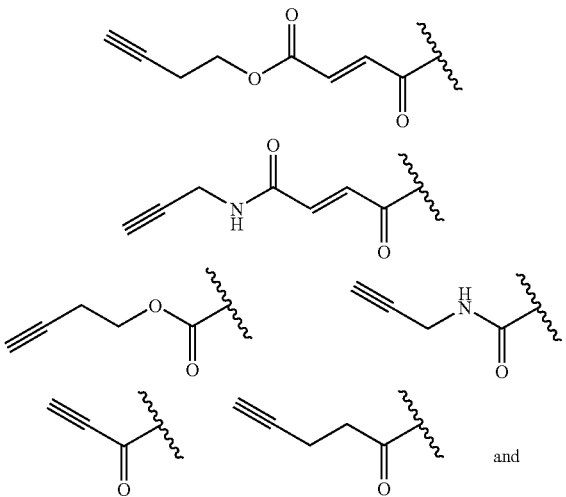

and $R_2$ is selected from the group consisting of:

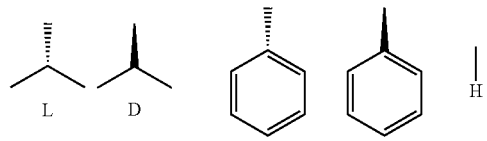

$R_3$ and $R_4$ are independently selected from the group consisting of hydrogen, $C_1$–$C_{20}$ alkyl, $C_2$–$C_{20}$ alkenyl, $C_2$–$C_{20}$ alkynyl, $OR^5$, $C(O)R^5$, carboalkoxyalkyl, heterocyclyl, aromatic hydrocarbon and cycloalkyl, all of which may be optionally substituted by one or more of the groups selected from $C_1$–$C_{20}$ alkyl, $C_2$–$C_{20}$ alkenyl, $C_2$–$C_{20}$ alkynyl, cycloalkyl, a heterocyclyl selected from the group consisting of furanyl, pyridyl, pyrrolyl and imidazolyl, aryl, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^5$, $OR^5$, $CONR^5$ wherein all said substituents may be optionally substituted with one or more selected from the group consisting of halogen, $C_1$–$C_{20}$ alkyl, $C_2$–$C_{20}$ alkynyl, cycloalkyl, $OR^5$, $C(O)R^5$, carboalkoxyalkyl, cyano, and nitro; and $R^5$ is selected from the group consisting of hydrogen, halogen, $C_1$–$C_{20}$ alkyl, aromatic hydrocarbon, and alkylaryl, wherein all said substituents may be optionally substituted by one or more carboalkoxy, amino, hydroxyl, carboxyl, lower alkyl, lower alkenyl, lower alkynyl, halo, cyano, nitro, carboxyalkyl, and unsubstituted carbamoyl;

b) reacting said monobactam alkyne under conditions that promote cyclotrimerization with at least one alkyne selected from the group consisting of:
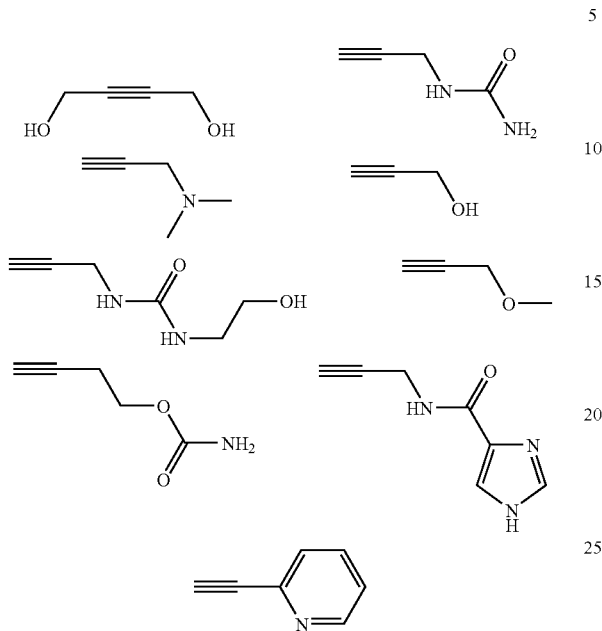
with the proviso that when $R_1$ is selected from the group consisting of:
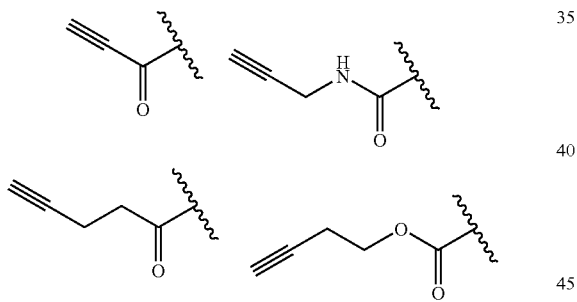
the cyclotrimerization reaction mixture also includes at least one alkyne selected from the group consisting of:
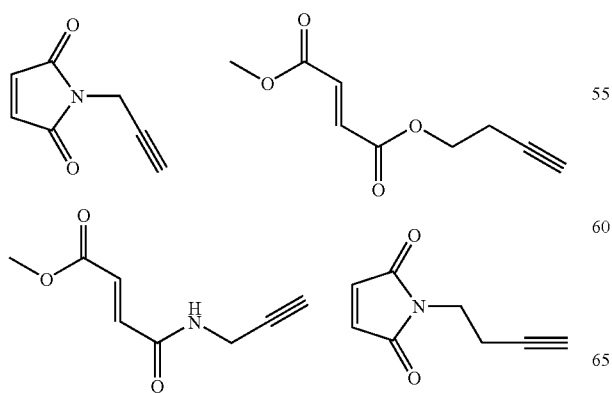
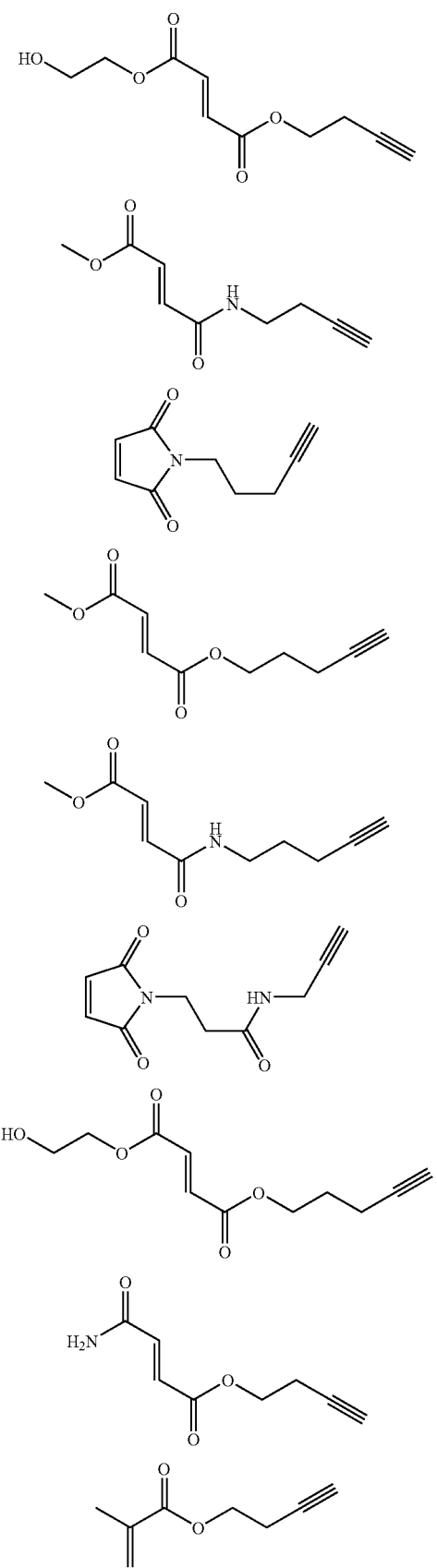

c) performing a Diels-Alder reaction between the cyclo-trimerization product of b) and a diene reactant selected from the group consisting of:

whereby a monobactam with anti-PBP2a activity may be prepared.
3. A monobactam having the formula:
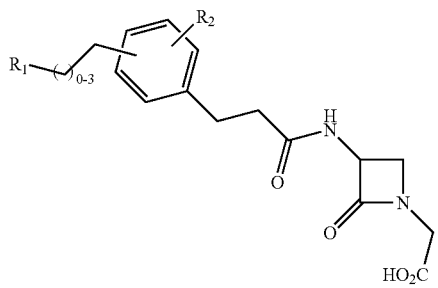
or pharmaceutically acceptable salt thereof, wherein $R_1$ is the Diels-Alder product formed by the reaction of
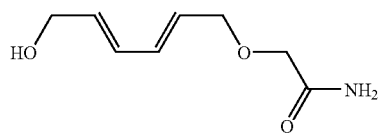
with the functionality on an alkyne selected from the group consisting of:
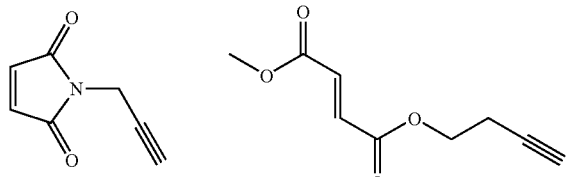
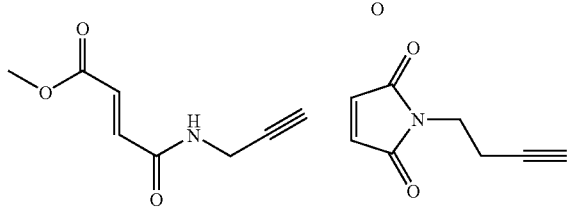
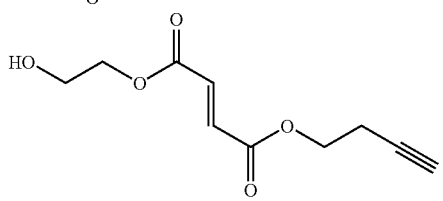
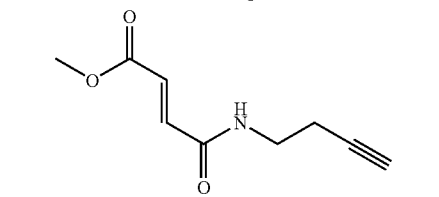
-continued
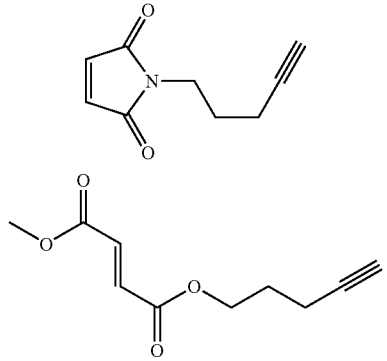
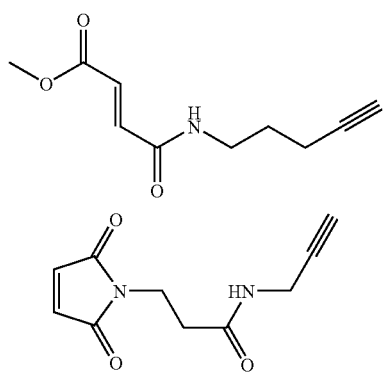
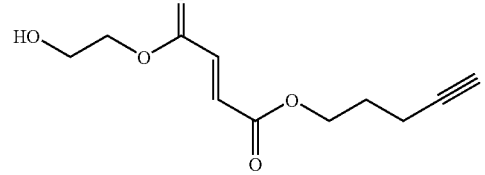
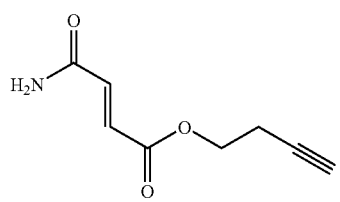
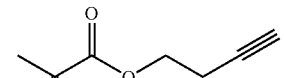
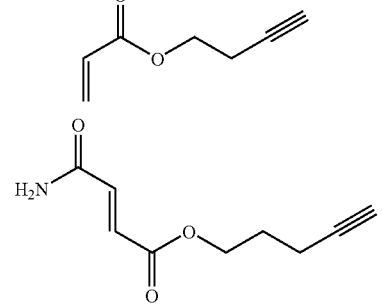

and wherein $R_2$ is the functionality on an alkyne selected from the group consisting of:

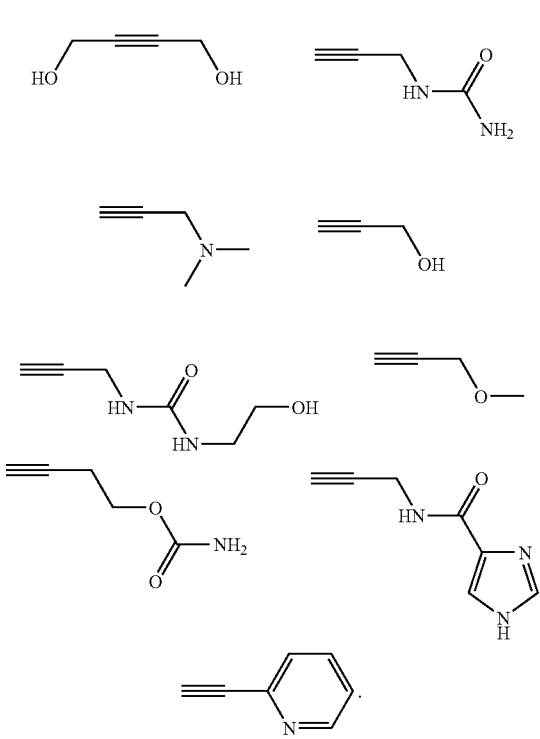

4. A monobactam compound with the following formula:

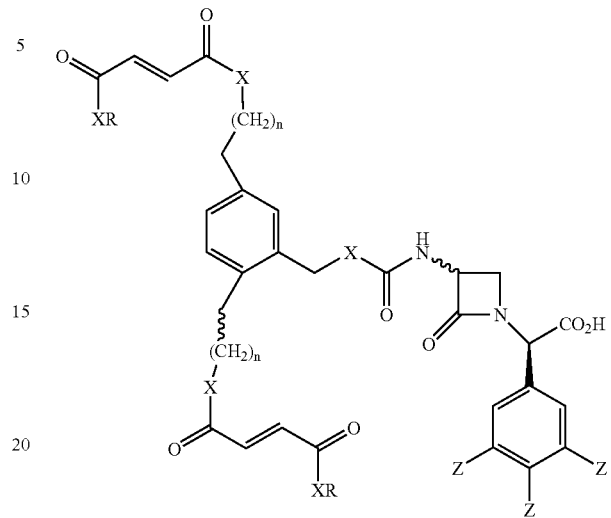

wherein each n is independently 0–4;
each X is independently O, S, $CH_2$ or NH;
each R is independently lower alkyl optionally substituted with $OR_1$, where $R_1$ is H or lower alkyl; and
each Z is independently H; halogen; OH; phenyl, heteroaromatic, or lower alkyl optionally substituted with one or more halogen, OH, phenyl or heteroaromatic groups.

* * * * *